US008747924B2

(12) United States Patent
Pasinetti et al.

(10) Patent No.: US 8,747,924 B2
(45) Date of Patent: Jun. 10, 2014

(54) METHODS FOR PREVENTING AND TREATING NEURODEGENERATIVE DISEASES

(75) Inventors: Giulio Maria Pasinetti, New York, NY (US); Lap Ho, New York, NY (US); Jun Wang, Flushing, NY (US)

(73) Assignee: Icahn School of Medicine At Mount Sinai, New York, NY (US)

( * ) Notice: Subject to any disclaimer, the term of this patent is extended or adjusted under 35 U.S.C. 154(b) by 0 days.

(21) Appl. No.: 12/942,785

(22) Filed: Nov. 9, 2010

(65) Prior Publication Data

US 2011/0111072 A1 May 12, 2011

Related U.S. Application Data

(63) Continuation of application No. PCT/US2009/043392, filed on May 8, 2009.

(60) Provisional application No. 61/051,866, filed on May 9, 2008.

(51) Int. Cl.
*A61K 36/87* (2006.01)
*A61K 31/70* (2006.01)
*A61K 31/35* (2006.01)
*A61K 38/00* (2006.01)
*A61P 25/28* (2006.01)

(52) U.S. Cl.
USPC ............. 424/766; 514/17.8; 514/456; 514/27

(58) Field of Classification Search
None
See application file for complete search history.

(56) References Cited

U.S. PATENT DOCUMENTS

| 5,773,262 | A | 6/1998 | Ariga et al. | |
|---|---|---|---|---|
| 6,544,581 | B1 | 4/2003 | Shrikhande et al. | |
| 2003/0017998 | A1* | 1/2003 | Snow et al. ...................... | 514/27 |
| 2004/0115285 | A1* | 6/2004 | Rohdewald .................. | 424/725 |
| 2007/0071871 | A1 | 3/2007 | Shrikhande et al. | |
| 2007/0122504 | A1 | 5/2007 | Moon et al. | |

OTHER PUBLICATIONS

Prieur, C., Rigaud, J., Cheynier, V., Moutounet, M. (1994) Oligomeric and Polymeric Procyanidins from Grape Seeds. Phytochemistry vol. 36, No. 3 pp. 781-784.*
Nunez, V., Gomez-Cordoves, C., Bartolome, B., Hong, Y-J and Mitchell A.E. (2006) Non-galloylated and galloylated proanthocyanidin oligomers in grape seeds from *Vitus vinifera* L. cv. Graciano, Tempranillo and Cabernet Sauvignon. J. Sci. Food Agric. 86: 915-921.*
Plumb, G.W., Pasqual-Teresa, S.D., Santos-Buelga, C, Cheynier, V. And Williamson, G. (1998) Antioxidant Properties of Catechins and Proanthocyanidins: Effect of Polymerisation, Galloylation and Glycosylation. Free Rad. Res., vol. 29, pp. 351-358.*
Plumb et al. (1998) Free Rad. Res. vol. 29, pp. 351-358.*
Lu et al. (2008) Food Res. Inter. 41, pp. 130-137.*
Battesin et al. (2008) Food Chem. 108, pp. 228-233.*
Prieur et al. (1994) Phytochemistry, vol. 36, No. 3, pp. 781-784.*
Labarbe et al. (1999) J. Agric. Food Chem. 47, pp. 2719-2723.*
Borbalan, et al., "Study of the Polyphenol Content of Red and White Grape Varieties by Liquid Chromatography-Mass Spectrometry and Its Relationship to Antioxidant Power", *Journal of Chromatography*, 1012:31-38 (2003).
Brouillard, et al., "Polyphenols Produced During Red Wine Ageing", *BioFactors*, 6:403-410 (1997).
Cantos, et al., "Varietal Differences Among the Polyphenol Profiles of Seven Table Grape Cultivars Studied by LC-DAD-MS-MS", *Journal of Agricultural and Food Chemistry*, 50:5691-5696 (2002).
De La Hera Orts, et al., "Effect Deficit Irrigation on Anthocyanin Content of Monastrell Grapes and wines", *J. Int. Sci. Vigne Vin*, 39(2):47-55 (2005).
Esteban, et al., "Effect of Irrigation on Changes in the Anthocyanin Composition of the Skin of CV Tempranillo (*Vitis vinifera* L) Grape Berries During Ripening", *Journal of the Science of Food and Agriculture*, 81:409-420 (2001).
Ginjom, et al., "Phenolic Contents and antioxidant Activities of Major Australian Red wines Throughout the winemaking Process", *Journal of Agricultural and Food Chemistry*, 58:10133-10142 (2010).
Ho, et al., "Heterogenity in Red Wine Polyphenolic Contents Differentially Influences Alzheimer's Disease-Type Neuropathology and Cognitive Deterioration", *J Alzheimers Dis.*, 16(1):59-72 (2009).
Lee, et al., "Evidence of Vintage Effects on Grape Wines Using $^1$H NMR-Based Metabolomic Study", *Analytica Chimica Acta*, 648:71-76 (2009).
Manach, et al., "Polyphenols: Food Sources and Bioavailability", *American Society for Clinical Nutrition*, 79:727-747 (2004).
Masa, et al., "Varietal Differences among the Flavonoid Profiles of White Grape Cultivars Studied bu High-Performance Liquid Chromatography", *Journal of Chromatography*, 1164:291-297 (2007).
Monogas, et al., "MALDI-TOF MS analysis of Plant Proanthocyanidins", *Journal of Pharmaceutical and Biomedical analysis*, 51:358-372 (2010).
Morris, et al., "Developments of a Water-Maze Procedure for Studying Spatial Learning in the Rat", *Journal of Neuroscience Methods*, 11:47-60 (1984).
Perez-Magarino, et al., "Evolution of Flavanols, Anthocyanins, and Their Derivatives During the Aging of Red Wines Elaborated from Grapes Harvested at Different Stages of Ripening", *Journal of Agricultural and Food Chemistry*, 52:1181-1189 (2004).

(Continued)

*Primary Examiner* — Chris R Tate
*Assistant Examiner* — Russell Fiebig
(74) *Attorney, Agent, or Firm* — Baker Botts L.L.P.

(57) ABSTRACT

The present invention provide a method for the prevention and treatment of a neurodegenerative disease including Alzheimer's Disease, Huntington's Disease, and Parkinson's Disease, using a grape seed extract or one or more compounds derived therefrom. In particular, the present invention provides a method to treat a patient diagnosed with, or at the risk of developing, a neurodegenerative disease by administering a pharmaceutical composition comprising a grape seed extract or one or more compounds derived therefrom to the patient in a therapeutic amount to reduce the accumulation, aggregation or deposition of amyloid beta or its oligomers, and/or to reduce the misfolding, accumulation and/or aggregation of tau proteins or other proteins.

25 Claims, 30 Drawing Sheets

(56) References Cited

OTHER PUBLICATIONS

Radovanovic, et al., "Phenolic Profile and free Radical-Scavenging Activity of Cabernet Sauvignon Wines of Different Geographical Origins from the Balkan Region", *J. Sci. Food Agric.*, 90:2455-2461 (2010).

Sirk, et al., "Molecular Binding of Catechins to Biomembranes: Relationship to Biological Activity", *Journal of Agricultural and Food Chemistry*, 57(15):6720-6728 (2009).

Wang, et al., "Moderate Consumption of Cabernet Sauvignon Attenuates Aβ Neuropathology in a Mouse Model of Alzheimer's Disease", *The FASEB Journal*, 20(13):2313-2320 (2006).

Xu, et al., "Survey of Polyphenol Constitutes in Grapes and Grape-Derived Products", *Journal of Agricultural and Food chemistry*, 59:10586-10593 (2011).

Yokotsuka, et al., "Changes in Anthocyanins in Berry Skins of Merlot and Cabernet Sauvignon Grapes Grown in Two Soils Modified With Limestone or Oyster shell Versus a Native Soil Over Two Years", *Am. J. Enol., Vitiv.*, 50(1):1-12 (1999).

Kim, et al., "Proteomics Analysis of the Actions of Grape Seed Extract in Rat Brain: Technological and Biological Implications for the Study of the Actions of Psychoactive Compounds", *Life Sci.*, 78(18):2060-2065 (2006).

Torres, et al., "Conjugation of catechins with cysteine generates antioxidant compounds with enhanced neuroprotective activity", *Phytochemistry*, 66:2032-2037 (2005).

Deshane, et al., "Proteomics Analysis of Rat Brain Protein Modulations by Grape Seed Extract", *J. Agric. Food Chem.*, 52:7872-7883 (2004).

Vivas, et al., "Differentiation of proanthocyanidin tannis from seeds, skins and stems of grapes (*Vitis vinifera*) by matrix-assisted laser desoprtion/ionization time-of-flight mass spectometry and thioacidolysis/liquid chromatography/electrospray ionization mass spectometry", *Analytica Chimica Acta*, 513:247-256 (2004).

"Research present Alzheimer's and Autism Breakthroughs," Newswise Medical News, Nov. 7, 2007, pp. 1-3, downloaded on Jan. 24, 2008 from <http://www.newswise.com/articles/views/535185/>.

Vinson et al., "MegaNatural®Gold grapeseed extract: *in vitro* antioxidant and *in vivo* human supplementation studies." J Med Food. 2001 Spring;4(1):17-26.

Porat et al., "Inhibition of amyloid fibril formation by polyphenols: structural similarity and aromatic interactions as a common inhibition mechanism." Chem Biol Drug Des. Jan. 2006;67(1):27-37.

Ono et al., "Effects of grape seed-derived polyphenols on amyloid β-protein self-assembly and cytotoxicity." J. Biol Chem. Nov. 21, 2008;283(47):32176-87. Epub Sep. 24, 2008.

Ho et al., "Grape seed polyphenolic extract as a potential novel therapeutic agent in tauopathies." J Alzheimers Dis. 2009;16(2):433-9.

Wang et al., "Grape-derived polyphenolics prevent Aβ oligomerization and attenuate cognitive deterioration in a mouse model of Alzheimer's disease." J Neurosci. Jun. 18, 2008;28(25):6388-92.

Pfleger et al., "Grape-seed polyphenolic extract improves the eye phenotype in a *Drosophila* model of tauopathy." Int J Alzheimers Dis. Aug. 24, 2010;2010.

\* cited by examiner

A

B

C

D

METHODS FOR PREVENTING AND TREATING NEURODEGENERATIVE DISEASES

CROSS REFERENCE TO RELATED APPLICATIONS

This application is a continuation of International Application No. PCT/US2009/043392, filed May 8, 2009, which claims the benefit of U.S. Provisional Application Ser. No. 61/051,866, filed May 9, 2008, both of which are hereby incorporated by reference in their entireties, and from which priority is claimed.

GRANT INFORMATION

This invention was made with government support under grant number NIH 1 PO1 AT004511-02 awarded by the National Institute of Health. The U.S. Government has certain rights in the invention.

FIELD OF THE INVENTION

The present invention relates to the use of a grape seed extract for the prevention and treatment of a neurodegenerative disease. In particular, the present invention provides a method of treating a patient diagnosed with, or at the risk of developing, a neurodegenerative disease by administering a pharmaceutical composition comprising a grape seed extract or one or more compounds derived therefrom to the patient in an effective amount to reduce the accumulation, aggregation and/or deposition of amyloid beta or its oligomers and/or to reduce the misfolding, accumulation and/or aggregation of tau proteins or other proteins.

BACKGROUND OF THE INVENTION

Neurodegenerative diseases are associated with conditions in which neuronal cells deteriorate, lose function, and often die. As they are generally progressive, the consequences of neurodegenerative diseases are often devastating. Patients with neurodegenerative disease may suffer severe deterioration in cognitive or motor skills. As a result, their quality of life and life expectancy may be considerably reduced. In humans, these diseases include, but are not limited to, Alzheimer's Disease, Parkinson's Disease, Amyotrophic Lateral Sclerosis, Huntington's Disease, Fronto-Temporal Dementia, and Cortico Basal Degeneration, among others.

Parkinson's Disease is a progressive disorder that affects brain neuronal cells controlling muscle movement. These neuronal cells make dopamine, which is an important chemical for transmitting signals between cells to facilitate movement of the body. Therefore, the loss of these neurons leads to movement disorders, such as tremor and speech impairment that are typically exhibited by Parkinson's patients. According to the National Institute of Neurological Disorders and Stroke, at least 1 million people suffer from Parkinson's Disease, and about 50,000 new cases are reported each year in the United States.

A highly conserved pre-synaptic protein, α-synuclein, has been implicated in the pathology of Parkinson's Disease. It is thought that conformational changes in α-synuclein lead to the proteinaceous accumulation and fibrillogenesis characteristic of this disease. See U.S. Pat. No. 7,045,290 (to Lindquist et al.). Current treatment options include levodopa and dopamine agonists. These drugs, however, only give temporary relief to the symptoms and have serious side effects if used in large amounts. Deprenyl, a monoamine oxidase B inhibitor, was the first drug suggested to provide causal treatment of Parkinson's Disease by alleviating symptoms and attenuating the progression of the disease, but the therapeutic efficacy of deprenyl is controversial. See U.S. Pat. No. 6,417,177 (to Nelson).

Huntington's Disease (HD) is a genetic neurological disorder, with symptoms of abnormal body movement and impaired mental abilities. Huntington's Disease is caused by a trinucleotide repeat expansion in the Huntingtin gene (htt), which in turn produces a mutant form of the htt protein having an pathological expansion of a polyglutamine (PolyQ) tract. The mutant htt protein misfolds and forms aggregates in the brain and other affected tissues, resulting in neuronal cell death (Wolfgang et al., *Proc Nat Acad Sci* 2005; 102: 11563-11568). Most of the drugs used to treat the symptoms of Huntington's Disease have side effects such as fatigue, restlessness, or hyperexcitability.

Alzheimer Disease (AD) is a progressive brain disease known generally as senile dementia. More than 4.5 million Americans have been diagnosed with AD, and this number is expected to triple in the next 40-50 years (Lyketsos et al., *Am J Geriatr Psychiatry* 2006; 14(7): 561-72).

It is believed that the pathophysiological root of Aβ lies, in part, in the misprocessing or mutation of the amyloid precursor protein. The misprocessed protein may produce an increased amount of amyloid beta peptides (Aβ) or variant forms thereof. The accumulation of Aβ leads to the deposition of insoluble Aβ plaques, and eventually to synaptic failure, neuronal injury, formation of tangles of hyperphosphorylated tau protein, and apoptotic neuronal death. The injury or death of neurons leads to the loss of multiple neurotransmitters, which in turn leads to the emergence of the cognitive and functional symptoms of the disease.

Currently available medications offer relatively small symptomatic benefit for some patients and do not slow disease progression. Therefore, various symptomatic strategies for treating or preventing AD are ongoing. For example, AD has been found to be associated with brain inflammation, and thus, nonsteroidal anti-inflammatory drugs such as ibuprofen and indomethacin have been used to lower risk of developing AD. However, the drugs have long-term risks of gastrointestinal bleeding and renal disease, and are associated with rare cardiovascular toxicity. An association of oxygen free radicals with AD has also raised the possibility of antioxidant therapy. The American Psychiatric Association and the American Academy of Neurology Treatment Guidelines for AD both recommend high-doses of vitamin E as a treatment option. This recommendation is tempered, however, by recent findings that vitamin E therapy did not delay progression of mild cognitive impairment associated with AD, and that vitamin E in very high doses increased mortality in older people. See Lyketsos et al., 2006, supra.

Another treatment option for AD is to reduce the naturally occurring degradation of acetylcholine by an enzyme known as acetylcholine esterase (AChE) Inhibition of AChE leads to increased acetylcholine levels. The U.S. Food and Drug Administration has approved four cholinesterase inhibitors drugs for the treatment for Aβ: tacrine, donepezil, rivastigmine, and galanthamine. Short-term (up to 6 months) clinical trials of the cholinesterase inhibitors showed that these drugs improved or slowed cognitive losses associated with AD, but clinical trial results on their long-term benefits are not conclusive. In very mild or more severe AD, the benefits of cholinesterase inhibitors are less substantiated. See Lyketsos et al., 2006, supra.

Treatments of AD that target removing Aβ from the brain are under development. For example, U.S. Pat. No. 7,262,223 (to Kong et al.) describes the use of amidine compounds in the treatment of amyloid-related diseases; U.S. Pat. No. 7,279,501 (to Kim) describes the use of natural product compounds isolated from plants (e.g., turmeric, gingko biloba, and ginger) and their synthetic chemical analogues for the treatment of an Aβ-induced disease. Recent evidence suggests that moderate consumption of red wine may reduce the incidence of AD and may attenuate AD-type cognitive deterioration and amyloid neuropathology (Dartigues et al., *Therapie* 1993; 48: 185-187; Dorozynski, *BMJ* 1997; 314: 997; Luchsinger et al., *J Am Geriatr Soc* 2004; 52: 540-546). Accumulation of soluble extracellular high molecular weight (HMW) oligomeric Aβ species in the brain is considered a major risk factor for the onset and progression of cognitive deterioration (Klyubin et al., *Nat Med* 2005; 11: 556-561; Selkoe, *J Alzheimer's Dis* 2001; 3: 75-80). It has also been suggested that grape-derived polyphenolic compounds may inhibit oligomerization of Aβ in vitro (Porat et al., *Chem Biol Drug Des* 2006; 67: 27-37). However, studies to date were limited to in vitro testing.

Many types of neurodegenerative diseases are linked with abnormal protein folding, accumulation, aggregation, and/or deposition of proteins. For example, there are two types of abnormal protein deposits in the brains of Alzheimer's patients. There are amyloid plaques composed of amyloid beta peptides that are deposited extracellularly in the brain parenchyma and around the cerebral vessel walls, and there are neurofibrillary tangles that are composed of aggregates of hyperphosphorylated tau protein located in the cytoplasm of degenerating neurons. In patients with Parkinson's Disease, Lewy bodies are observed in the cytoplasm of neurons of the substantia nigra. The major constituents of Lewy bodies are fragments of a protein named α-synuclein. In patients with Huntington's disease, intranuclear deposits of a polyglutamine-rich version of the mutant Huntingtin protein are a typical feature of the brain. Patients with hereditary Amyotrophic Lateral Sclerosis have aggregates primarily composed of superoxide dismutase in cell bodies and axons of motor neurons. Additionally, diverse forms of transmissible spongiform encephalopathy are characterized by accumulations of protease-resistant aggregates of the prion protein.

Evidence from biochemical, genetic, and neuropathological studies suggests an active involvement of protein misfolding and/or aggregation in the pathology of neurodegenerative diseases. For example, the presence of abnormal aggregates usually occurs in the brain regions mostly damaged by the disease. Mutations in the gene encoding the misfolded protein produce inherited forms of the disease, which usually have an earlier onset and more severe phenotype than the sporadic forms. Transgenic animals expressing the human mutant gene for the misfolded protein develop some of the typical neuropathological and clinical characteristics of the human disease. Also, misfolded protein aggregates produced in vitro are neurotoxic and induce cell death.

Tauopathies are a family of neurodegenerative diseases that implicate malfunction of tau proteins (a family of closely related intracellular microtubule-associated proteins). These neurodegenerative diseases include, for example, Alzheimer's disease, Progressive Supranuclear Palsy, Corticobasal Degeneration, Argyrophilic Grain Disease, Pick's Disease, as well as others. Common features among tauopathies are abnormal hyperphosphorylation of tau and accumulations of tau into detergent-resistant intracellular inclusions known as neurofibrillary tangles (NFTs) among neurons or glial cells in the brain. Abnormally hyperphosphorylated tau proteins are readily dissociated from microtubules and aggregated into oligomeric tau paired helical filaments that are ultimately deposited as intracellular NFTs. (Mi, K. et al., *Curr Alzheimer Res* 2006; 3: 449-463). The formation of oligomers serves as nucleation sites that sequester additional hyperphosphorylated tau as well as normal non-phosphorylated tau into fibrillary aggregates. (Sorrentino et al., *Neurol Sci* 2007; 28: 63-71). Thus, a theory of tau-mediated neurodegeneration is based on a "toxic gain of function" model, in which abnormally phosphorylated tau proteins promote removal of both hyperphosphorylated and normal tau proteins from microtubules. This leads to microtubule instability and alterations of microtubule-mediated processes such as axonal transport, which in turn leads to impaired function and reduced viability of neuronal and glial cells in the brain (Sorrentino et al., 2007, supra).

U.S. Patent Application Publication No. 2007/0122504 (to Moon et al.) discloses a process of manufacturing a grape seed extract and methods of using such grape seed extract to treat neurodegenerative diseases, including AD. The extract is prepared by (1) extracting the grape seed in an alkaline solution having a pH of 8 to 11, at preferably 20-50° C. to obtain alkaline soluble substance; (2) neutralizing with acidic solution to adjust to the pH ranging from 2 to 4, and centrifuging the resulting solution and obtaining precipitated layer; (3) adding lower alcohol and obtaining the supernatant layer, then concentrating the supernatant layer; and (4) adding non-polar solvent and removing non-polar solvent soluble layer to obtain purified fraction and subjecting to repeated purification and lyophilzation to obtain dried grape seed extract. (See Moon, paragraphs [0030]-[0035]).

Due to the prevalence of neurodegenerative disease and the lack of proven effective pharmaceutical compositions or methods to treat symptoms associated with the neurodegenerative diseases, there is still a need for improved pharmaceutical compositions and methods for treatment and prevention thereof.

SUMMARY OF THE INVENTION

The present invention is directed to a method of treating a neurodegenerative disease of a subject through the administration of a pharmaceutical composition to a subject in need thereof, wherein the pharmaceutical composition comprises a grape seed extract or one or more compounds derived therefrom. In certain embodiments, the pharmaceutical composition may also contain an active ingredient selected from the group consisting of an antioxidant, an acetylcholine esterase inhibitor, and combinations thereof. In a particular embodiment, the grape seed extract comprises less than about 12% by weight of galloylated proanthocyanidin based on the total weight of proanthocyanidins in the extract.

The methods of the present invention are used to treat, ameliorate, reduce the risk of or prevent a neurodegenerative disease such as Alzheimer's Disease, Parkinson's Disease, Huntington's Disease, and/or a tauopathy. The various tauopathies contemplated by the invention include Alzheimer's Disease, Progressive Supranuclear Palsy, Corticobasal Degeneration, Argyrophilic Grain Disease, Pick's Disease, and familial fronto-temporal dementia.

In one embodiment, the pharmaceutical composition is administered orally. The oral dosage forms include powder, tablet, capsule, orodispersible tablet, soft capsule, aqueous medicine, syrup, elixir, or sachet. In another embodiment, the pharmaceutical composition is administered transdermally. In a different embodiment, the pharmaceutical composition is administered transnasally.

In particular embodiments, the subject is a human subject. The frequency of administration is monthly, biweekly, weekly, or daily, and may be administered in a single dose or in divided doses. The effective amount of the compounds of the grape seed extract is a dosage from about 100 to about 1000 mg per day, preferably from about 200 to about 600 mg per day.

BRIEF DESCRIPTION OF THE DRAWINGS

FIG. 1 illustrates the result of component analysis of a grape seed extract (GSE) product, MegaNatural®-AZ (or MNG-AZ). FIG. 1A illustrates the molecular structure of a typical heteropolymeric proanthocyanidin. FIG. 1B represents a normal phase HPLC analysis of MNG-AZ. FIG. 1C schematically presents a homotetrameric proanthocyanidin comprised of epicatechin gallate (left panel) and the resultant degalloylated proanthocyanidin plus an isolated gallic acid structure (right panel). FIG. 1D shows the percentage of galloylated proanthocyanidins (out of total proanthocyanidins) in MNG-AZ compared to four other commercially available GSE preparations: MegaNatural®-Gold, GSE Brand A, GSE Brand B and GSE Brand C (FIG. 1D) (Brand A is "Activin", a GSE obtained from San Joaquin Valley Concentrates; Brand B is "Masquelier® OPC", a GSE from France; and Brand C is a GSE from Indena S.p.A., Italy). FIGS. 1E and 1F present the levels of galloylated proanthocyanidin in MNG-AZ and some other commercially available GSEs.

FIGS. 2A-2D. FIGS. 2A and 2B shows the sodium dodecyl sulfate polyacrylamide gel electrophoresis (SDS-PAGE) of incubation product of $A\beta_{1-42}$ (2A) and $A\beta_{1-40}$ (2B) with various amounts of MNG-AZ GSE. FIGS. 2C and 2D demonstrate the result of SDS-PAGE of $A\beta_{1-42}$ (2C) and $A\beta_{1-40}$ (2D) in the presence or absence of MNG-AZ GSE following Photo-Induced Cross-linking of Unmodified Proteins (PI-CUP) chemistry.

FIGS. 3A-3D. FIGS. 3A and 3C show the CD spectra of untreated $A\beta_{1-40}$ and $A\beta_{1-42}$, respectively; FIGS. 3B and 3D show the CD spectra of MNG-AZ treated $A\beta_{1-40}$ and $A\beta_{1-42}$, respectively. Spectra were acquired immediately at the start of the incubation period (- - - -) and after 2 (– - - –), 3 (– - –), 6 (– – –), and 7 (——) days. The spectra presented at each time are representative of those obtained during each of 3 independent experiments.

FIGS. 4A-4D. FIGS. 4A and 4C show the fluorescence spectra of untreated $A\beta_{1-40}$ and $A\beta_{1-42}$, at different concentrations of a control compound Med1, respectively; FIGS. 4B and 4D show the fluorescence spectra of MNG-AZ treated $A\beta_{1-40}$ and $A\beta_{1-42}$, respectively. The concentrations of Med1 (or MNG-AZ) are 0 (♦), 5 (■), or 25 (▲) μM in each FIGS. 4A-4D.

FIGS. 5A-5F. FIGS. 5A and 5B show exemplary morphologies of untreated $A\beta_{1-40}$ and $A\beta_{1-42}$, respectively. FIGS. 5C and 5E show morphologies of $A\beta_{1-40}$, in the presence of the lower (5 μM) and higher (25 μM) MNG-AZ concentrations, respectively. FIGS. 5D and 5F show morphologies of $A\beta_{1-42}$, in the presence of the lower (5 μM) and higher (25 μM) MNG-AZ concentration, respectively.

FIG. 6 illustrates Aβ inhibiting effect of MNG-AZ as investigated by MTT metabolism. FIGS. 6A (and 6C) shows the toxicity of low molecular weight $A\beta_{1-40}$ (and $A\beta_{1-42}$) and the effect of MNG-AZ in reducing the toxicity. FIGS. 6B (and 6D) shows the toxicity of $A\beta_{1-40}$ aggregation (and $A\beta_{1-42}$ aggregation) and the effect of MNG-AZ in reducing the toxicity.

FIG. 7 illustrates the effects of MNG-AZ GSE on the neuropathology of Tg2576 mice. FIGS. 7A-7B show the effects of MNG-AZ GSE on body weight (7A) or liquid consumption (7B). FIGS. 7C-7D present assessments of soluble, extracellular HMW-Aβ peptide contents in the brain of Tg2576 mice. FIG. 7E shows an assessment of $A\beta_{1-42}$ and $A\beta_{1-40}$ peptide concentrations in the brain of MNG-AZ GSE treated and control mice. FIG. 7F shows a stereological assessment of cerebral cortex and hippocampal formation Aβ-amyloid plaque burden in MNG-AZ GSE treated and control mice. FIG. 7G illustrates an assessment of $A\beta_{1-42}$ and $A\beta_{1-40}$ peptide concentrations in the brain of MegaNatural®-Gold treated and control mice.

FIGS. 8A-8F. FIG. 8A illustrates a western analysis of total APP expression in Tg2576 mice treated for about 5 months with MNG-AZ. FIG. 8B illustrates an assessment of α-, β-, and γ-secretase activity. FIG. 8C illustrates a western analysis of soluble $APP_\alpha$ and $APP_\beta$ expression in Tg2576 mice treated with MNG-AZ GSE vs. control group. FIGS. 8D and 8E show the expression of Aβ degradation enzyme neprilysin and insulin degrading enzyme in the brain of Tg2576 mice treated with MNG-AZ GSE vs. the control mice. FIG. 8F illustrates an assessment of serum $A\beta_{1-40}$ (left panel) and $A\beta_{1-42}$ (right panel) content by Enzyme-Linked ImmunoSorbent Assay (ELISA).

FIGS. 9A-9C. FIGS. 9A and 9B show the influence of MNG-AZ GSE on Aβ related spatial memory in Tg2576 mice as determined by Morris water maze tests. FIG. 9C presents an assessment of soluble, extracellular high molecular weight Aβ peptide content in the brain of Tg2576 mice.

FIGS. 10A and 10B illustrate the effect of MNG-AZ GSE treatment on the cognitive function in strain-, age- and gender-matched wild type animals as measured by Morris water maze tests.

FIGS. 11A-11B. FIG. 11A shows the time-dependent ThS-fluorescence spectra of aggregated tau at various concentrations of MNG-AZ; FIG. 11B shows maximum accumulation of tau aggregates at various concentrations of MNG-AZ.

FIGS. 12A-12B. FIG. 12A shows the time-dependent ThS-fluorescence spectra of aggregated tau at various concentrations of MNG-AZ; FIG. 12B shows the rates of dissociation of tau aggregates as a function of the concentrations of MNG-AZ.

FIGS. 13A-13D. FIG. 13A shows the eye development result of the *Drosophila* in the absence of the GSE; FIG. 13B shows the eye development result of the *Drosophila* in the presence of the GSE; FIG. 13C presents the visual scoring of male *Drosophila* eyes in a representative experiment (in the presence and absence of the GSE); FIG. 13D shows the number of absent eyes in the same trial as in FIG. 13C.

FIG. 14 illustrates the percentage of survival over days in *Drosophila* model of Huntington's Disease. The open circles represent results from the group treated with a grape seed extract, and the shaded circles represent results from the control group.

FIGS. 15A-15C. FIG. 15A presents the results for Aβ$_{1-40}$; FIG. 15B presents the results for Aβ$_{1-42}$; FIG. 15C presents the results for glutathione S-transferase. Lanes 1: molecular weight markers; Lanes 2: protein alone, without cross-linking; Lanes 3: protein alone; Lanes 4: protein plus Med1 (25 µM); Lanes 5: protein plus Med1 (250 µM); Lanes 6: protein plus MNG-AZ (25 µM); Lanes 7: protein plus MNG-AZ (250 µM). The gel is representative of each of three independent experiments.

FIG. 16 illustrates the effect of MNG-AZ GSE on tau peptide aggregation using PICUP assay. The gel shows a representative analysis of 25 µM tau peptide cross-linked in the presence (lanes 2, 4, 6, 8) or absence (lanes 1, 3, 5, 7) of equal molar (25 µM) of the GSE. Due to expected ineffective staining of small peptides, monomeric tau peptides are not detectable in this experiment. The ~2.1 and ~3.5 kDa kDa bands correspond to, respectively, trimeric and pentameric tau peptide aggregates. CTR: non-cross-linked tau peptide; lanes 1-8: tau peptide with ammonium persulfate (APS) and 1× (lanes 1, 2), 2× (lanes 3, 4), 3× (lane 5, 6) and 4× (lanes 7, 8) Ru(Bpy).

FIGS. 17A and 17B.

FIGS. 18A and 18B.

FIGS. 19A-19D. FIG. 19A depicts electron micrograph of purified PHFs in the absence of MNG-AZ GSE; FIGS. 19B and 19C depict electron micrographs of purified PHFs in the presence of 100 µM MNG-AZ GSE for 5 sec (FIG. 19B) or 1 h (FIG. 19C). In FIGS. 19A and 19C, electron-dense particles represent pSer214tau labeling (arrows in C). FIG. 19D depicts a quantitative analysis of GSE treatment on PHFs as a function of treatment time (5 to 60 min), wherein bar graph represents average maximal width with the standard deviation; the numbers of PHFs measured are presented in parentheses. Statistical analysis by one-way ANOVA (P<0.0001), followed by Bonferroni's Multiple Comparison Test, **p<0.001 compared to non-treated PHFs (0-time).

FIGS. 20A-20D. FIG. 20A depicts electron micrograph of native PHFs isolated from AD brain not incubated with trypsin; FIG. 20B depicts electron micrograph of PHFs pre-treated with MNG-AZ (100 µM, 1 h) not incubated with trypsin; FIG. 20C depicts electron micrograph of native PHFs incubated with trypsin (1 µg/ml, 10 min); FIG. 20D depicts electron micrograph of PHFs pre-treated with MNG-AZ (100 µM, 1 h) and incubated with trypsin (1 µg/ml, 10 min).

FIGS. 21A-21G. FIGS. 21A and 21D depict representative eye phenotypes in wild-type flies; FIGS. 21B and 21E show eyes of R406W mutant tau flies in the absence of a GSE treatment; FIGS. 21C and 21F show eyes of R406W mutant tau flies treated with MNG-AZ; FIG. 21G shows quantitative analysis of adult eye morphology, using a four-point scoring system (where 0=no eye and 4=normal eye) in male and female flies across three independent trials. The number of flies scored per trial is indicated. Bar graphs represent mean+SEM.

FIGS. 22A-22D.

FIGS. 23A and 23B. FIG. 23A shows motor impairment of JNPL3 mice at the age of 5 months and 13 months, respectively, when treated with the GSE, as compared to those not treated with the GSE. FIG. 23B shows the mortality rate comparison between the JNPL3 mice treated and not treated with the GSE, wherein line graphs represent % survival over time.

FIGS. 24A and 24B. FIG. 24A shows images of vehicle-treated control (Ctrl) cells and cells treated with 12.5 µM and 25 µM GSE following muristerone A induction. FIG. 24B shows a Western blot analysis of aggregations of GFP-Htt fusion protein aggregation into high molecular weight aggregates in the absence (Ctrl) or presence of 12.5 µM and 25 µM GSE treatments (left panel: western blot probed with anti-GFP antibody to identify aggregation of the GFP-Htt fusion protein into higher molecular species; right panel: densitometric analysis of the western blot showing the distribution of the GFP-Htt protein and higher molecular weight htt aggregates).

FIGS. 25A and 25B. FIGS. 25A and 25B illustrates the climbing assay result on day 9 and on day 16, respectively. Three independent climbing trials were conducted on each testing day. Bar graphs represent mean+SEM of the % of the flies that successfully accomplish the climbing tasks. Statistical analysis by Student's t-test, ** p<0.001 comparing GSE-treated to untreated groups.

FIG. 26 illustrates the percentage of survival over days in a *Drosophila* model of HD. The shaded inverted triangles represent results from the group treated with MNG-AZ GSE, and the shaded diamonds represent results from the control group. The data represent results from 4 independent trials.

FIG. 27 illustrates the effect of a GSE treatment on motor impairment in a HD mouse model, assessed using a rotarod assay at different weeks of ages. The data represent results obtained from 3 independent trials.

FIG. 28 illustrates the effect of a GSE treatment on the mortality of a HD mouse model. Line graphs represent % survival over time.

DETAILED DESCRIPTION

Figures 1A, 1B:
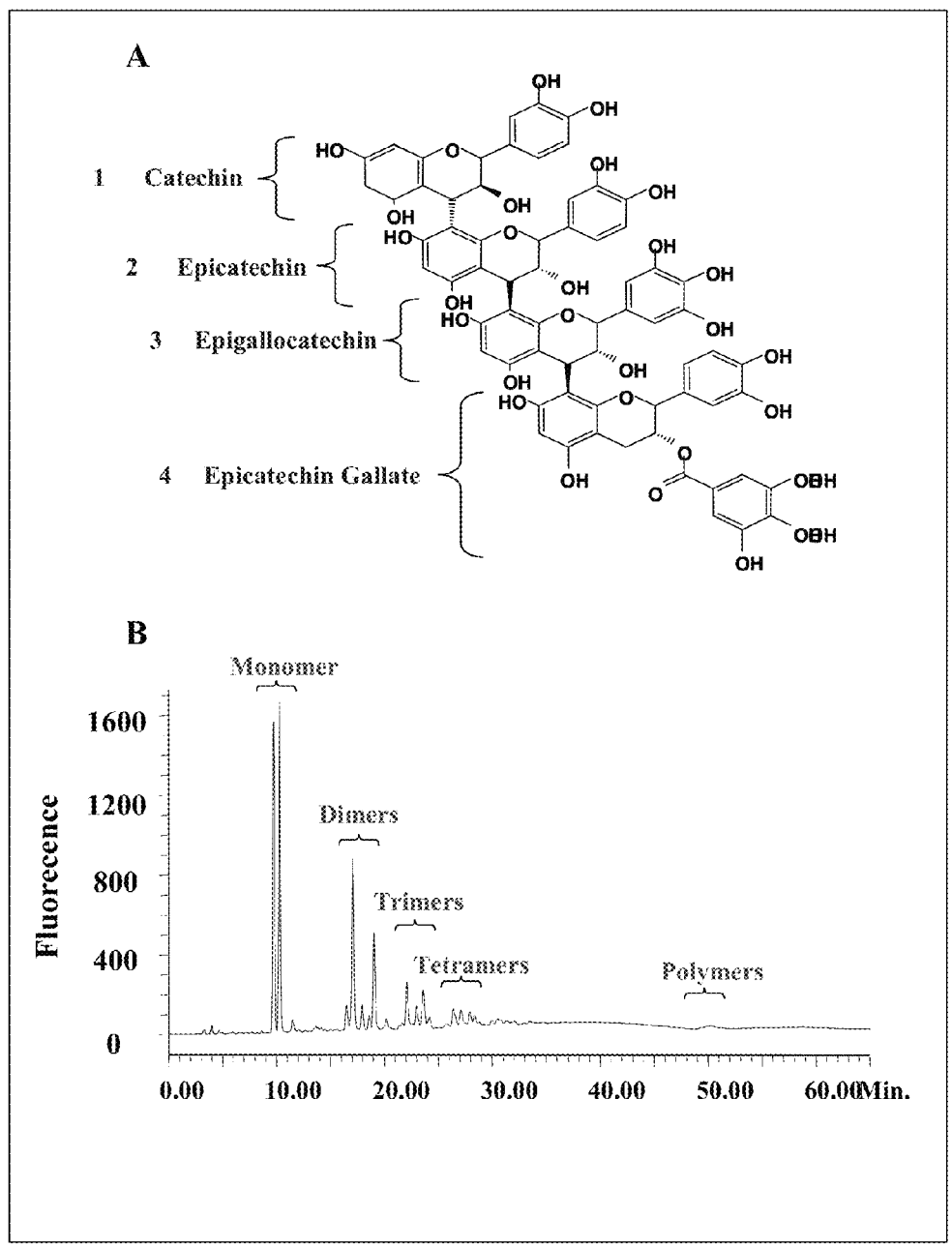
FIGS. 1A-1F.

The present invention advantageously provides for a method of reducing the misfolding, accumulation, aggregation or deposition of Aβ, oligomeric Aβ, tau proteins or other proteins associated with a neurodegenerative disease. The method involves administering an effective amount of a pharmaceutical composition comprising a grape seed extract or one or more compound derived therefrom. These and other aspects of the invention are discussed in detail in the description and Examples provided below.

The present invention is based upon the discovery that compounds from a grape seed extract function as efficient inhibitors against misfolding, accumulation, aggregation and/or deposition of Aβ, tau protein, and other proteins that are associated with various neurodegenerative diseases. Specifically, the invention is based in part on the discovery that specific types of grape seed extract reduced or inhibited (1) the formation of oligomers of synthetic $A\beta_{1-40}$ (Aβ40) and $A\beta_{1-42}$ (Aβ42) in vitro; (2) the amount of oligomeric Aβ in the brains of Tg2576 mice (transgenic mice expressing mutant amyloid precursor protein and exhibiting AD-type cognitive deterioration), and appreciably improved or slowed the loss of cognitive function of Tg2576 mice (as compared to untreated mice); (3) the initiation of nucleation leading to tau aggregates into structures characterized by paired helical filament as found in various tauopathies, as well as the stability of the tau aggregates, in vitro; (4) the harmful effects of a tau protein in a transgenic R406W Drosophila phenotype, as well as the harmful effects of a tau protein in a transgenic JNPL3 mouse model, in vivo, (5) aggregation of a polyglutamine-containing htt protein species in vitro; (6) the harmful effects of a mutant htt protein in a transgenic elav>Q93httexon1 Drosophila phenotype, as well as the harmful effects of a mutant htt protein in a transgenic R6/2 mouse model, in vivo. These observations surprisingly demonstrate that a grape seed extract or the compounds derived therefrom can be used to reduce the development of amyloid, htt, and tau-related neuropathology.

Accordingly, the present invention provides pharmaceutical compositions comprising a grape seed extract or one or more compounds derived therefrom, and methods of using such pharmaceutical compositions to treat or prevent the neuropathological features of a neurodegenerative disease, such as neurodegeneration, cellular toxicity, cognitive impairment or deterioration, and motor deterioration. Preferably the grape seed extract is characterized by having less than about 12% by weight of galloylated proanthocyanidins based on the total amount of proanthocyanidins.

The terms used in this specification generally have their ordinary meanings in the art, within the context of this invention and in the specific context where each term is used. Certain terms are defined below to provide additional guidance in describing the compositions and methods of the invention.

DEFINITIONS

The term "dementia" refers to a clinical syndrome associated with a global cognitive decline of memory and other areas of cognition.

The term "degenerative disease" refers to a disease in which the function or structure of the affected tissues or organs progressively deteriorates over time, as contrasted to infectious diseases.

The term "neurodegenerative disease" refers to a condition or disorder in which neuronal cells are lost due to cell death.

The term "Alzheimer's Disease" (or "senile dementia") refers to a mental deterioration associated with specific degenerative brain disease that is characterized by senile plaques, neuritic tangles, and progressive neuronal loss.

The term "Parkinson's Disease" is a chronic and progressive degenerative disorder of the central nervous system that often impairs motor skills and speech. Parkinson's Disease belongs to a group of conditions called movement disorders and is characterized by muscle rigidity, tremor, a slowing of physical movement and, in extreme cases, a loss of physical movement.

The term "Huntington's Disease" refers to an inherited neurological disorder caused by a trinucleotide repeat expansion in the gene coding for Huntingtin protein. The symptoms of Huntington's Disease include abnormal body movements and lack of coordination.

The term "tauopathy" refers to a family of neurodegenerative diseases that implicate malfunction of tau proteins (a family of closely related intracellular microtubule-associated proteins). These neurodegenerative diseases (tauopathies) include, for example, Alzheimer's disease, Progressive Supranuclear Palsy, Corticobasal Degeneration, Argyrophilic Grain Disease, Pick's Disease, and familial fronto-temporal dementia.

The term "amyloid beta" (Aβ) refers to a peptide produced by cleavage of amyloid beta precursor protein (APP), the accumulation and deposition of which forms plaques in the brain of a subject. The most common isoforms of Aβ are $A\beta_{1-40}$ (Aβ40) and $A\beta_{1-42}$ (Aβ42). The phrase "oligomer of Aβ" refers to a peptide having more than one Aβ units linked by chemical bonds, or a multitude of Aβ peptides linked by chemical bonds and/or associated by physical forces. The term "oligomerization" refers to the combining or assembly of multiple smaller chemical or biological molecules, such as Aβ, into a larger collection through chemical linking and/or physical association.

The term "reduce" refers to a diminishing or lowering of an amount or concentration of a chemical or biological substance, or to slow down or reverse a chemical or physical process that is ongoing.

The term "accumulation" refers to the increase in concentration or amount of a chemical or biological substance, such as a peptide, in a specified area or space.

The term "aggregation" refers to the combining or assembly of multiple smaller chemical or biological molecules, or a collection thereof, into a larger collection through chemical linking and/or physical association.

The term "deposition" refers to attachment of a chemical or biological substance to a biological surface, such as a cell membrane or a blood vessel wall.

The term "polyphenol" or "polyphenolic compound" refers to a compound characterized by the presence of more than one phenol group per molecule.

The terms "therapeutically effective dose" or "therapeutically effective amount", or "effective amount" refer to the amounts of grape seed extract or the compounds contained therein that is sufficient to result in a therapeutic response. A therapeutic response may be any response that a user (e.g., a clinician) will recognize as an effective response to the therapy, such as by assessing symptoms and surrogate clinical markers. Thus, a therapeutic response will generally be an amelioration of one or more symptoms of a disease or disorder.

The phrase "pharmaceutically acceptable" refers to molecular entities and compositions that are physiologically tolerable and do not typically produce untoward reactions when administered to a human. Preferably, as used herein, the term "pharmaceutically acceptable" means approved by a regulatory agency of the federal or a state government or listed in the U.S. Pharmacopeia or other generally recognized pharmacopeia for use in animals, and more particularly in humans.

The phrase "pharmaceutically acceptable salts" refers to derivatives of compounds modified by making acid or base salts thereof. Examples of pharmaceutically acceptable salts include mineral or organic acid salts of basic residues such as amines; and alkali or organic salts of acidic residues such as carboxylic acids. Pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, and nitric acid; and the salts prepared from organic acids such as acetic, propionic, succinic, glycolic, stearic, lactic, malic, tartaric, citric, ascorbic, palmoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic acid. Pharmaceutically acceptable salts may be synthesized from the parent compound which contains a basic or acidic moiety by conventional chemical methods. Generally, such salts may be prepared by reacting the free acid or base forms of these compounds with a stoichiometric amount of the appropriate base or acid in water or in an organic solvent, or in a mixture of the two.

The term "carrier" or "pharmaceutical carrier" refer to a diluent, adjuvant, excipient, or vehicle with which the compound is administered. Such pharmaceutical carriers can be sterile liquids, such as water and oils. Water or aqueous solution saline solutions and aqueous dextrose and glycerol solutions are preferably employed as carriers. Suitable pharmaceutical carriers are described in "Remington's Pharmaceutical Sciences" by E. W. Martin, 18$^{th}$ Edition, or other editions.

The term "antioxidant" refers to a series of chemical substances capable of inhibiting or neutralizing hazardous free radicals within the body of a subject.

The term "subject" includes living organisms in which misfolding, accumulation, aggregation or deposition of amyloid beta, oligomer of amyloid beta, tau protein, or other proteins can occur. The term "mammal" refers to any organism of the Class Mammalia of higher vertebrates that nourish their young with milk secreted by mammary glands, e.g., mouse, rat, rabbit, dog, cat, and, in particular, human. The term "human" refers to a member of the species Homo Sapiens. The term "patient" refers to a human subject to whom treatment with the compositions according to the present invention is provided.

The term "treat" refers to the administration of a composition of the present invention to a subject for the purposes of attenuating, slowing progression, delaying or reversing a condition and/or one or more symptoms associated with a neurodegenerative disease and/or the misfolding, accumulation, aggregation or deposition of proteins including but not limited to amyloid beta, oligomer of amyloid beta, tau proteins, α-synuclein, etc.

The term "prevent" refers to the administration of the compositions of the present invention to a subject prior to the onset of a condition or a symptom associated with the misfolding, accumulation, aggregation or deposition of amyloid beta, oligomer of amyloid beta, tau proteins or other proteins so as to keep the condition or the symptom from occurring.

The term "reduce the risk" of a condition or symptom from occurring in a subject means that the likelihood of the subject to develop the condition or symptom is less than that of a comparable control individual, for example where the subject is administered a pharmaceutical composition of the invention and the control is untreated or receives a placebo.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

Pharmaceutical Compositions

Grape Seed Extract

One aspect of the present invention is directed to the use of pharmaceutical compositions derived from grape seed extract to treat or prevent neurodegenerative diseases associated with misfolding, accumulation, aggregation, and/or deposition of proteins. As used herein, the term grape seed extract (GSE) refers to the material or one or more compounds that are extracted from grape seeds, skin or pomace.

Grape seed extract can be obtained from various sources. For example, Polyphenolics (a division of Constellation Wines U.S., Inc.) markets a series of grape seed extract products under the trademark MegaNatural®. Examples of commercial MegaNatural® products include MegaNatural® GSKE Grape Pomace Extract, MegaNatural®-BP, and MegaNatural®-Gold. Grape seed extract can also be prepared according to some specific extraction and/or purification procedures. For example, a grape seed extract can be obtained by using a process described in U.S. Pat. No. 6,544,581 (to Shrikhande et al., the '581 patent), or U.S. Patent Application Publication 2007/0071871 (to Shrikhande et al.), the disclosures of which are incorporated herein by reference in their entirety.

MegaNatural®-AZ (or MNG-AZ), which is experimental and not commercially available, has unique features which allow it to be readily absorbed through the intestinal mucosa due to removal of the gallate moiety from the constituent polyphenols. In the manufacturing process for MNG-AZ, the crude polyphenolic extract is subjected to mixed culture yeast fermentation for a duration of time to hydrolyze the gallic acid from gallated monomers and proanthocyanidin oligomers. The extract is further processed to a powder form containing greater than 90% by weight polyphenols and greater than 3% gallic acid by weight (see '581 patent). The yeast culture is selected for tannase activity for releasing gallic acid from the grape seed monomers and polymers. Alternatively, crude tannase enzymes can be prepared by fermentation process using yeast and molds and can be added to crude grape seed extract to release gallic acid. The resulting MNG-AZ is characterized by having less than about 12% by weight of galloylated proanthocyanidins based on the total amount of proanthocyanidins. While not being bound by any particular theory, it is believed that the removal of gallic acid side groups significantly increases the bioavailability of MNG-AZ.

Polyphenols, an important family of compounds in grape seed extract, are recognized to be effective antioxidants. Proanthocyanidins, a subclass of polyphenols, are polymeric compounds derived from catechin and epicatechin base units and their respective derivatives (e.g., epicatechin gallate in which epicatechin is modified with the addition of a gallic acid). A component analysis result of the grape seed extract MNG-AZ is illustrated in FIG. 1. The molecular structure of a typical heteropolymeric proanthocyanidin comprises catechin, epicatechin, epigallocatechin and derivatives of thereof (epigallocatechin and epicatechin gallate) (FIG. 1A). A normal phase HPLC analysis of MNG-AZ also indicates the presence of monomeric and polymeric units of proanthocyanidins (FIG. 1B).

Figure 1C:
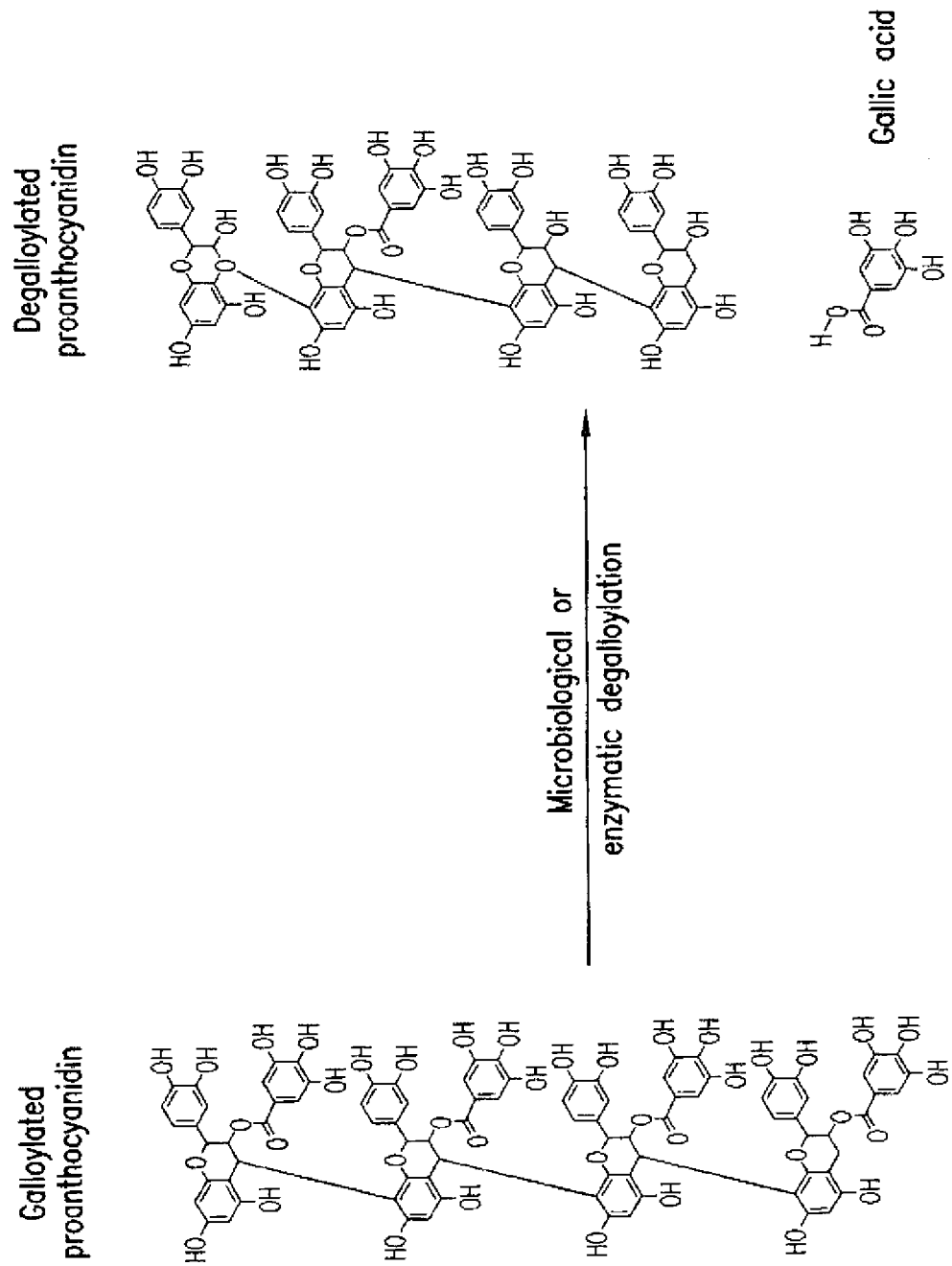
Figures 1D, 1E, 1F:
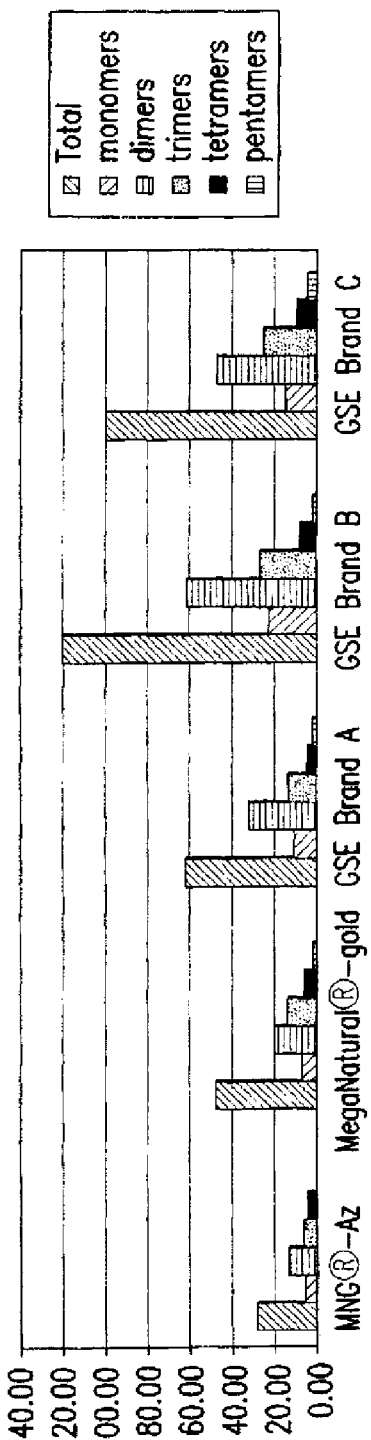

Proanthocyanidins containing epicatechin gallate can be degalloylated by microbiological or enzymatic conversion (FIG. 1C). This removal of the gallic acid side chains contributes to a major distinction between MNG-AZ and other commercially available grape seed extracts. MNG-AZ contains few to no gallic acid side chains, as illustrated by the percentage of galloylated proanthocyanidins (out of total proanthocyanidins) in MNG-AZ as compared to four other commercially available GSE preparations (FIGS. 1E and 1F). In the present invention, MNG-AZ is shown to have surprising bioactivity in vivo with respect to Aβ and tau-related neurodegenerative diseases in animal disease models.

In a specific embodiment of the present invention, the pharmaceutical composition comprises a specific grape seed extract, namely MegaNatural®-AZ. The pharmaceutical composition of the present invention may also comprise one or more compounds derived from a grape seed extract. The one or more compounds may include, but are not limited to, one or more polyphenols, one or more proanthocyanidins, or mixtures thereof. Exemplary polyphenols include, but are not limited to, monomeric catechin and epicatechin base units.

In other embodiments, the composition of the present invention further comprises a carrier. It is preferable that said carrier is used as an appropriate substance according to the usage and application method. For example, for oral administration, the appropriate pharmaceutical carriers of the present invention include, but are not limited to, lactose, dextrose, sucrose, sorbitol, mannitol, starch, gum acacia, xylitol, erythritol, alginate, gelatin, calcium phosphate, calcium silicate, cellulose, methyl cellulose, polyvinyl pyrrolidone, water, methylhydroxy benzoate, propylhydroxy benzoate, magnesium stearate and mineral oil. The composition may additionally include fillers, anti-agglutinating agents, lubricating agents, wetting agents, flavoring agents, emulsifiers, preservatives and the like.

The pharmaceutical composition of the present invention may be prepared as an oral form including but not limited to a powder, tablet, capsule, orodispersible tablet, soft capsule, aqueous medicine, syrup, elixir, and a sachet.

Alternatively, the pharmaceutical composition may be administered transdermally. The compositions of the present invention may be applied directly to the skin or indirectly though a transdermal device. The compositions of the present invention can be prepared as direct transdermal dosage forms such as a gel, cream, lotion, emulsion, oil, ointment, suspension, aerosol, spray, or the like. The compositions of the present invention can be prepared as an indirect transdermal dosage form as a component of a transdermal device including a patch, bandage, tape, or other occlusive dressing. Additionally, the pharmaceutical composition may be administered transnasally, for example as a transnasal spray. Other passive or active transdermal devices for absorption through the skin or mucosal surface are also contemplated.

The appropriate pharmaceutical carriers for transdermal administration of the compositions of the present invention can be any pharmaceutically acceptable carrier material suitable for transdermal drug administration. Such carriers include materials known in the art, such as a liquid, gel solvent, liquid diluent, solubilizer, or the like. The appropriate carriers are nontoxic and do not interact with other components of the composition in a deleterious manner. Examples of suitable carriers for use herein include water, silicone, liquid sugars, waxes, petroleum jelly. The carriers may also include stabilizers, adjuvants, penetration enhancers, or other types of additives useful for facilitating transdermal drug delivery.

In certain embodiments, where applicable, the compounds of the present invention may be used in the form of their pharmaceutically acceptable salts, and also may be used alone or in appropriate association, as well as in combination with other pharmaceutically active compounds. In specific embodiments, the composition of the present invention may additionally comprise an antioxidant and/or a cholinesterase inhibitor.

Methods of Treatment

The pharmaceutical composition of the present invention can be administered to a subject having a risk factor or condition associated with neurodegenerative diseases. The subject can be a human, or a lower mammal, including but not limited to a cat, a dog, a rat, a mouse, a sheep, a goat, a cow, a monkey, a chimpanzee, and transgenic species thereof. The pharmaceutical composition is administered to the subject in a therapeutically effective amount, in such amounts and for such time as is necessary to achieve the desired results. The neurodegenerative diseases contemplated herein are generally characterized by increased levels of one or more proteins or peptides in a subject's brain, including their misfolding, accumulation, aggregation, and/or deposition thereof. These diseases include, but are not limited to, Alzheimer' Disease, Parkinson's Disease, Amyotrophic Lateral Sclerosis, Huntington's Disease, Fronto-Temporal Dementia, and Cortico Basal Degeneration, and/or a tauopathy. The tauopathy can be Alzheimer's Disease, Progressive Supranuclear Palsy, Corticobasal Degeneration, Argyrophilic Grain Disease, Pick's Disease, and familial fronto-temporal dementia, among others.

As used herein, the one or more proteins (or, used interchangeably with "peptides") targeted in the methods of treatment of the present invention refer to molecules consisting of multiple amino acid units connected by peptide bonds, wherein the molecules are associated with one or more neurodegenerative diseases as described. The proteins include both wild-type, mutant, transgenic, and synthetic proteins. For example, they can include, but are not limited to, specific proteins associated with specific neurodegenerative diseases. For example, an amyloid beta protein (e.g., $A\beta_{1-40}$, $A\beta_{1-42}$) and/or a neurofibrillary tangle is/are the target protein(s) in patients with Alzheimer's Disease. Also, a mutant htt protein is the target protein in patients with Huntington's Disease. α-synuclein protein is the target protein in patients with Parkinson's Disease, and a tau protein is the target in patients with a Tauopathy.

In addition, it is contemplated that the methods for treatment in accordance with the invention encompass the treatment of subjects, wherein the disease associated with increased level of protein or misfolding is ongoing, but wherein the subjects do not exhibit manifest outward symptoms. Furthermore, the methods for treatment of the present invention contemplate treating the symptoms of existing diseases, wherein the subjects exhibit external symptoms.

The dose of the composition of the present invention will vary depending on the weight and condition of the subject, the form of the composition, the mode and period of administration, and can be determined by those skilled in the art. The optimal dose of the compound(s) may be determined according to the amount required to maximize the effect of lowering the concentration of unwanted or misfolded proteins in specific areas of the brain. For example, the dosage range can be from about 100 to about 1000 mg per day. Preferably, the dosage range is from about 200 to about 600 mg per day. The composition may be administered monthly, biweekly, weekly, daily, or several times per day in single or divided doses.

EXAMPLES

The following examples are merely illustrative of the present invention and they should not be considered as limiting the scope of the invention in any way.

Example 1

In Vitro Evidence on the Effects of a Grape Seed Extract on the Formation of Oligomers of Synthetic Aβ

The present example provides in vitro evidence of the effects of a composition, according to one embodiment of the present invention, for reducing the oligomerization of Aβ.

Materials and Methods

In Vitro $A\beta_{1-40}$ and $A\beta_{1-42}$ Aggregation Assay.

A grape seed extract product, MegaNatural®-AZ was obtained from Phenolics (Madera, Calif.). $A\beta_{1-40}$ and $A\beta_{1-42}$ peptides for in vitro $A\beta_{1-40}$ and $A\beta_{1-42}$ aggregation assays were purchased from American Peptide (Sunnyvale, Calif.). Peptides were solubilized in HFIP (Sigma), dried overnight at room temperature, and speed-vacuumed for 10 minutes. Peptides were dissolved at 1 mg/ml in $dH_2O$, and MNG-AZ GSE stock was dissolved in $H_2O$ at 400 µM. $A\beta_{1-40}$ and $A\beta_{1-42}$ (100 µg/ml) were mixed with different concentrations of MNG-AZ GSE at a 1:1 volume and incubated at 37° C. for 3 days. The effect of MNG-AZ on Aβ aggregation was analyzed by western blot analysis using 6E10 antibody.

Photo-Induced Cross-Linking of Unmodified Proteins (PI-CUP) Assay.

Freshly isolated low molecular weight (LMW) $A\beta_{1-42}$ or $A\beta_{1-40}$ peptide was mixed with 1 µl of 1(×1), 2(×2), 5(×5) or 10(×10) mM tris(2,2'-bipyridyl)dichlororuthenium(II) (Ru(bpy)) and 1 µl of 20(×1), 40(×2), 100(×5) or 200(×10) mM ammonium persulfate (APS) in the presence or absence of 50 µM MNG-AZ GSE in 10 mM phosphate, at pH 7.4. The mixture was irradiated for 1 second, and quenched immediately with 10 µl of Tricine sample buffer (Invitrogen, CA) containing 5% β-mercaptoethanol. The reaction was subjected to SDS-PAGE and visualized by silver staining (SilverXpress, by Invitrogen, Calif.). Glutathione S-transferase was cross-linked under similar conditions and used as control peptide.

Results and Discussion

Figure 2:
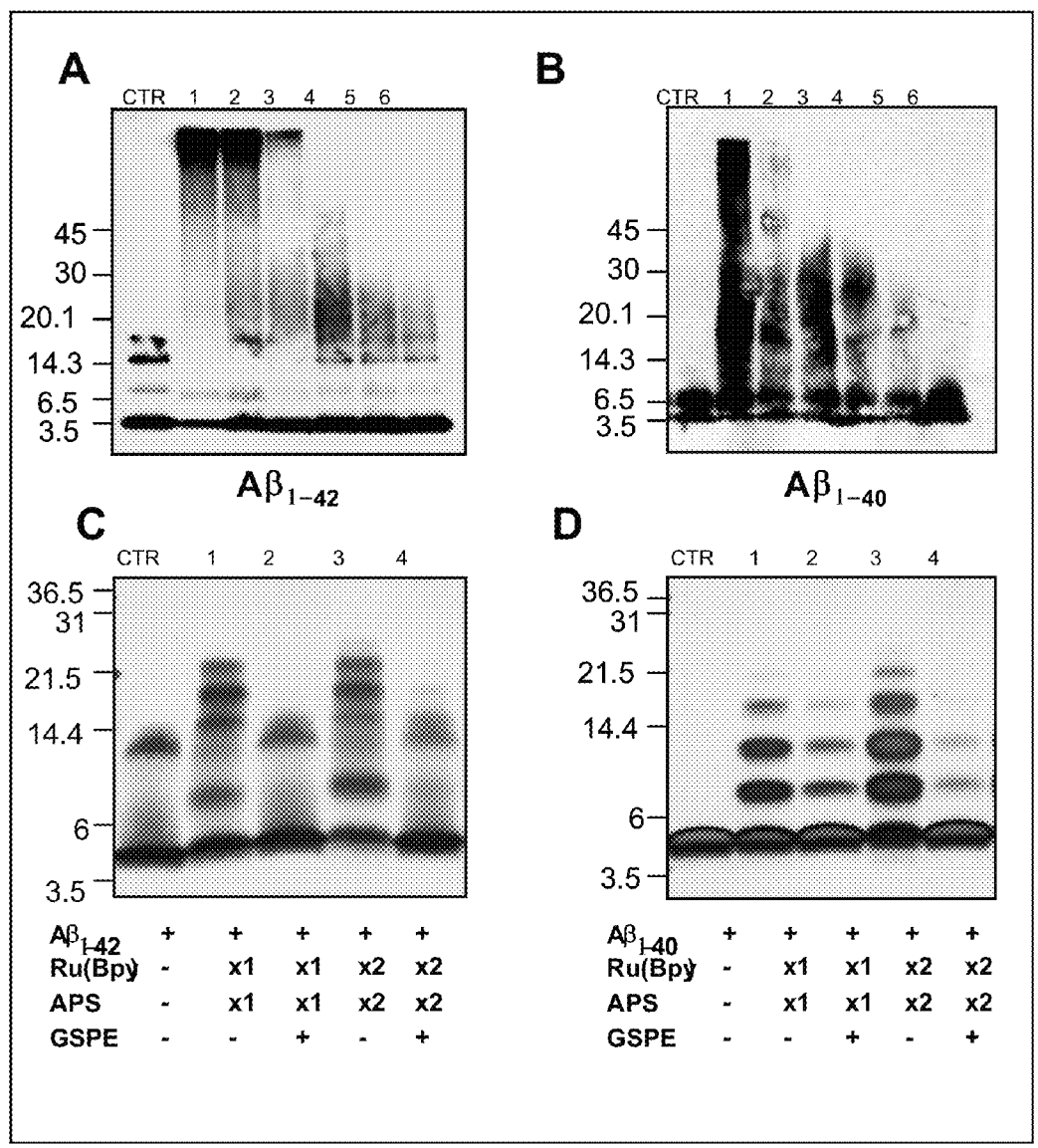
FIG. 2 presents the effect of MNG-AZ GSE on the conversion of Aβ peptides into their soluble oligomeric forms in vitro.

The effect of MNG-AZ on the inhibition of oligomerization of Aβ is illustrated in FIG. 2. Oligomerization of synthetic $A\beta_{1-42}$ (2A) and $A\beta_{1-40}$ (2B) was inhibited by MNG-AZ in a concentration-dependent fashion, as illustrated by SDS-PAGE (lanes 1-6 in FIGS. 2A and 2B: 0, 0.2, 1, 5, 25 and 100 µM of Aβ; CTR are samples without incubation). Similar results were observed in SDS-PAGE results of $A\beta_{1-42}$ (FIG. 2C) and $A\beta_{1-40}$ (FIG. 2D) following PICUP chemistry (lanes 1 and 2 in FIGS. 2C and 2D: Aβ peptide with 1× Ru(Bpy) and APS in the presence and absence of MNG-AZ, respectively; lanes 3 and 4: Aβ peptide with 2× Ru(Bpy) and APS in the presence or absence of MNG-AZ GSE, respectively; CTR: non-cross-linked $A\beta_{1-42}$ (2C) or $A\beta_{1-40}$ (2D) used as monomer control.

The above results consistently indicate that MNG-AZ may effectively inhibit the oligomerization of Aβ in vitro. Furthermore, the inhibitory effect of MNG-AZ appears to be concentration or dose dependent. These results demonstrate that MNG-AZ GSE can prevent or treat diseases associated with accumulation, aggregation or deposition of Aβ.

Example 2

Evaluation of AD-Type Neuropathology of TG2576 Mice

The present example illustrates the in vivo effects on the Aβ neuropathology of a transgenic mouse model of administering a composition according to one embodiment of the present invention.

Materials and Methods

Tg2576 Mice and MNG-AZ GSE Treatment.

Adult female Tg2576 mice (Taconic, Germantown Inc.) were assigned to two different groups: the MNG-AZ GSE treatment group and the water control group. MNG-AZ GSE was delivered in their drinking water at a concentration of 1.2 g/L, which resulted in a final intake of 200 mg/kg/day. This was equivalent to a human dose of 1 gm/day using FDA criteria for converting drug equivalent dosages across species, based on body surface area (human equivalent dose in mg/kg=animal dose in mg/kg×(animal weight in kg/human weight in kg)$^{0.33}$) (http://www.fda.gov/cber/gdlns/dose.htm). Animals had free access to the liquid and standard chow. Drinking solutions were changed every three days. Liquid consumption and animal body weight were monitored weekly throughout the study. After 5 months of treatment, mice were anesthetized with the general anesthetic Ketamine HCL and Xylazine (Fort Dodge Animal Health, Fort Dodge, Iowa) and sacrificed by decapitation. Brains were harvested and hemidissected. One hemisphere was fixed in 4% paraformaldehyde for 24 hours for morphological studies. Hippocampus and neocortex were dissected from the opposite hemisphere, rapidly frozen, pulverized in liquid nitrogen and stored at 80° C. for biochemical studies.

Assessment of AD-Type Amyloid Neuropathology.

For quantitative assessment of brain Aβ peptides, frozen pulverized tissue was homogenized in 5 mol/L guanidine buffer, diluted 1:10 in phosphate-buffered saline containing 0.05% (vol/vol) Tween®-20 and 1 mmol/L Pefabloc protease inhibitors (Roche Applied Science, Indianapolis, Ind.) and centrifuged for 20 minutes at 4° C. Total $A\beta_{1-40}$ or $A\beta_{1-42}$ was quantified by sandwich ELISA (BioSource, Camarillo, Calif.). For stereologic assessment of AD-type amyloid burden in Tg2576 mice, freshly harvested brain hemispheres were immersion-fixed overnight in 4% paraformaldehyde and sectioned in the coronal plane on a vibratome at a nominal thickness of 50 µm. Every 15th section was selected from a random start position and processed for Thioflavine-S staining. All stereologic analyses were performed using a Zeiss Axiophot photomicroscope equipped with a Zeiss motorized stage and MSP65 stage controller, a high resolution Zeiss ZVS-47E digital camera and a Macintosh G3 computer running the custom designed software NeuroZoom. The amyloid burden was estimated using the Cavalieri principle with a small size grid (50×50 μm) for point counting; this procedure provided an unbiased estimate of the fractional volume occupied by amyloid plaques—expressed as a percentage of the neocortical or hippocampal volume. Estimates of plaque volume were obtained using a systematic random sampling procedure at X40 magnification.

Brain Soluble Aβ Oligomer Analysis.

The level of soluble Aβ oligomers was measured both by dot blot assay and western blot analysis. Specifically, soluble amyloid peptide was extracted by dissolving pulverized cortical tissue in PBS supplemented with protease inhibitor cocktail (Roche Applied Science, Indianapolis, Ind.). After centrifugation at 78,500 g for 1 hour at 4° C., the supernatant was analyzed. 5 μg of total protein was spotted on nitrocellulose membrane, blocked with 10% non-fat milk, and incubated with antibody A11 (Invitrogen, CA), an antibody that specifically recognizes oligomeric form of Aβ After two hours incubation at room temperature, the blot was incubated with HRP conjugated goat anti-rabbit antibody, and the immunoreactive signals were visualized using enhanced chemiluminescence detection (SuperSignal Chemiluminescent Detection Kit, Pierce, Rockford, Ill.) and quantified densitometrically (Quantity One, Bio-Rad). The same sample was also used for western analysis. 75 μg of total proteins were separated by 10-20% Tris-Tricine gel and transferred to nitrocellulose membrane, blocked for 1 hour with 10% non-fat milk. Membranes were incubated with either 6E10 (Signet), or A11. Immunoreactive signals were visualized by using enhanced chemiluminescence detection and quantified densitometrically.

APP Processing and α-, β-, γ-Secretase Activity.

Expression of holo-APP was examined by Western blot analysis with the C8 antibody (raised against AA 676-695 of human APP cytoplasmic domain). Immunoprecipitation was performed for detection of sAPP-α, sAPP-β as previously described (Wang et al., *FASEB J* 2005; 19: 659-661). α-, β- and γ-secretase activities were assessed using commercially available kits (R & D Systems). The expression of neprilysin and insulin degrading enzyme were analyzed by western blot using commercially available antibody.

Statistical Analysis.

All data and values in these examples were expressed as mean and standard error of the mean (SEM). Differences between means were analyzed using either 2-way repeated measures ANOVA or 2-tailed Student t-test. In all analyses, the null hypothesis was rejected at the 0.05 level. All statistical analyses were performed using the Prism Stat program (GraphPad Software, Inc., San Diego Calif.).

Results and Discussion

Figures 7A, 7B, 7C, 7D, 7E, 7F:
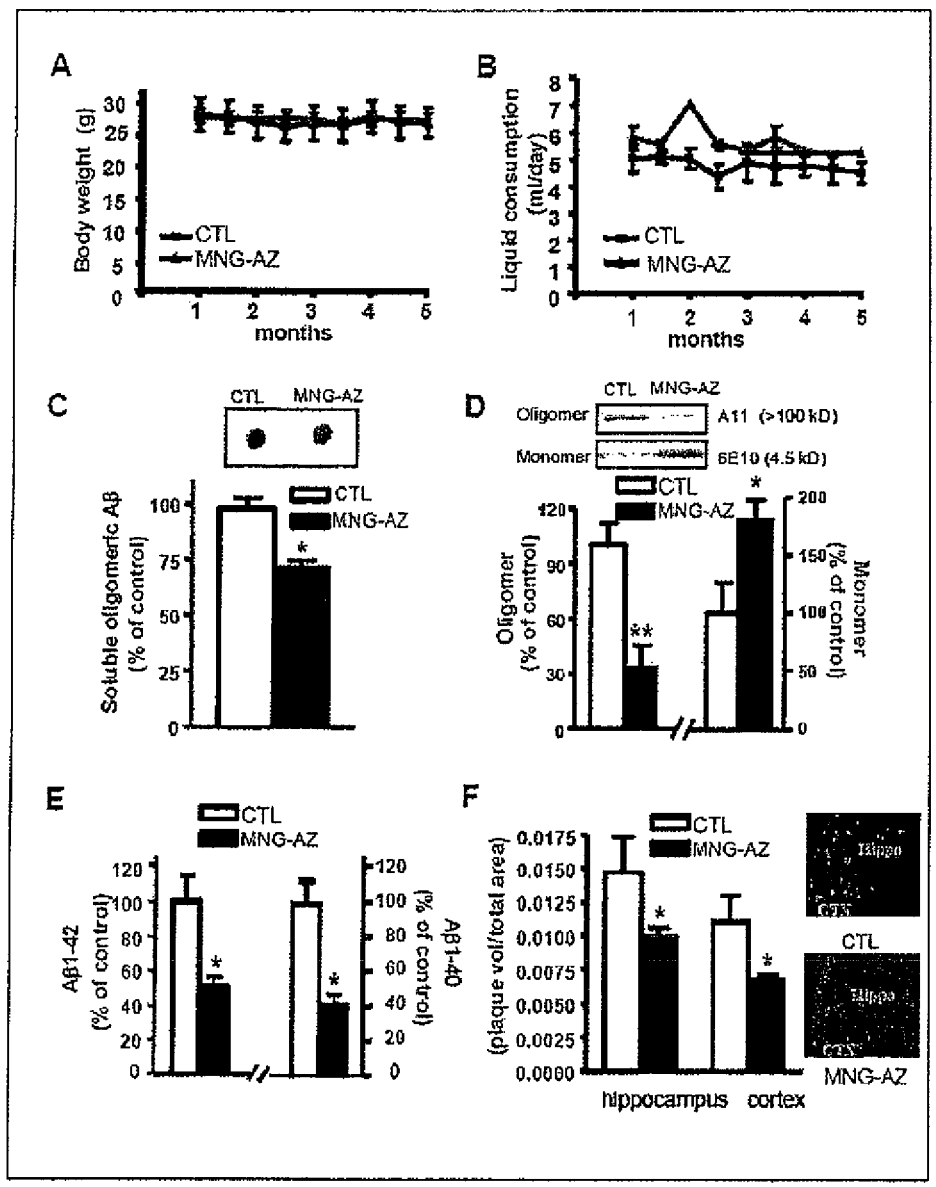
FIGS. 7A-7G.
Figure 7G:
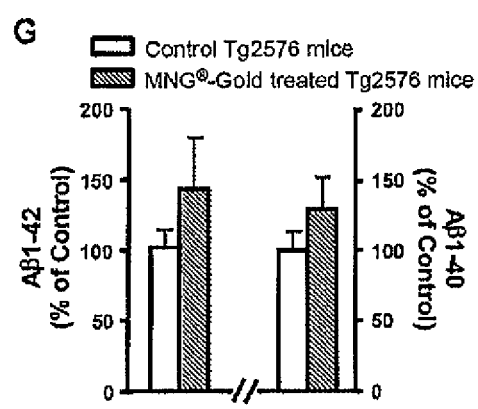

The effects of MNG-AZ GSE on the neuropathology of Tg2576 mice are illustrated in FIG. 7. FIGS. 7A and 7B show the effect of MNG-AZ GSE on body weight (7A) or liquid consumption (7B) in Tg2576 mice following 5 months treatment. FIG. 7C presents assessments of soluble, extracellular HMW-Aβ peptide contents in the brain using an antibody specific for HMW oligomeric Aβ peptides in a dot blot analysis. FIG. 7D depicts a Western blot analysis of soluble extracellular HMW oligomeric Aβ peptide (antibody A11) and monomeric Aβ peptide (antibody 6E10) in the brain of Tg2576 mice. FIG. 7E shows assessment of $A\beta_{1-42}$ and $A\beta_{1-40}$ peptide concentrations in the brain of MNG-AZ GSE treated and control mice. FIG. 7F shows stereological assessment of cerebral cortex and hippocampal formation Aβ-amyloid plaque burden in MNG-AZ GSE treated and control mice expressed as thioflavin-S positive volume as a percentage of regional volume. FIG. 7F-*inset* shows representative photographs of thioflavin-S positive Aβ amyloid plaque neuropathology in neocortex (CTX) and hippocampal formation (Hippo) in untreated control (top panel) and MNG-AZ treated Tg2576 mice (low panel). Values represent group mean±SEM, n=5-6 mice per group. *p<0.05, **p<0.01 by two-tailed student t-test analysis. FIG. 7G illustrates an assessment of $A\beta_{1-42}$ and $A\beta_{1-40}$ peptide concentrations in the brain of the parallel studies on the in vivo efficacy of MegaNatural®-Gold.

These results showed that MNG-AZ GSE did not result in detectable adverse effects, including changes in body weight (FIG. 7A) or water consumption (FIG. 7B). Neuropathology of Tg2576 mice following 5 months of treatment showed about two to three-fold decrease in oligomerization of endogenous Aβ peptides into HMW Aβ species, as assessed by immuno-dot blot assay using an antibody specific for Aβ oligomers (p<0.05, FIG. 7C) and by western blot using A11-antibodies (p<0.01, FIG. 7D). The reduction of HMW A11-immunoreactive oligomeric Aβ species in the brain of Tg2576 mice was found to coincide with a commensurate elevation of monomeric Aβ peptides (p<0.05, FIG. 7D), indicating that MNG-AZ GSE beneficially influence AD through the prevention of Aβ oligomerization.

FIG. 7G shows that in parallel studies, treatment of Tg2576 mice with another commercially available GSE preparation, namely MegaNatural®-Gold, did not modulate the accumulation of $A\beta_{1-42}$ and $A\beta_{1-40}$ peptides in the hippocampal formation of Tg2576 mice compared to control Tg2576 mice. The result in FIG. 7G suggests that MNG-AZ is unique among currently available GSE preparations in its efficacy to modulate amyloid-type neurodegeneration in the brain due to its substantially lower galloylated proanthocyanidins content.

Recent observations suggest that the prevention of Aβ oligomerization into HMW species in the brain may lead to compensatory reductions in total Aβ peptides and eventually amyloid neuritic plaque content in the brain, possibly as a result of preferential clearance of monomeric Aβ peptides from the brain relative to oligomeric Aβ species (Morelli et al., *Biochem* 2005:38:129-145). Consistent with this hypothesis, the results of the present example showed that, in addition to reducing levels of HMW oligomeric Aβ species (FIGS. 7C, 7D), long-term MNG-AZ GSE treatment also significantly reduced the amounts of $A\beta_{1-42}$ (FIG. 7E, left panel) and $A\beta_{1-40}$ peptides (FIG. 7E, right panel) and amyloid neuritic plaque burden (FIG. 7F), relative to age- and gender-matched water-treated control mice.

Figure 8:
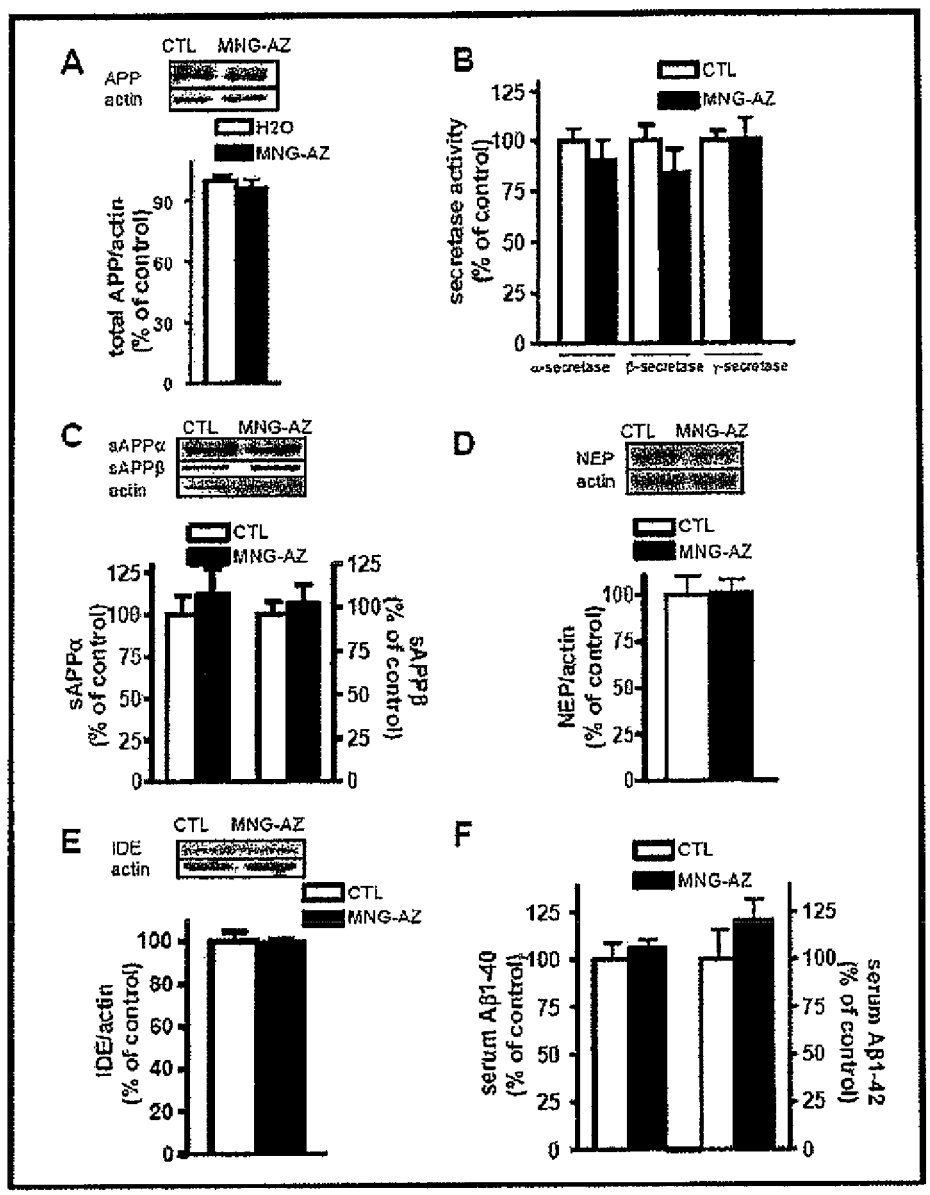
FIG. 8 shows the results of various experiments for elucidating potential mechanisms for the beneficial effects of MNG-AZ GSE.

In addition, alternative potential mechanisms that may have contributed to the beneficial effects of MNG-AZ GSE on amyloid neuropathology were evaluated. No detectable changes in the content of holo-APP (FIG. 8A) were found, nor were any changes in the enzymatic activities of α-, β-, and γ-secretase, or the content of soluble APPα and soluble APPβ (FIGS. 8B, 8C). Moreover, no detectable changes were observed in the content of neprilysin (FIG. 8D) or insulin-degrading enzyme (FIG. 8E), which are the main proteolytic enzymes responsible for Aβ degradation. Finally, no detectable changes in the levels of $A\beta_{1-42}$ and $A\beta_{1-40}$ peptides in peripheral serum were found (FIG. 8F).

These observations suggest that MNG-AZ GSE might exert its beneficial effect in vivo primarily through the prevention of Aβ oligomerization into soluble HMW species, as found in vitro.

Example 3

AD-Type Cognitive Function Assessment on TG2576 Mice

The example demonstrates the effects of administering compositions according to some embodiments of the present invention on the cognitive function of Tg2576 transgenic.

Materials and Methods

Tg2576 mice were treated with MNG-AZ GSE for 5 months and cognitive function was assessed at 11 months of age. Spatial learning memory was assessed by the Morris water maze behavioral test as previously described (Morris, *J Neurosci Methods* 1984; 11: 47-60). Spatial memory is assessed by recording the latency time for the animal to escape from the water onto a submerged escape platform as a function of learning trials during the learning phase. 24 hours after the learning phase, mice were examined in a probe trial by removing the escape platform without changing the visual cue. The behavior analysis was consistently conducted during the last 4 hours of the day portion of the light cycle in an environment with minimal stimuli (e.g., noise, movement, or changes in light or temperature).

Results and Discussion

Figure 9:
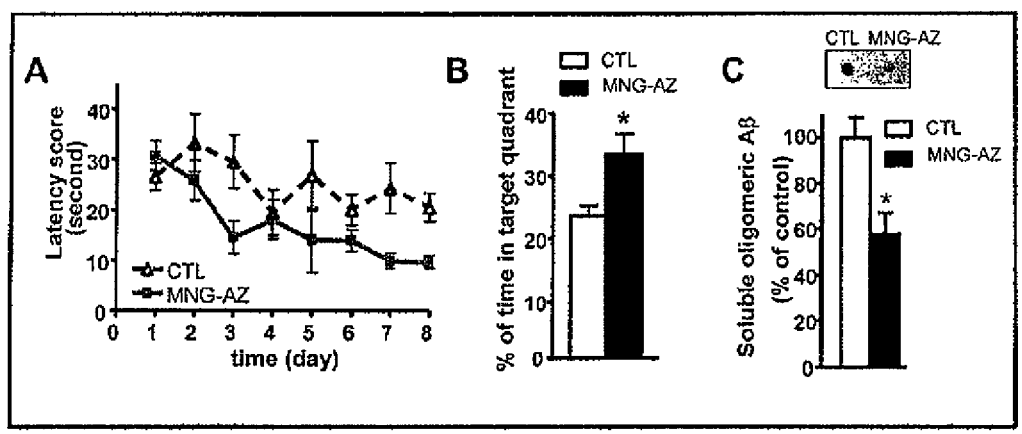
FIG. 9 illustrates the attenuation of cognitive deterioration in Tg2576 mice treated with MNG-AZ GSE.

FIG. 9 illustrates the attenuation of cognitive deterioration in Tg2576 mice treated with MNG-AZ GSE coincidental with decreased extracellular HMW oligomeric Aβ. FIGS. 9A and 9B show the influence of MNG-AZ GSE on Aβ related spatial memory in Tg2576 mice as determined by Morris water maze tests. FIG. 9A depicts latency score (representing time taken to escape to the platform from the water) as a function of time of treatment. FIG. 9B shows probe trial percent of time the Tg2576 mice spent on the target quadrant (calculated as the ratio of time spent in the target quadrant area relative to the time spent in the rest of the pool). FIG. 9C presents assessment of soluble, extracellular HMW-Aβ peptide content in the brain of Tg2576 mice using an antibody specific for HMW oligomeric Aβ peptides in a dot blot analysis. FIG. 9C-*inset* shows a representative dot-blot analysis of HMW-soluble Aβ contents. Values represent group mean±SEM, n=7-9 mice per group; in FIG. 9B, ***$p<0.0001$; in FIG. 9C, *$p<0.01$ by 2-tailed student t-test analysis.

11-month old Tg2576 mice exhibited significant spatial reference memory function impairments, as was reflected by their inability to learn to use spatial reference cues to localize a hidden escape platform during learning trials in a Morris water maze test (FIG. 9A). In contrast, MNG-AZ-treated Tg2576 mice performed significantly better in the spatial memory behavioral function test and were able to learn to use spatial reference cues to locate the escape platform, as reflected by significant reductions in escape latency time with progressive learning trials (two-way repeated measure ANOVA; GSPE vs. control group: $F_{1,11}=4.90$; $p=0.049$ for GSPE-treatment, $F_{7,77}=4.25$; $p=0.0005$ for time and $F_{7,77}=1.63$; $p=0.140$ for interaction) (FIG. 9A). MNG-AZ induced attenuation of cognitive impairment in Tg2576 mice was confirmed by analysis of spatial memory retention in a probe trial showing that MNG-AZ-treated mice spent significantly more time in the target quadrant area relative to water-treated control mice (FIG. 9B). This cognitive function improvement coincided with a significant reduction of HMW oligomeric Aβ species in the brain of MNG-AZ-treated Tg2576 mice relative to the control mice (FIG. 5C).

Figure 10:
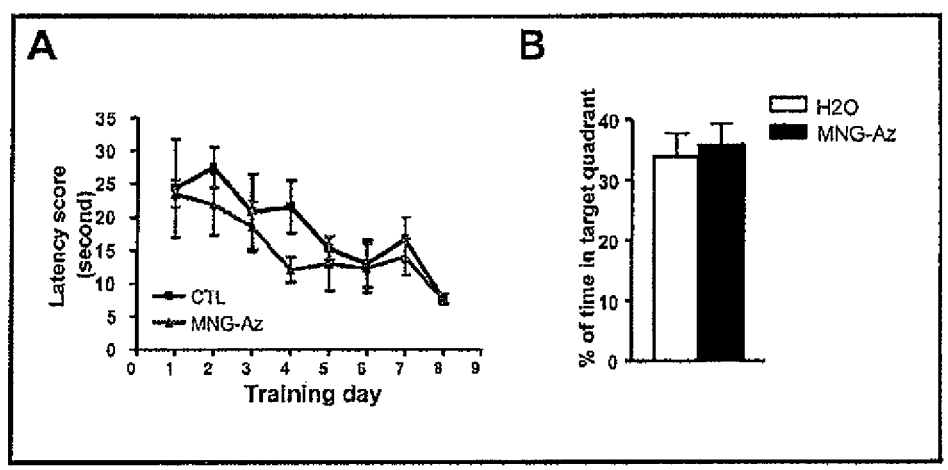
FIGS. 10A-10B.

In a control study, MNG-AZ GSE treatment was found to not influence cognitive function in strain-, age- and gender-matched wild type animals (FIGS. 10A and 10B). The above results suggest MNG-AZ GSE may benefit spatial memory reference deficits in Tg2576 mice selectively, through the attenuation of AD-type Aβ-mediated response in the brain.

Example 4

In Vitro Effect of MNG-AZ on Aggregation of Tau Proteins

The present example illustrates the in vitro effects of a composition according to an embodiment of the present invention on the tau peptide aggregation, dissociation of pre-formed tau aggregates, and stability of native tau fibrils obtained from AD brain specimen.

Materials and Methods

Assessments of MNG-AZ Anti-Tau Aggregation Bioactivity In Vitro.

A 6-amino acid N-acetylated peptide (Ac-$^{306}$VQIVYK$^{311}$) tau peptide, corresponding to residues 306 to 311 of tau, is obtained commercially. This synthetic tau peptide is a short peptide segment found in the microtubule binding region of tau protein. Evidence suggests that this short peptide segment is essential for tau polymerization. (Goux et al., *J. Biol. Chem.* 2004; 279: 26868-26875). This is supported by in vitro biophysical observation that the short Ac-$^{306}$VQIVYK$^{311}$ peptide spontaneously aggregates into filament structures in the presence of salt (Goux et al., 2004, supra). Oligomerization of the Ac-$^{306}$VQIVYK$^{311}$ peptide was essentially as described in Goux et al., 2004, supra. In brief, the synthetic tau peptide was dissolved in 20 mM MOPS, pH 7.2. Polymerization of the tau peptide was conducted in a final 75 μl 20 mM MOPS (pH 7.2) solutions containing 2.2 μM peptide and 10 μM thioflavin-S (ThS). The reaction was initiated by addition of salt to a final 0.15 M concentration. The kinetics of tau peptide aggregation in the absence or presence of the varying concentrations of MNG-AZ was assessed over 1 hour by following the increase in ThS fluorescence upon binding of ThS to aggregated peptide species; fluorescent excitation was induced at 436 nm and fluorescent emission was detected at 470 nm.

Further, PICUP, Circular Dichroism (CD) spectroscopy, and electron microscopy methodologies were also used to explore the impact of the MNG-AZ on initial protein-protein interactions necessary for the formation of tau peptide aggregates.

For PICUP assay, 25 μM tau peptide were cross-linked in the presence or absence of equal molar (25 μM) MNG-AZ, and multimeric tau peptides were resolved by SDS-PAGE and visualized by silver staining.

For CD spectroscopy, the tau peptide was incubated at 37° C. for 1-3 days in the presence of 10 mM phosphate, pH 7.4, and the CD spectra were obtained at the beginning of the incubation (0 day), and each of the following 3 days.

For electron microscopy, the tau peptide was incubated at 37° C. for 3 days in 10 mM sodium phosphate, pH 7.4 in the absence or presence of 1:1 molar ratio of GSE relative to tau peptides. Following incubation, the solution was centrifuged at 16,000×g for 5 min, and then 200 μl of the supernatants were fractionated by size exclusion column. Tau fibrils were detected and recovered at elution time of ~12 min by UV absorbance at 254 nm.

Assessments of the Capacity of MNG-AZ in Dissociating Pre-Formed Tau Aggregates In Vitro.

Synthetic Ac-$^{306}$VQIVYK$^{311}$ tau peptide aggregated in the absence of the MNG-AZ GSE. After formations of tau aggregates, varying concentrations of MNG-AZ was added to the reactions and changes in the contents of tau aggregates in response to additions of the GSE were monitored by following ThS fluorescence.

Assessment of the capacity of MNG-AZ GSE in destabilizing native tau fibrils obtained from AD brain specimens. PHFs were isolated and purified from post-mortem brain specimens from AD cases, and some PHFs samples were treated with MNG-AZ (100 µM) for 5 sec or 1 h. The results were observed by electron microscopy (Hitachi H700).

Evaluation of Effects of MNG-AZ GSE on Trypsin Digestion of Tau Filaments.

PHFs were isolated from AD brain specimens. Some samples of PHFs were treated with 100 µM MNG-AZ for 10 min. Some samples of PHFs (whether pretreated with MNG-AZ) were further incubated with 1 µg trypsin for 10 min. The results were observed by electron microscopy (Hitachi H700).

Results and Discussion

MNG-AZ Inhibits Tau Aggregation.

Figure 11:
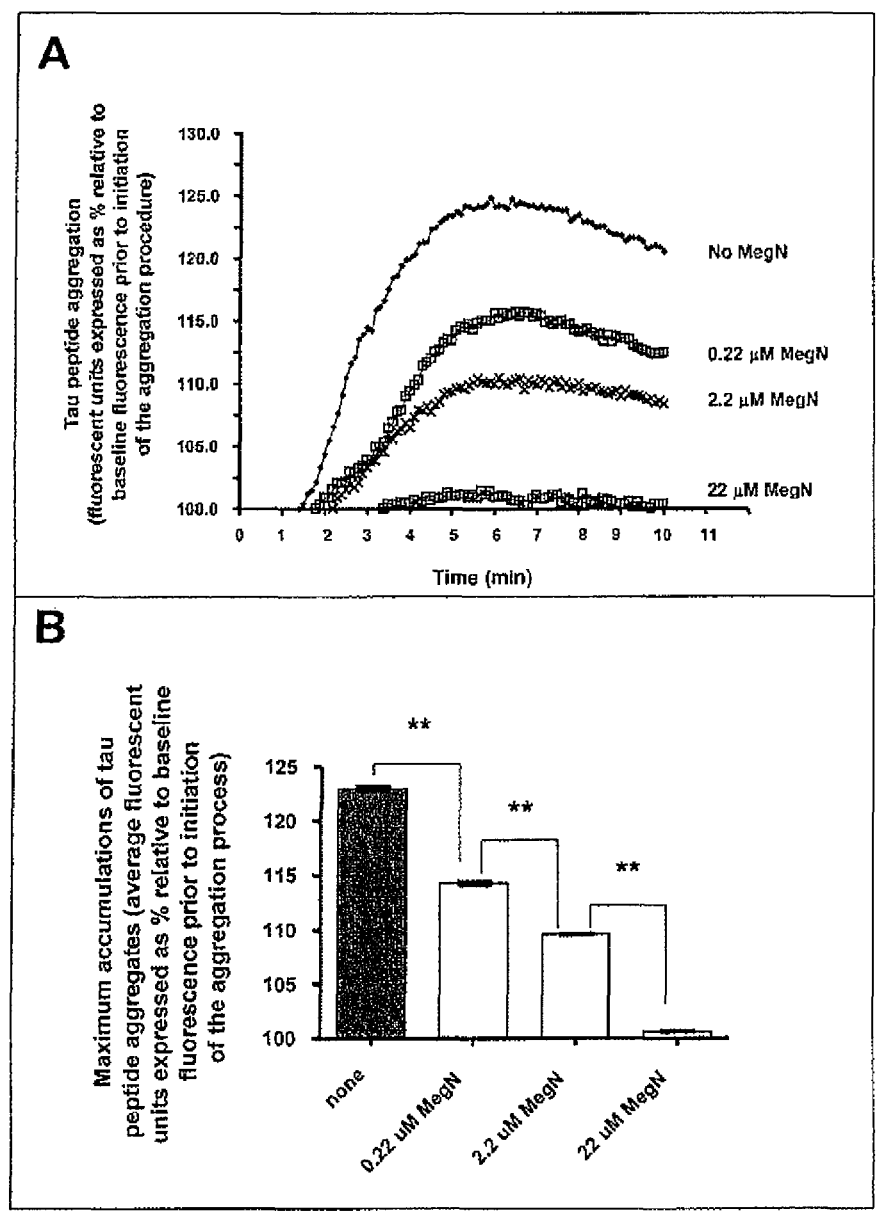
FIG. 11 illustrates the kinetics of aggregation of a tau peptide in the absence of presence of MNG-AZ GSE.

The results of tau aggregation inhibition by MNG-AZ GSE are illustrated in FIG. 11 (note that MNG-AZ is denoted as MegN in FIG. 11). Synthetic Ac-$^{306}$VQIVYK$^{311}$ tau peptide readily forms into aggregates over time in the presence of salt, as reflected by increasing ThS fluorescence as a function of reaction time (FIG. 11A, where accumulations of aggregated tau as a function of time were assessed ThS-fluorescence; concentrations of the GSE at 0.22 µM, 2.2 µM and 22 µM correspond to, respectively, 1:10, 1:1, and 10:1 molar ratio of GSE relative to tau peptides).

Addition of 0.22 to 22 µM MegaNatural®-AZ GSE significantly interfered with aggregations of the tau peptide in a dose-dependent manner (one-way ANOVA, p<0.0001); the calculated mean maximum fluorescent emission in the absence of the GSE is 122.9±1.3 units, compared to calculated mean fluorescent emissions of 114.2±1.1, 109.6±0.6 and 100.6±0.3 units, respectively, in the presence of 0.22, 2.2 and 22 µM MegaNatural®-AZ GSE (as shown in FIG. 11B where maximum accumulation of tau aggregates is calculated as average fluorescent unit from 6-10 min). Moreover, each step-wise increase in the contents of MNG-AZ GSE resulted in significant incremental reductions in ThS fluorescence (Tukey post-hoc pair analysis, p<0.001 for no MNG-AZ vs. 0.22 µM MNG-AZ, 0.22 vs. 2.2 µM MNG-AZ, and 2.2 vs. 22 µM MNG-AZ). Interestingly, detectable reduced accumulations of tau peptide aggregates were observed at a low content of 0.22 µM MNG-AZ GSE, which corresponds to molar ratio of 1:10 molar ratio of the GSE relative to tau peptides. Tau peptide aggregation was completely inhibited at 22 µM GSE in which the GSE was present in 10:1 excess molar ratio relative to tau peptides (FIGS. 11A and 11B).

Figure 16:
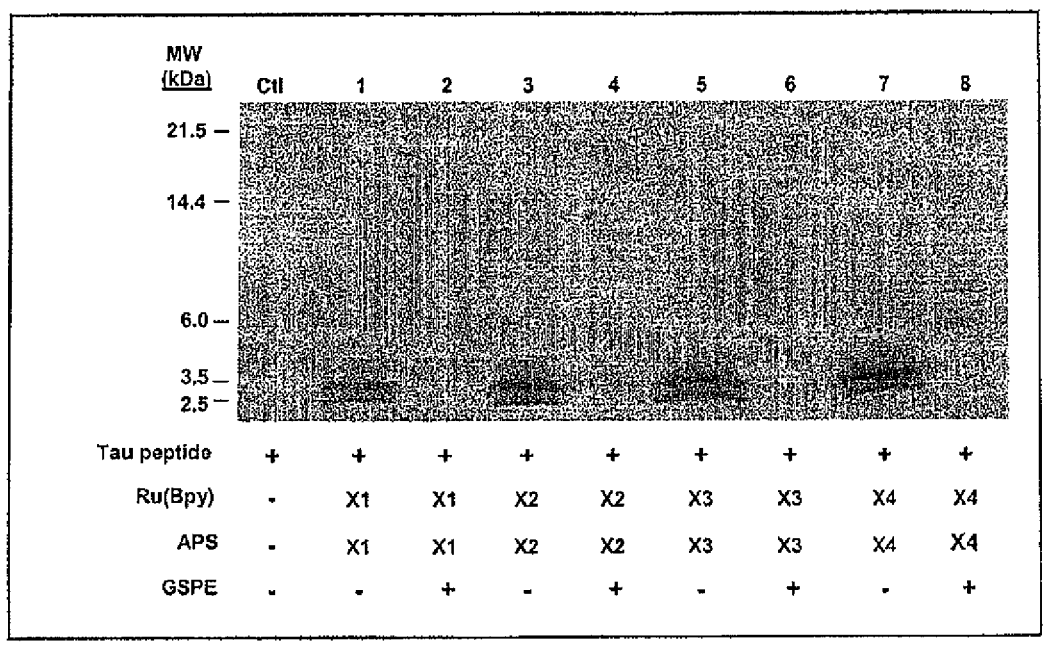
FIG. 16.

The tau aggregates were significantly reduced in the presence of MNG-AZ, as shown in the PICUP assay results (FIG. 16, wherein the concentrations of reagents are as follows. Control: no Ru(Bpy) and no APS; Lanes 1, 2: 1 µl of 1 mM Ru(Bpy) and 1 µl of 20 mM APS; Lanes 3, 4: 2 µl of 1 mM Ru(Bpy) and 2 µl of 20 mM APS; Lanes 5, 6: 3 µl of 1 mM Ru(Bpy) and 3 µl of 20 mM APS; Lanes 7, 8: 4 µl of 1 mM Ru(Bpy) and 4 µl of 20 mM APS). This indicates that MNG-AZ may inhibit tau peptide aggregation, in part, by interfering with the initial stages of tau peptide self-association.

Figure 17:
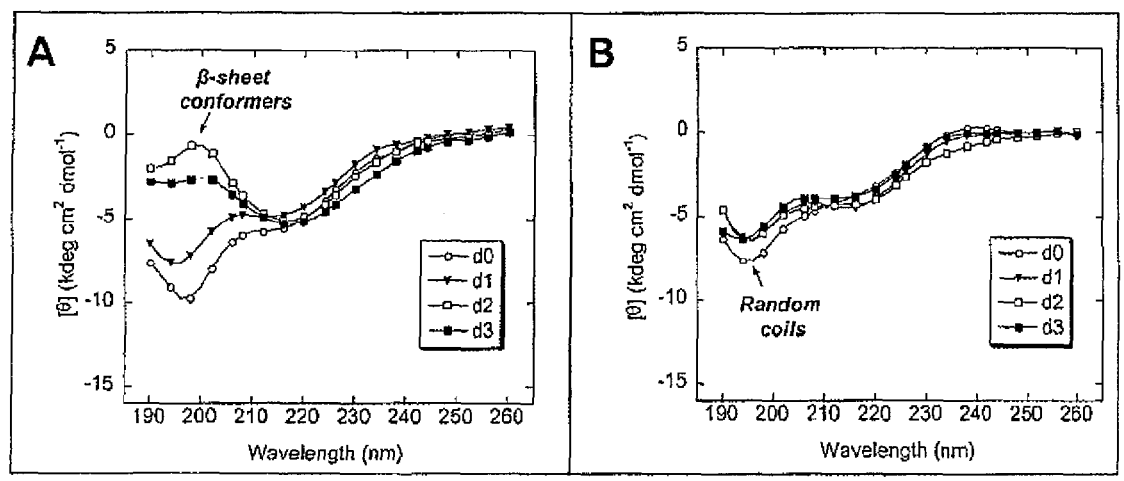
FIG. 17 illustrate the effect of MNG-AZ GSE on tau peptide aggregation using Circular Dichroism spectroscopy. Tau peptide aggregation in the absence of the MNG-AZ is shown in FIG. 17A, whereas tau peptide aggregation in the presence of 1:1 molar ratio of MNG-AZ relative to tau peptides is shown in FIG. 17B. The curves denoted with legends d0, d1, d2, and d3 in FIGS. 17A and 17B represent the spectra obtained in day 0, 1, 2, 3 in the course of incubation of a synthetic tau peptide (at 37° C.), respectively. The arrows indicate spectra characteristic of ordered conformers.

Conformations of tau peptides during the course of incubation of the tau peptides (1-3 days), as shown in the Circular Dichroism spectroscopy results (FIGS. 17A and 17B), also indicate that MNG-AZ impacted the tau peptide assembly. In the absence of the GSE, random association of tau peptide were gradually converted to ordered β-sheet conformers following 2-3 days of incubation, as indicated by the growing magnitude of the portion of the spectra centered at ~198 nm (FIG. 17A). In contrast, in the presence of 1:1 molar ratio of GSE relative to tau peptides, co-incubation of tau peptide with the GSE prevented the conversion of tau peptides into ordered secondary structures (FIG. 17B).

Figure 18:
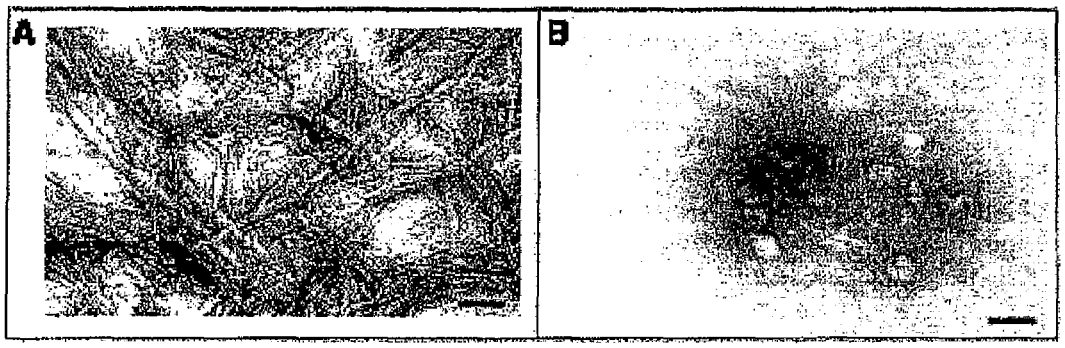
FIG. 18 illustrates the effect of MNG-AZ GSE on tau fibril morphology using electron microscopy. Tau fibril morphology in the absence of MNG-AZ is shown in FIG. 18A; tau fibril morphology in the presence of MNG-AZ is shown in FIG. 18B. Scale bars indicate 100 nm.

As studied by electron microscopy, morphology of tau peptide conformers in the absence and presence of MNG-AZ showed that the tau peptide spontaneously aggregates into helical protofibrils (FIG. 18A). In contrast, the presence of GSE completely inhibited tau peptide protofibril formation (FIG. 18B).

Collectively, the above observations suggest that MNG-AZ interfered with the aggregation of tau protein into oligomeric PHFs.

MNG-AZ Facilitates Dissociation of Pre-Formed Tau Aggregates.

Figure 12:
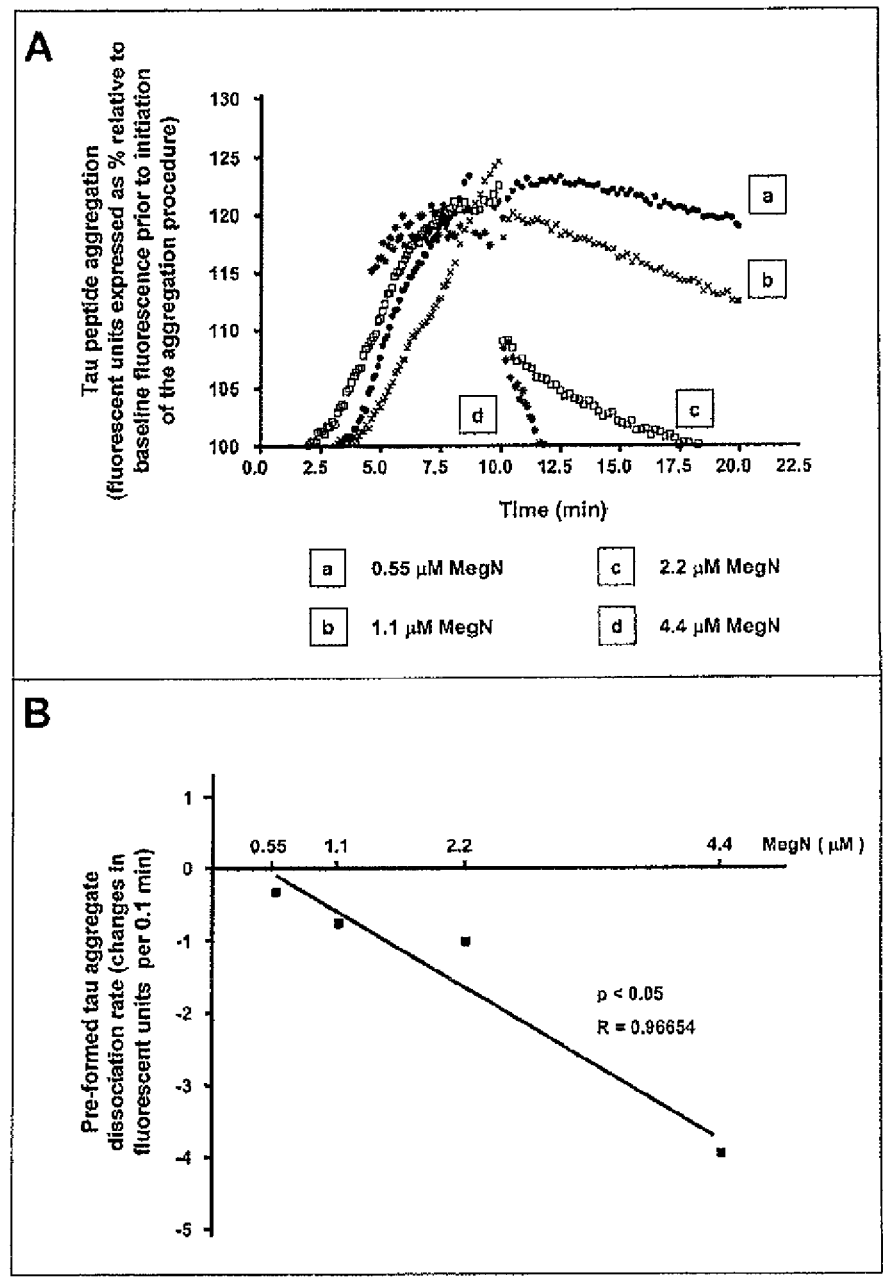
FIG. 12 illustrates the effect of MNG-AZ GSE in dissociating pre-formed aggregates of a tau peptide.

MNG-AZ is shown to dissociate pre-formed Ac-$^{306}$VQIVYK$^{311}$ tau peptide aggregates. In particular, the addition of 1.1 µM of the MNG-AZ, corresponding to a molar ratio of 1:1 MNG-AZ relative to tau peptides, was able to reduce the content of pre-formed tau peptides aggregates as reflected by increasingly lower amounts of ThS-positive tau aggregates as a function of time (FIG. 12A plots the ThS fluorescence of the tau aggregate contents at different MNG-AZ concentrations (0.55-4.4 µM)). As expected, parallel studies using higher concentrations of the MNG-AZ (2.2 µM and 4.4 µM MNG-AZ) also promoted dissociations of pre-formed tau peptide aggregate. Note that MNG-AZ is denoted as MegN in FIG. 12A and FIG. 12B below. The dose-response efficacy of MNG-AZ for dissociating pre-formed tau aggregates were investigated by calculating the dissociation rate of tau aggregate in the presence of varying concentrations of MNG-AZ GSE by linear regression analysis of ThS fluorescent emission (FIG. 12B). The addition of increasing concentrations of MNG-AZ GSE from 1.1 to 4.4 µM appeared to promote the dissociation of pre-formed tau peptide aggregates in a dose-dependent manner. In other words, the rate of dissociation of aggregated tau peptides was directly correlated to the concentration of MNG-AZ GSE (Pearson R=0.96654, p<0.05).

MNG-AZ Interferes with the Stability of Tau Fibrils.

Figure 19:
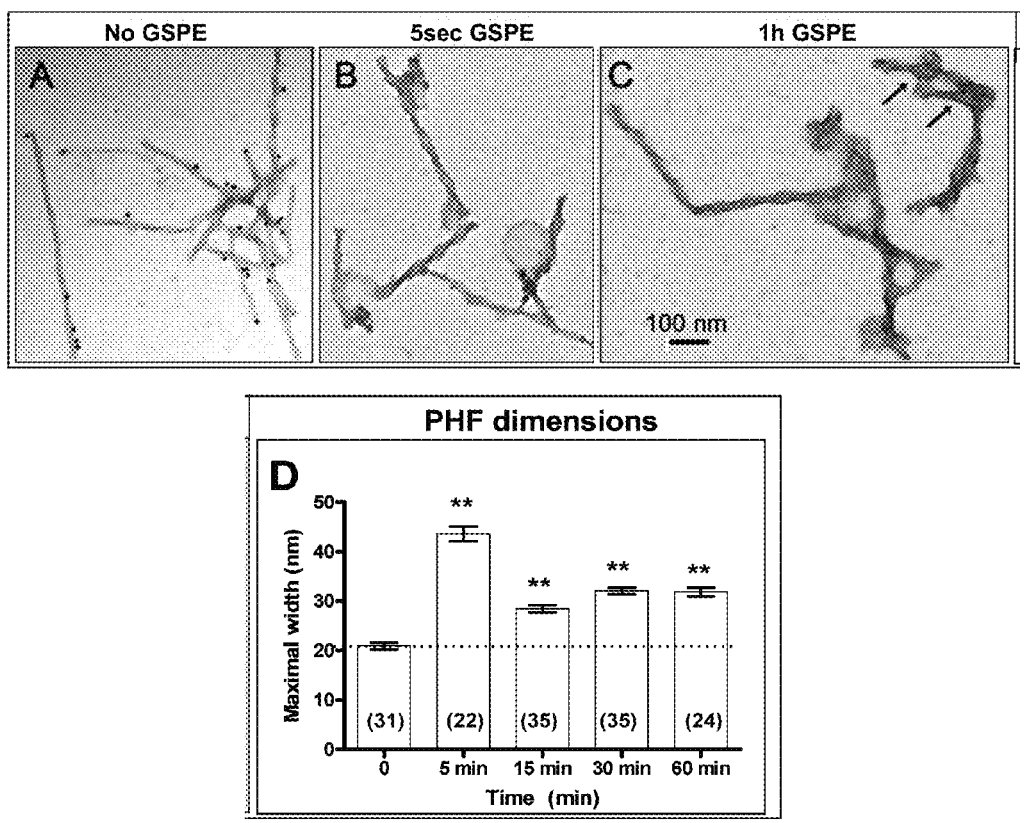
FIG. 19 illustrates the effect of MNG-AZ GSE on the ultrastructural characteristics of native paired helical fibrils (PHFs) isolated from AD brain specimens.

The effects of MNG-AZ on the stability of tau fibrils as investigated by electron microscopy were illustrated in FIG. 19. FIG. 19A shows PHFs from AD, which displays typical organized fibril structures with an average width of 18.9+3.4 nm and an average helical twist length of 81.3+10.8 nm, and immunogold labeling, using the PHF1 antibody, localizes a phosphoserine 396/404 epitope proximal to the PHF tight core. Interestingly, incubations of isolated PHFs with the GSE induced stepwise PHF unfolding with increasing duration of GSE exposure (FIGS. 19B-19D); 1 h incubation with the GSE led to a 67% increase in the width of the fibrils (to 31.6+3.8 nm) without affecting average helical twist width and helical twist of GSE-treated PHFs was, respectively, 31.6+3.8 and 77.4+10.8 nm) (FIGS. 19C, 19D). Moreover, it was found that GSE treatment masked immunoreactivity of the isolated tau fibrils to the PHF1 antibody (FIGS. 19B and 19C, compared to FIG. 19A).

Figure 20:
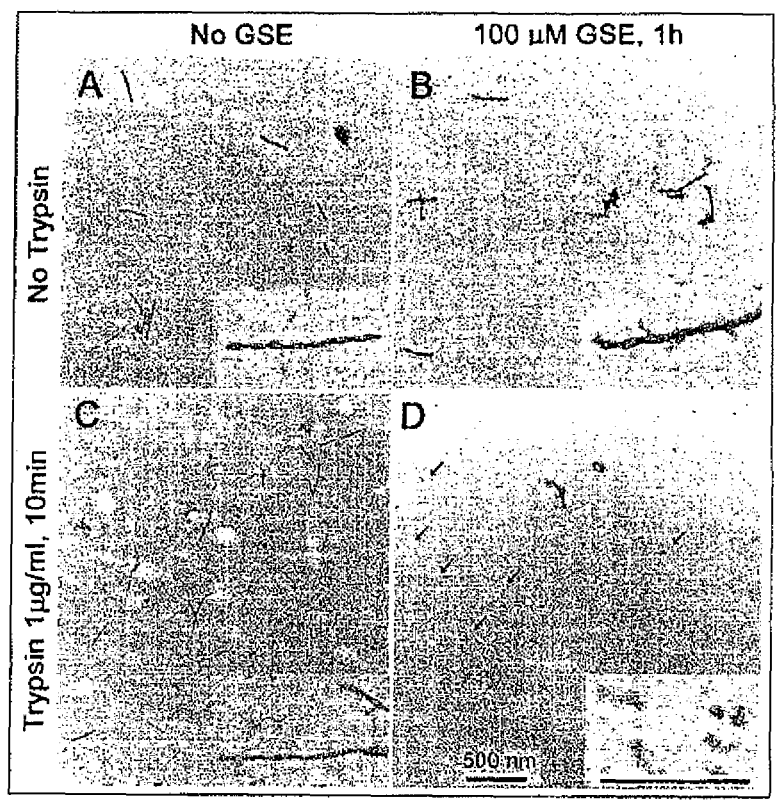
FIG. 20 illustrates the effect of MNG-AZ GSE on trypsin digestion of PHFs.

The treatment of isolated tau filaments with GSE was also found to promote trypsin digestion of the tau filaments (FIG. 20). PHFs isolated from AD brain were incubated with (FIGS. 20C and 20D) or without (FIGS. 20A, 20B) 1 μg/ml trypsin for 10 min. Samples in FIGS. 20B and 20D were also pre-treated with GSE (100 μM GSE, 1 h). PHFs retained their filamentous appearance following trypsin treatment (see insert in FIG. 20C). Pre-treatment with GSE prior to trypsin digestion caused PHFs to disintegrate into amorphous tau fragments immunoreactive to the AH-1 anti-tau antibody (see arrows and insert in FIG. 20D). These results suggest that GSE-mediated modulation on the conformation of tau filaments may promote tau degradation by cellular proteases.

In summary, MNG-AZ GSE was found to inhibit aggregations of a synthetic tau peptide into filaments and to dissociate pre-formed tau aggregates. This suggests that interactions of MNG-AZ with tau can attenuate the accumulation of tau aggregate deposits, which is a key neuropathologic feature among multiple tau-associated neurodegenerative disorders. Moreover, MNG-AZ GSE was also found to mitigate tau-mediated phenotypes by interfering with the generation and/or the stability of neurotoxic tau protofibrils. Therefore, the above observations provide strong evidence that MNG-AZ or its constituent compounds may be employed as a preventive measure to attenuate the onset of tauopathies or as therapeutics for treatment of tau-associated neurodegenerative diseases.

Example 5

In Vivo Effect of a Grape Seed Extract on Tau and Polyglutamine Expanded Forms of Htt Peptide

*Drosophila* models using the inducible Gal4/UAS system (Brand, et al., *Development*, 1993; 118: 401-415) of transgenic over-expression of disease-associated aggregation-prone proteins have successfully modeled aspects of tauopathy by over-expressing R406W mutant tau and Huntington's Disease by over-expressing Q93httexon1 (see, e.g., Sang et al., *NeuroRx*. 2005; 2: 438-446; Berger et al., *Hum Mol Genet.* 2006; 15: 433-442). In particular, over-expressing R406W in cells that form the eye (ey>R406W) leads to dramatic reduction in or complete absence of the eye; eyes that do form demonstrate abnormal morphology. Moreover, expressing Gal4 in a pan-neural pattern (elav-Gal4) in transgenic lines containing UAS-Q93httexon1 results in adult onset neurodegeneration and reduced lifespan.

The present example illustrates the in vivo benefits of a grape seed extract on *Drosophila* phenotypes carrying mutant tau (R406W) or polyglutamine expanded forms of htt (Q93httexon1) which model certain forms of tauopathy and Huntington's Disease, respectively.

Materials and Methods

Figures 13A, 13B:
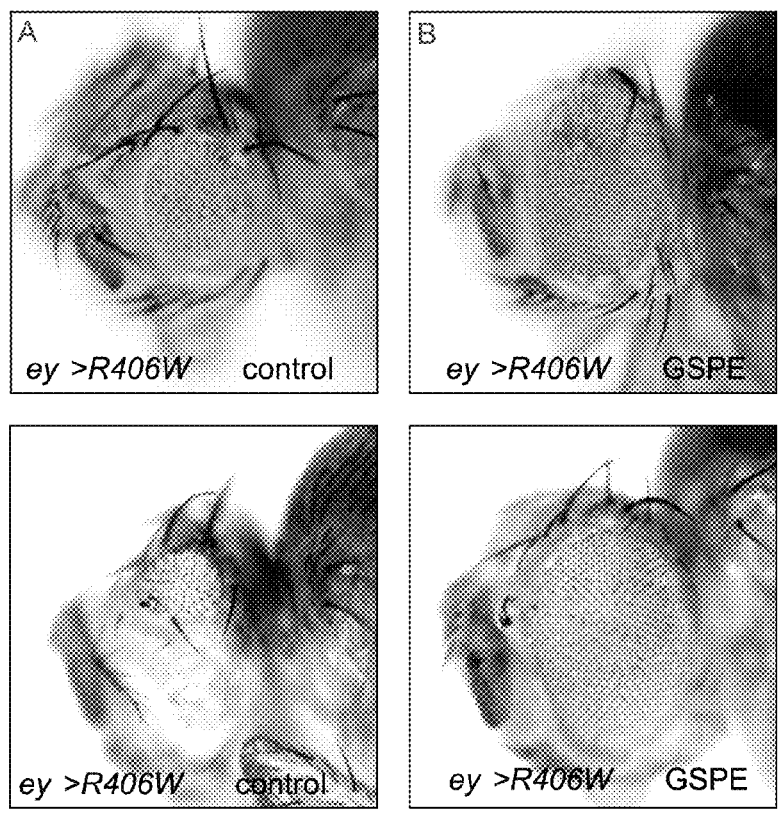
Figure 14:
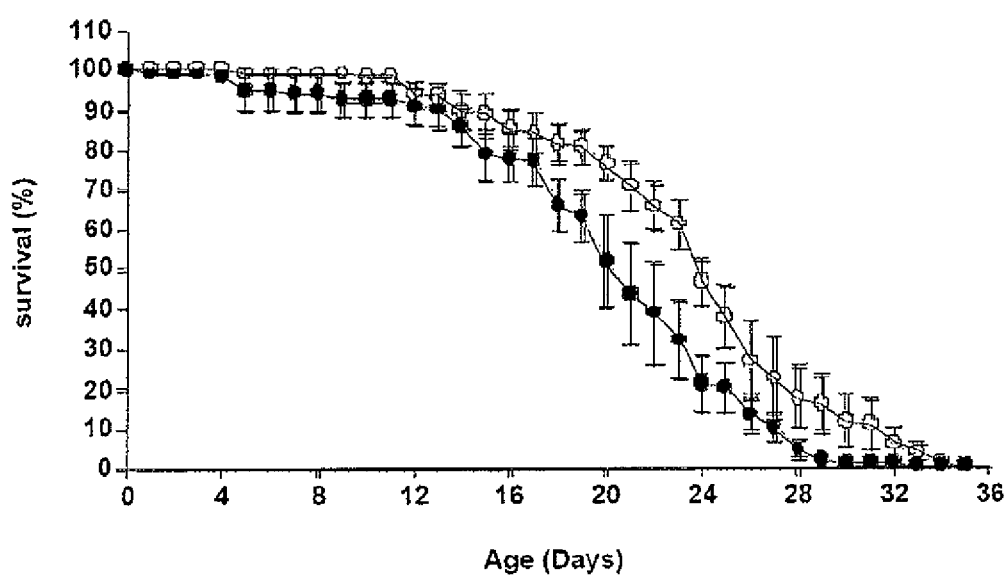
FIG. 14.
Figure 13:
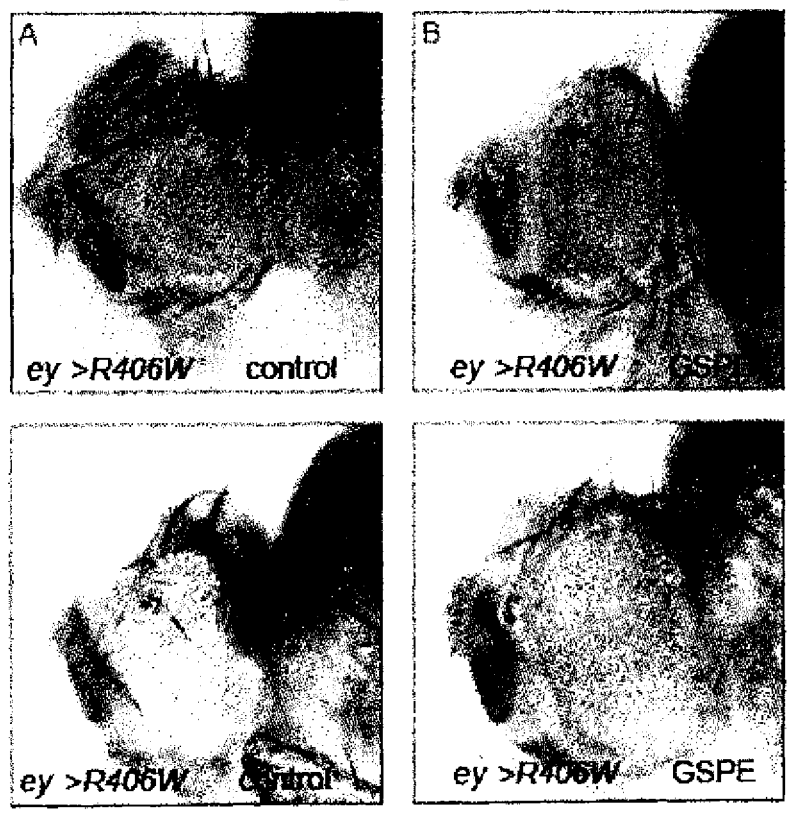
FIG. 13 illustrates the benefits of MNG-AZ GSE on a *Drosophila* model.
Figure 13:
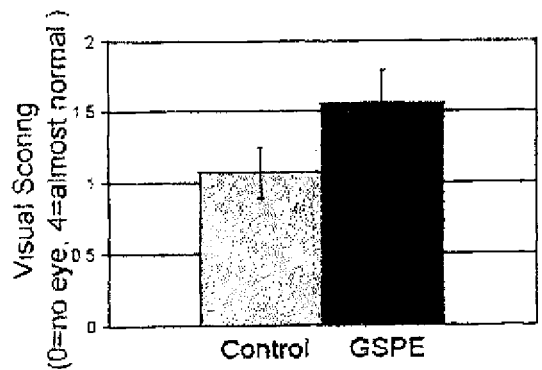
Figure 13:
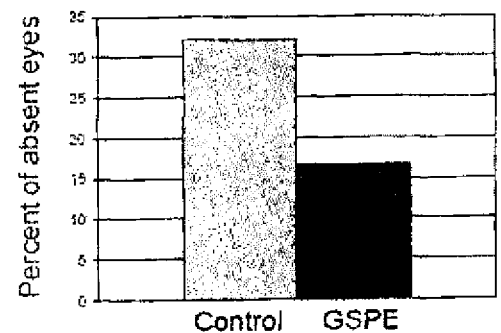

Examination of Eye Phenotype of Ey>R406W Flies.
ey>R406W eggs were laid in and reared on control food (instant fly medium formula 4-24 blue) or food supplemented with 2.8 μg/ml MNG-AZ GSE (or GSPE, in FIGS. 13 and 14). The eyes of *Drosophila* were observed under microscope.
Lifespan Monitoring of Elav>httQ3 Flies.
Male flies over-expressing Q93httexon1 in a pan-neural pattern using elav-Gal4 (elav>Q93httexon1) were collected within one day of eclosion and placed 10 per vial with control food or food supplemented with 2.8 μg/ml MNG-AZ GSE. Surviving flies were counted each day and transferred to fresh vials every few days.

Results and Discussion

GSE Suppresses R406W Tau Over-Expression in the Eyes of *Drosophila*.
Over-expression of R406W early in eye development resulted in a small or no eye (FIG. 13A), but GSE treatment suppressed reduction in eye size (FIG. 13B) (male eyes are shown). The range of ey>R406W phenotypes varied from trial to trial, so trials were examined individually. Visual scoring of male eyes from a representative experiment were collected within 3 days of eclosion (0=no eye, 4=almost normal eye) (FIG. 13C). The number of absent eyes decreased upon the GSE treatment (right) in the same trial (FIG. 13D).
GSE Treatment Extends the Lifespan of elav>httQ3 *Drosophila*.
GSE treated elav>Q93httexon1 flies were found characterized by a significant increase in overall lifespan compared to untreated controls (FIG. 14). On average, 50% of elav>Q93httexon1 males on control food died by day 20, compared to only 20% of those on GSE.

The above results show that GSE treatment suppresses two distinct *Drosophila* models of neurodegeneration involving protein aggregation in vivo. The findings suggest that GSE may have therapeutic value for the prevention and/or treatment of protein aggregation-prone neurodegenerative disorders.

Example 6

Effects of Grape Seed Extract on Aβ Self-Assembly and Cytotoxicity

The present example provides evidence of the effects of a composition, according to one embodiment of the present invention, for reducing the self-assembly and cytotoxicity of Aβ.

Materials and Methods

Chemicals and Reagents.
Chemicals were obtained from Sigma-Aldrich Co. (St. Louis, Mo.) and were of the highest purity available. Medysin #1 ("Med1") was obtained from Aurora Fine Chemicals Ltd., Graz, Austria. MegaNatural-AZ (MNG-AZ) was obtained from Polyphenolics (Madera, Calif.). (Both MNG-AZ and Med1 are sometimes referred to as "compound" when mentioned in their mixtures with Aβ) Water was double-distilled and deionized using a Milli-Q system (Millipore Corp., Bedford, Mass.).
Peptides and Proteins.
Aβ peptides were synthesized, purified, and characterized as described previously (Walsh, et al., *J Biol Chem* 1997; 272: 22364-22372). Briefly, synthesis was performed on an automated peptide synthesizer (model 433A, Applied Biosystems, Foster City, Calif.) using 9-fluorenylmethoxycarbonyl-based methods on pre-loaded Wang resins. Peptides were purified using reverse-phase high-performance liquid chromatography (RP-HPLC). Quantitative amino acid analysis and mass spectrometry yielded the expected compositions and molecular weights, respectively, for each peptide. Purified peptides were stored as lyophilizates at −20° C. A stock solution of glutathione S-transferase (GST; Sigma-Aldrich, St. Louis, Mo.) was prepared by dissolving the lyophilizate to a concentration of 250 µM in 60 mM NaOH. Prior to use, aliquots were diluted 10-fold into 10 mM sodium phosphate, pH 7.4.

Preparation of Stock Solutions of Aβ.

Aggregate-free stock solutions of Aβ were prepared using size-exclusion chromatography (SEC). The nominal monomer fraction has been termed low molecular weight (LMW) Aβ because at experimental peptide concentrations this fraction comprises a mixture of monomer and low molecular oligomers in rapid equilibrium. To prepare Aβ, 200 µl of a 2 mg/ml (nominal concentration) peptide solution in dimethylsulfoxide were sonicated for 1 min using a bath sonicator (Branson Ultrasonics, Danbury, Conn.) and then centrifuged for 10 min at 16,000×g. The resulting supernate was fractioned on a Superdex 75 HR column using 10 mM phosphate buffer, pH 7.4, at a flow rate of 0.5 ml/min. The middle of the Aβ peak was collected during 50 s and used immediately for all experiments. A 10 µl aliquot was taken for amino acid analysis to determine quantitatively the peptide concentration in each preparation. Typically, the concentrations of $A\beta_{1-40}$ and $A\beta_{1-42}$ were 30-40 µM and 10-20 µM, respectively.

Aβ Incubation.

Aβ samples were prepared as specified above, and then 0.5 ml aliquots were placed in 1 ml microcentrifuge tubes. Test compounds were dissolved in ethanol to a final concentration of 2.5 mM and then diluted with 10 mM phosphate, pH 7.4, to produce concentrations of 10 and 50 µM. One-half ml of each compound then was added to separate tubes of Aβ, yielding final peptide concentrations of ~20 µM ($A\beta_{1-40}$) and ~10 µM ($A\beta_{1-42}$) and final inhibitor concentrations of 5 and 25 µM. Compound:peptide ratios thus were ~1:4 ($A\beta_{1-40}$) and ~1:2 ($A\beta_{1-42}$) at the lower compound concentration and 5:4 ($A\beta_{1-40}$) and 5:2 ($A\beta_{1-42}$) at the higher compound concentration. Control tubes with peptide alone received 0.5 ml of buffer. The tubes were incubated at 37° C. for 0-7 d without agitation.

Chemical Cross-Linking and Oligomer Frequency Distributions.

Immediately after their preparation, samples were cross-linked using the PICUP technique. Briefly, to 18 µl of protein solution were added 1 µl of 1 mM Ru(bpy) and 1 µl of 20 mM ammonium persulfate (APS). The final protein:Ru(bpy):APS molar ratios of $A\beta_{1-40}$ and $A\beta_{1-42}$ were 0.29:1:20 and 0.16:1:20, respectively. The mixture was irradiated for 1 sec with visible light and then the reaction was quenched with 10 µl of Tricine sample buffer (Invitrogen, Carlsbad, Calif.) containing 5% β-mercaptoethanol. Determination of the frequency distribution of monomers and oligomers was accomplished using SDS-PAGE and silver staining Briefly, 20 µl of each cross-linked sample was electrophoresed on a 10-20% gradient tricine gel and visualized by silver staining (SilverXpress, Invitrogen). Non-cross-linked samples were used as controls in each experiment. To produce intensity profiles and calculate the relative amounts of each oligomer type, densitometry was performed and One-Dscan software (v. 2.2.2; BD Biosciences Bioimaging, Rockville, Md.) was used to determine peak areas of baseline corrected data. In some experiments, the molar amounts of Ru(bpy) and APS were increased, relative to peptide, by factors of 2, 5, 10, and 20.

CD Spectroscopy.

CD spectra of Aβ solutions were acquired immediately after sample preparation or following 2, 3, 6, or 7 days of incubation. CD measurements were made by removing a 200 µL aliquot from the reaction mixture, adding the aliquot to a 1 mm path length CD cuvette (Hellma, Forest Hills, N.Y.), and acquiring spectra in a J-810 spectropolarimeter (JASCO, Tokyo, Japan). The CD cuvettes were maintained on ice prior to introduction into the spectrometer. Following a temperature equilibration, CD spectra were recorded at 22° C. from ~190-260 nm at 0.2 nm resolution with a scan rate of 100 nm/min. Ten scans were acquired, and the data were averaged for each sample. Raw data were processed by smoothing and subtraction of buffer spectra according to the manufacturer's instructions.

Thioflavin T (ThT) Binding Assay.

A ten µL of sample was added to 190 µL of ThT dissolved in 10 mM phosphate buffer (pH 7.4), and the mixture was vortexed briefly. Fluorescence was determined three times at intervals of 10 seconds using a Hitachi F-4500 fluorometer. Excitation and emission wavelengths were 450 and 482 nm, respectively. Sample fluorescence was determined by averaging the three readings and subtracting the fluorescence of a ThT blank.

Electron Microscopy (EM).

A 10 µl aliquot of each sample was spotted onto glow-discharged, carbon-coated Formvar grids (Electron Microscopy Sciences, Hatfield, Pa.) and incubated for 20 minutes. The droplet was then displaced with an equal volume of 2.5% (v/v) glutaraldehyde in water and incubated for an additional 5 minutes. Finally, the peptide was stained with 8 µl of 1% (v/v) filtered (0.2 µm) uranyl acetate in water (Electron Microscopy Sciences, Hatfield, Pa.). This solution was wicked off and the grid was air-dried. Samples were examined using a JEOL CX100 transmission electron microscopy.

3-[4,5-dimethylthiazol-2-yl]-2,5-diphenyltetrazolium bromide (MTT) Metabolism.

Rat pheochromocytoma PC12 cells were cultured in 75 cm² flasks (#430641, Corning Inc., Corning, N.Y.) in F-12K medium (ATCC, Manassas, Va.) containing 15% (v/v) horse serum, 2.5% (v/v) fetal bovine serum, 100 units/ml penicillin, 0.1 mg/ml of streptomycin, and 25 µg/ml amphotericin B at 37° C. with 5% (v/v) $CO_2$ in air. To prepare cells for assay, the medium was removed and the cells were washed once gently with F-12K medium, containing 0.5% (v/v) fetal bovine serum, 100 units/ml penicillin, 0.1 mg/ml of streptomycin, and 25 µg/ml amphotericin B. A cell suspension was then prepared by addition of this latter medium, but containing 100 µg/ml of nerve growth factor (Invitrogen, CA), followed by agitation of the flask. Following cell counting using trypan blue, cells were plated at a density of 30,000 cells/well (90 µl total volume/well) in 96-well assay plates (Costar #3610, Corning Inc., Corning, N.Y.). The nerve growth factor-induced differentiation of the cells was allowed to proceed for 48 h, at which point toxicity assays were conducted.

Aβ toxicity was assessed in two ways. Peptides were pre-incubated either with 0 or 25 µM of MNG-AZ in 10 mM sodium phosphate, pH 7.4 at 37° C. for 0, 2, 3, or 7 days, at which time 10 µl of the peptide solution was added to the wells. Alternatively, Aβ was incubated as described above, but in the absence of MNG-AZ. In this case, the peptide solutions were mixed with 0 or 25 µM MNG-AZ immediately before addition to cells. Cells were treated for 24 h with a final concentration of 0 or ~2 µM Aβ-only or MNG-AZ treated Aβ containing 2.5 µM of MNG-AZ. Peptide/compound ratios for $A\beta_{1-40}$ and $A\beta_{1-42}$ peptides were 0.72 and 0.39, respectively. In practice, the "zero time" samples for each alternative experimental procedure were equivalent, as all components were mixed with cells at the same time.

To determine toxicity, 15 µl of MTT solution (Promega, Madison, Wis.) was added to each well and the plate was kept in a $CO_2$ incubator for an additional 3.5 hours. The cells then were lysed by the addition of 100 µl of solubilization solution (Promega, Madison, Wis.) followed by overnight incubation. MTT reduction was assessed by measuring absorption at 570 nm (corrected for background absorbance at 630 nm) using a BioTek Synergy HT microplate reader (Bio-Tek Instruments, Winooski, Vt.). Controls included media with sodium phosphate ("negative"), fibrils ("positive"), and 1 µM staurosporine ("maximal positive"). Fibrillar $A\beta_{1-40}$ and $A\beta_{1-42}$ were added to cells at final concentrations of 10 µM and 5 µM, respectively. The same fibril preparations were used for all experiments and served to control inter-assay variability. To enable inter-assay comparisons, toxicity within each experiment was determined first. Six replicates were done for each treatment group and the data from 3 independent experiments were combined and reported as mean±S.E. Percent toxicity $T=((A_{A\beta}-A_{medium})/(A_{staurosporine}-A_{medium}))\times 100$; where $A_{A\beta}$, $A_{medium}$, $A_{staurosporine}$ were absorbance values from $A\beta$-containing samples, medium alone, or staurosporine alone, respectively.

Statistical Analysis.

One-way fractional ANOVA and multiple comparison tests were used for statistical analysis were conducted using the statistical procedures of GraphPad Prism (version 4.0a, GraphPad Software, Inc., San Diego, Calif.). A p-value<0.05 was considered significant.

Results and Discussion $A\beta$ Oligomerization.

In the absence of PICUP cross-linking, only $A\beta_{1-40}$ monomers (FIG. 15A, lane 2) and $A\beta_{1-42}$ monomers and trimers (FIG. 15B, lane 2) were observed. The $A\beta_{1-42}$ trimer band has been shown to be an SDS-induced artifact. Following cross-linking, $A\beta_{1-40}$ existed as a mixture of monomers and oligomers of order 2-4 (FIG. 15A, lane 3) whereas $A\beta_{1-42}$ contained monomers and oligomers of order 2-6 (FIG. 15B, lane 3).

When MNG-AZ was mixed with $A\beta_{1-40}$ at a compound: peptide ratio of ~5:4, oligomerization was blocked almost completely (FIG. 15A, lane 6). A trimer band was just visible and the dimer intensity was also minimal. Increasing the compound:peptide ratio ten-fold produced similar levels of inhibition (FIG. 15A, lane 7). The effect of MNG-AZ on $A\beta_{1-42}$ oligomerization was equally significant (FIG. 15B). At a compound:peptide ratio of ~5:2, MNG-AZ produced oligomer distributions almost identical to those of untreated $A\beta_{1-42}$, consistent with an essentially complete inhibition of oligomerization (cf. lanes 6 (treated) and 2 (untreated) of FIG. 15B). Increasing the compound:peptide ratio ten-fold produced similar levels of inhibition (FIG. 15B, lane 7). These data suggest that essentially complete inhibition of $A\beta$ oligomerization can be achieved at compound:peptide ratios of ~5:2 or lower.

As a compound control, Med1, an inactive polycyclic molecule with a structure distinct from that of MNG-AZ was used. As shown in FIGS. 15A and 15B, lanes 4, the oligomerization of $A\beta_{1-40}$ and $A\beta_{1-42}$ in the presence of Med1 produced oligomer distributions indistinguishable from those of each peptide alone. Increasing the compound:peptide ratio ten-fold showed similar oligomer distributions (FIGS. 15A and 15B, lanes 5).

Figure 15:
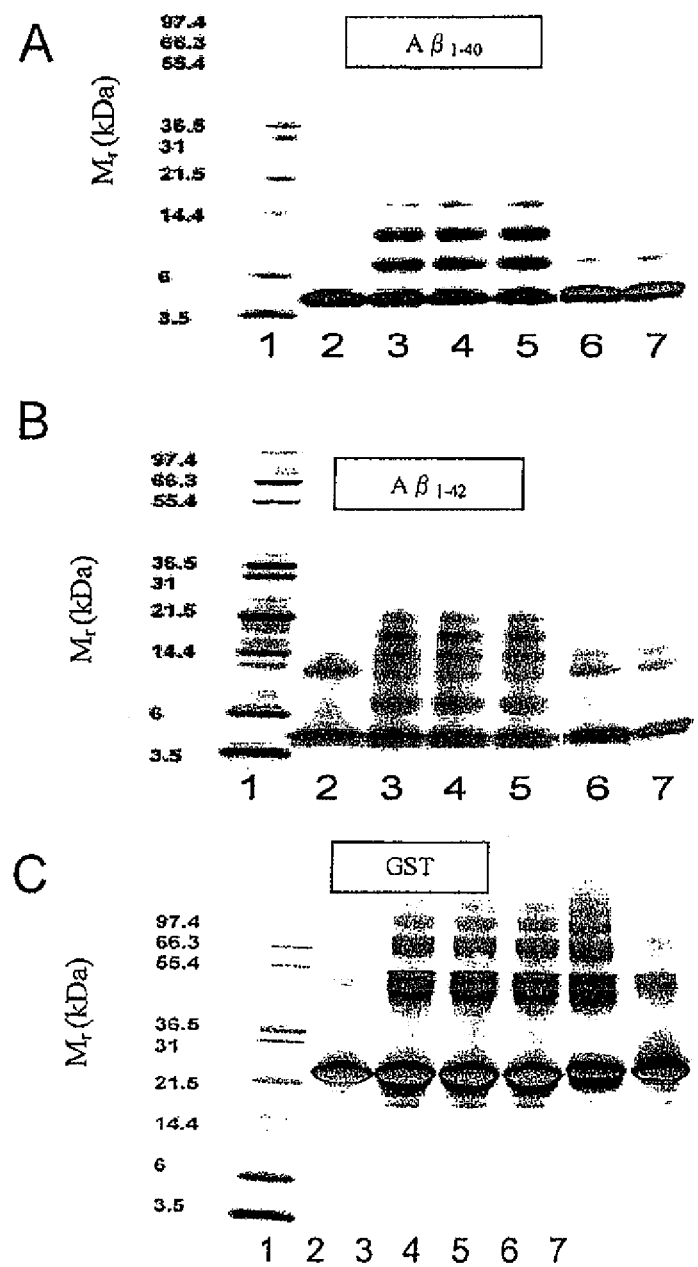
FIG. 15 illustrates the effect of MNG-AZ GSE on the Aβ oligomerization.

It was previously considered possible that the strong inhibition of $A\beta$ oligomerization could have resulted from an effect of the inhibitor on the PICUP chemistry itself. To evaluate this possibility, cross-linking reactions also were performed on glutathione-S-transferase (GST; ~26 kDa), a positive control for the cross-linking chemistry. Un-crosslinked GST exhibited an intense monomer band and a relatively faint dimer band (FIG. 15C, lane 2). Cross-linking produced an intense dimer band, expected because GST exists normally as a homodimer, as well as higher-order cross-linked species. No alterations in GST cross-linking were observed in the presence of Med1 at either of the two compound:protein ratios tested, 1:1 (FIG. 15C, lane 4) or 10:1 (FIG. 15C, lane 5). A qualitatively similar distribution was also observed with MNG-AZ at a 1:1 ratio (FIG. 15C, lane 6). A significant MNG-AZ effect on GST oligomerization was observed only at a 10:1 ratio, which was 4-8 times higher than the highest concentration ratio used in experiments with $A\beta$. This effect may have been due to direct compound:GST effects or to effects on the chemistry. However, a chemistry effect cannot explain the strong inhibition of $A\beta_{1-40}$ and $A\beta_{1-42}$ oligomerization, and the lack of strong inhibition of GST oligomerization, seen in lanes 6 of FIG. 15 (nor inhibitory activity in other assays). This provides strong evidence that MNG-AZ potently inhibited both $A\beta_{1-40}$ and $A\beta_{1-42}$ oligomerization.

Circular Dichroism Spectra.

Figure 3:
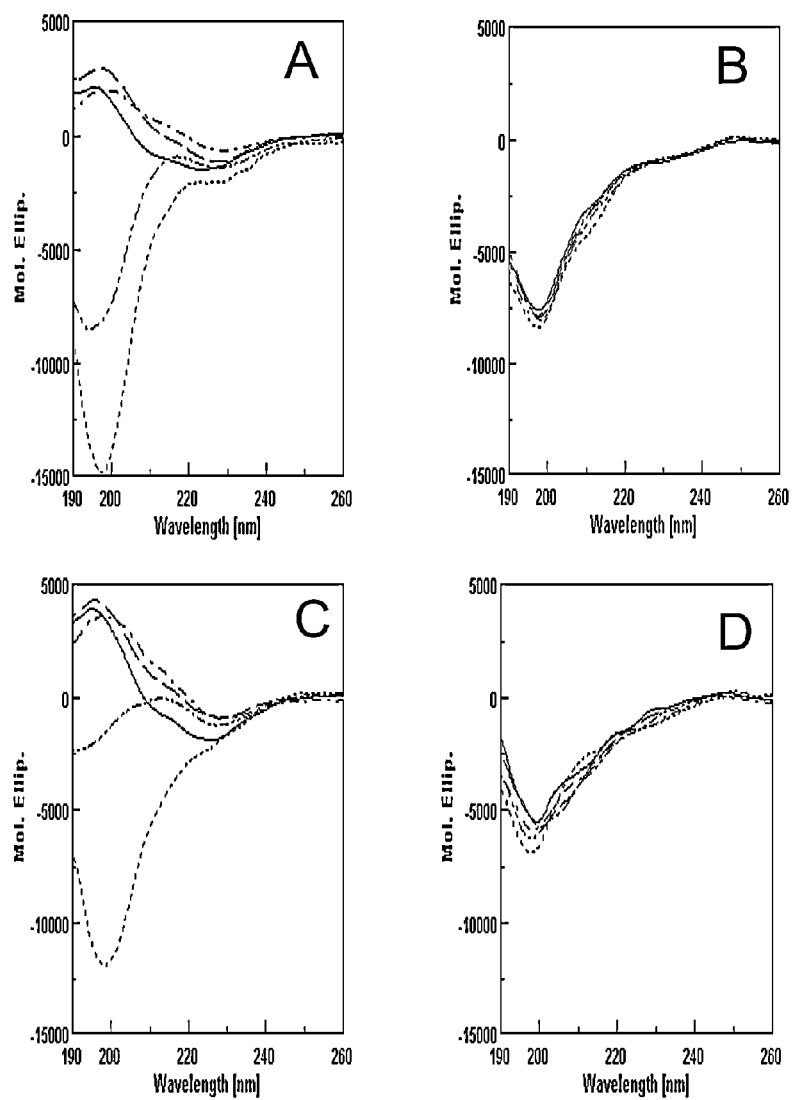
FIG. 3 presents the Aβ inhibiting effect of MNG-AZ as investigated by Circular Dichroism (CD) spectroscopy.

The effect of MNG-AZ on the secondary structure of $A\beta$ and its oligomers was investigated by CD spectra (FIG. 3). $A\beta_{1-40}$ and $A\beta_{1-42}$, when incubated alone, produced initial spectra characteristic of largely disordered conformers (FIGS. 3A and 3C). The major feature of these spectra was a large magnitude minimum centered at ~198 nm. During the subsequent three days of incubation, a large conformational transition occurred that eventually yielded a population of mixed α-helix and β-sheet character (see inflections at ~195, ~210, and ~220 nm). In contrast, no transitions were observed in the presence of MNG-AZ (FIGS. 3B and 3D). All spectra of MNG-AZ treated $A\beta_{1-40}$ and $A\beta_{1-42}$ revealed populations of conformers that were largely disordered, indicating that MNG-AZ successfully impeded the formation of secondary structures, especially β-sheets, of $A\beta$, which is implicated in the abnormal aggregation of $A\beta$.

ThT Binding.

Figure 4:
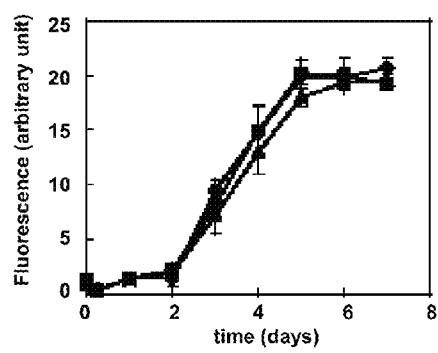
FIG. 4 presents Aβ inhibiting effect of MNG-AZ as investigated by ThT binding assay.
Figure 4:
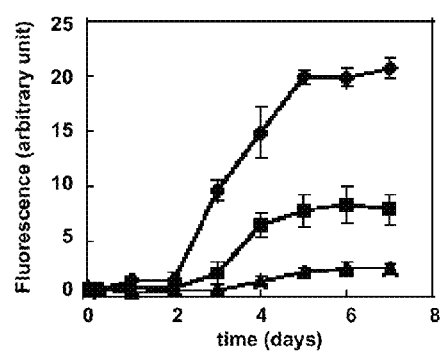
Figure 4:
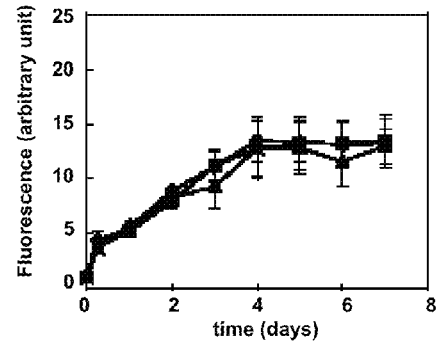
Figure 4:
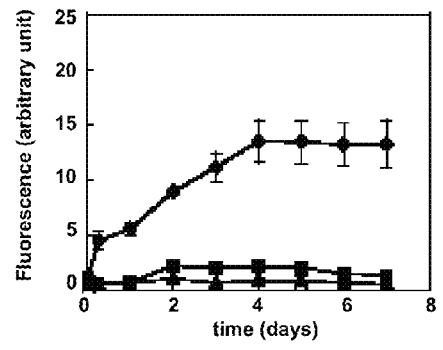

ThT binding was used to determine the level of β-sheet structure in preparations of $A\beta_{1-40}$ and $A\beta_{1-42}$. In the absence of compounds, $A\beta_{1-40}$ displayed a quasi-sigmoidal binding curve characterized by about 2-day lag period, and approximately a 3-day period of successively increasing ThT binding (correlated with fibril formation), with a binding plateau after about 5 days (FIG. 4). When $A\beta_{1-40}$ was incubated with Med1, either at a compound:peptide ratio of 1:4 or 5:4, the binding curves were identical to that of the untreated peptide, within experimental error (FIG. 4A). In contrast, significant effects were produced by MNG-AZ (FIG. 4B). These included MNG-AZ concentration-dependent increases in lag time, decreases in β-sheet growth rates, and decreased final β-sheet levels (Table 1). Almost complete inhibition of $A\beta_{1-40}$ assembly was observed using the higher (25 µM) MNG-AZ concentration.

TABLE 1

Kinetics of $A\beta$ assembly

| Sample | Lag time (d)[a] | Growth Rate (FU/d)[b] | Maximum Intensity (FU)[c] |
|---|---|---|---|
| $A\beta_{1-40}$ | 1.6 | 6.1 | 20.7 |
| $A\beta_{1-40}$ + 5 µM Med1 | 1.6 | 6.1 | 20.2 |
| $A\beta_{1-40}$ + 25 µM Med1 | 1.6 | 5.4 | 19.5 |
| $A\beta_{1-40}$ + 5 µM MNG-AZ | 1.8 | 2.6 | 8.3 |
| $A\beta_{1-40}$ + 25 µM MNG-AZ | 2.4 | 0.8 | 2.5 |
| $A\beta_{1-42}$ | 0 | 2.5 | 13.5 |
| $A\beta_{1-42}$ + 5 µM Med1 | 0 | 2.5 | 13.5 |
| $A\beta_{1-42}$ + 25 µM Med1 | 0 | 2.3 | 13.1 |
| $A\beta_{1-42}$ + 5 µM MNG-AZ | 0 | 1.0 | 2.2 |
| $A\beta_{1-42}$ + 25 µM MNG-AZ | >7 | 0 | 1.0 |

Untreated $A\beta_{1-42}$ and Med1-treated samples assembled similarly to that of $A\beta_{1-40}$. (FIG. 4C). Within the time resolution of the assay, little or no lag time was observed in the development of fluorescence, which increased in a quasilinear manner for 4 days and then remained constant. The effect of MNG-AZ on $A\beta_{1-42}$ assembly was even greater than that on $A\beta_{1-40}$ assembly. When $A\beta_{1-42}$ was incubated with MNG-AZ at a compound:peptide ratio of 1:2, a 1 day lag was observed and maximal ThT binding, which occurred only 1 day later, was six-fold lower than that of the untreated peptide (FIG. 4D; Table 1). However, at a compound:peptide ratio of 5:2, no β-sheet formation was observed. Therefore, MNG-AZ inhibited β-sheet formation by both $A\beta_{1-40}$ and $A\beta_{1-42}$ in a concentration-dependent manner and the inhibition was significantly more effective for $A\beta_{1-42}$.

EM Results.

Figure 5:
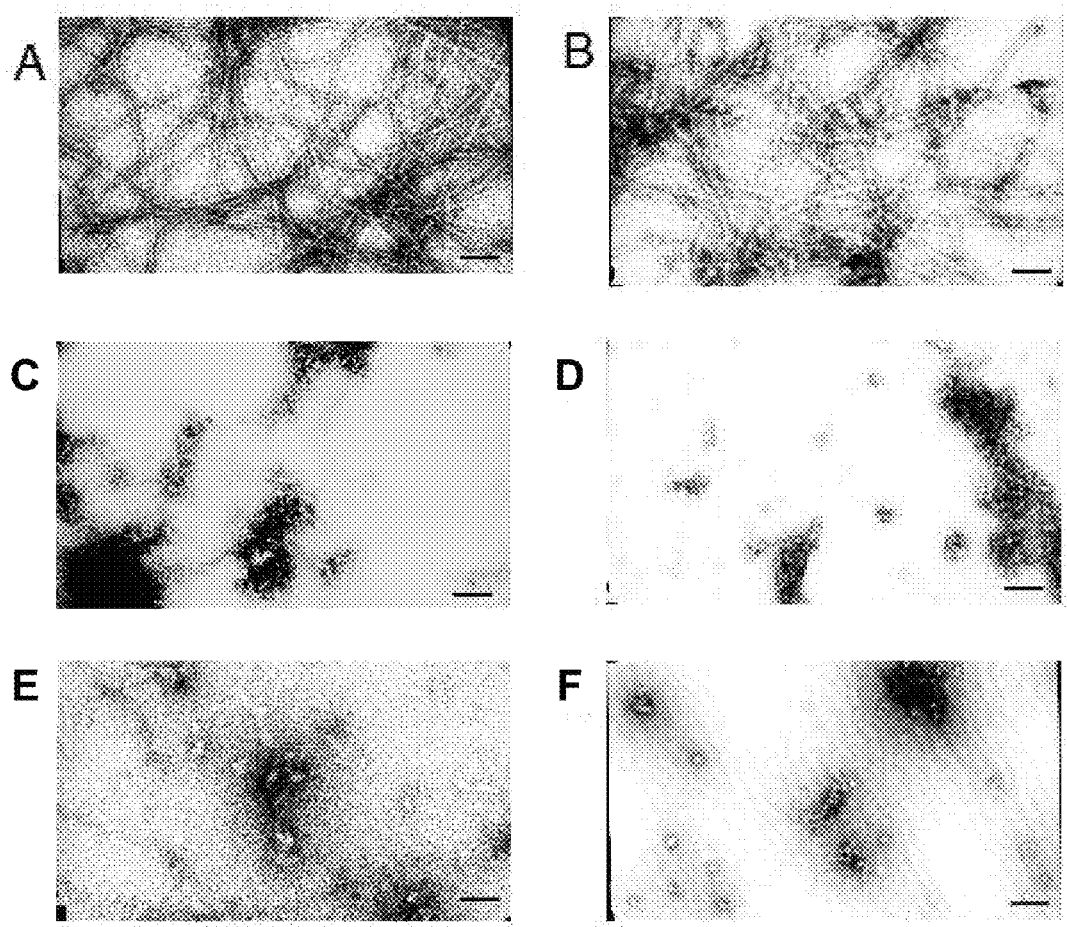
FIG. 5 illustrates Aβ inhibiting effect of MNG-AZ as investigated by electron microscopy.

Secondary structure parameters correlated with Aβ assembly state but they did not per se establish the quaternary structures of the assemblies, which are better observed by electron spectroscopy (FIG. 5). Classical amyloid fibrils were observed in samples of untreated $A\beta_{1-40}$ and $A\beta_{1-42}$ (FIGS. 5A and 5B, respectively). The $A\beta_{1-40}$ fibrils were non-branched, helical filaments with diameters of ~7 nm that exhibited a helical periodicity of ~220 nm. $A\beta_{1-42}$ formed non-branched filaments of ~8 nm in width and with varying degrees of helicity. In addition, thicker, straight, non-branched filaments ~12 nm width were observed for $A\beta_{42}$ assembly. At the lower (5 µM) MNG-AZ concentration, fibrils were thinner (4 vs. 8 nm) than those formed by untreated Aβ (FIG. 5C). In addition, numerous small, relatively amorphous aggregates were observed. Treatment of $A\beta_{1-40}$ with 25 µM MNG-AZ markedly reduced fibril number and increased the relative numbers of short fibrils and amorphous aggregates (FIG. 5E). The effects of MNG-AZ on $A\beta_{1-42}$ assembly were similar in that fibril number and length were reduced and the frequency of amorphous aggregates increased (FIGS. 5D and 5F).

MTT Metabolism (Toxicity Assay).

Figures 6A, 6B:
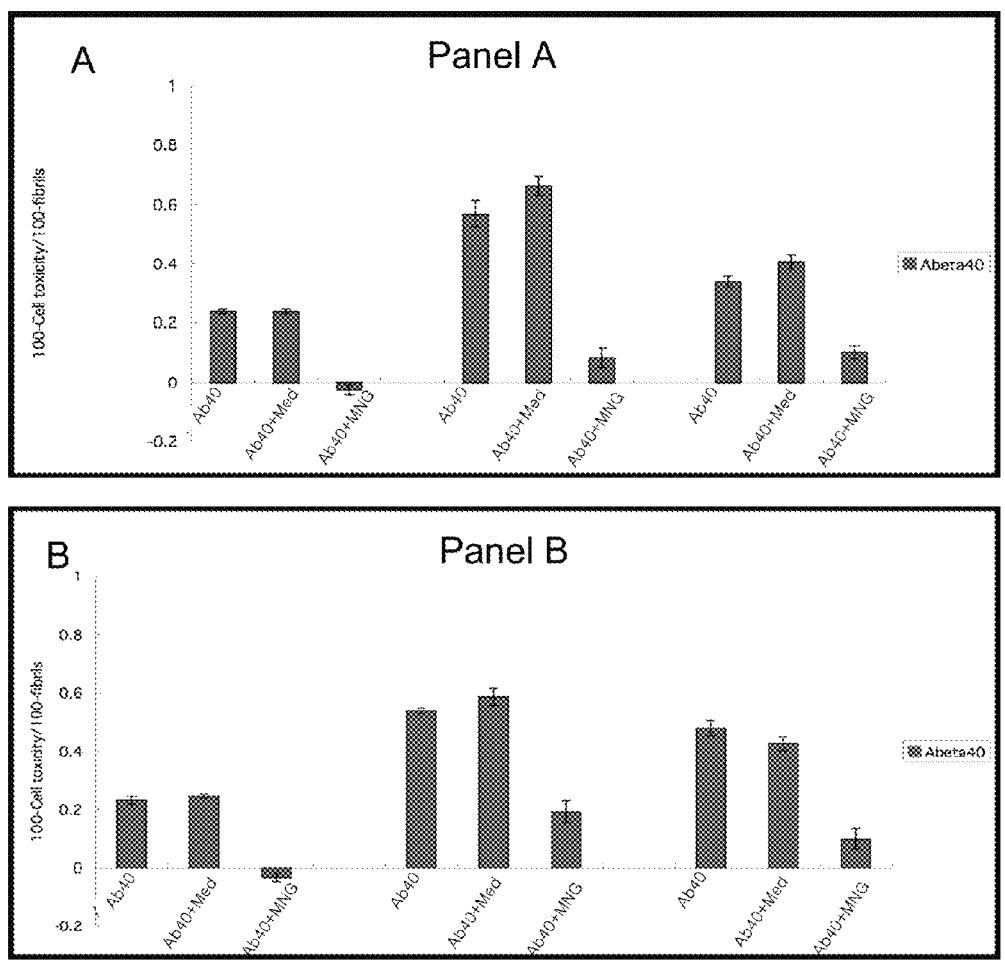
FIGS. 6A-6D.
Figure 6C:
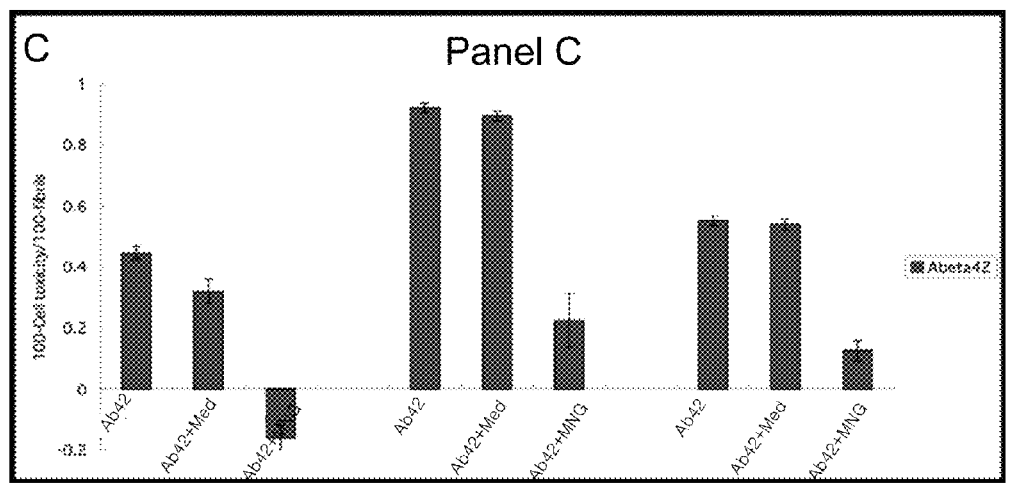
Figure 6D:
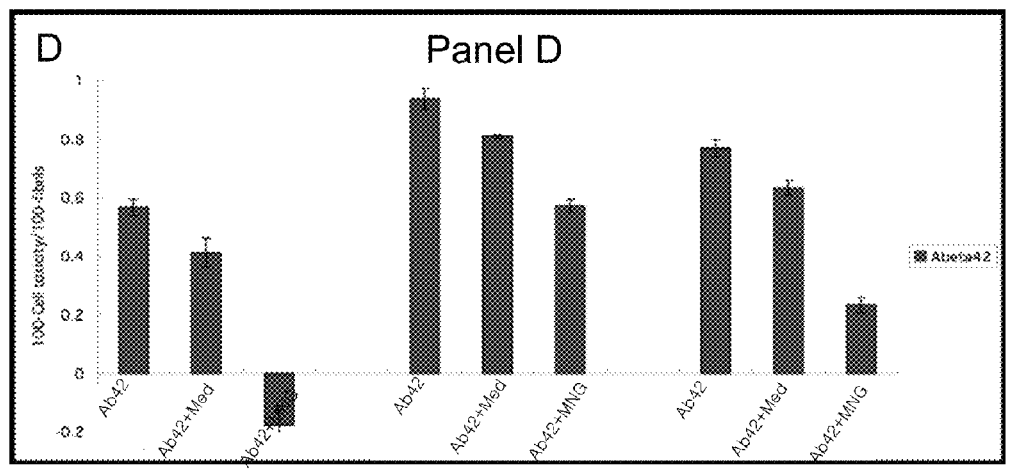

The results of the toxicity assay of Aβ are illustrated in FIG. 6. In FIGS. 6A-6D, the groups on the left represent toxicity results after 0 day incubation (for both peptides $A\beta_{1-40}$ and $A\beta_{1-42}$); the groups in the middle represent toxicity results after 3 days of incubation for $A\beta_{1-40}$ (FIGS. 6A and 6B) or 2 days of incubation for $A\beta_{1-42}$ (FIGS. 6C and 6D); the groups on the right represent toxicity results after 7 days of incubation (for both peptides). In one set of experiments (FIGS. 6A and 6C), the peptides were co-incubated with Med1 or MNG-AZ. In a second set of experiments (FIGS. 6B and 6D), Med1 and MNG-AZ were added following the incubations and immediately prior to addition of the mixtures to differentiated PC12 cells.

$A\beta_{1-40}$ was shown to be toxic to cells and the toxicity was ~20% that of fibrils (FIG. 6A). A mixture of $A\beta_{1-40}$ and Med1 also was ~20% toxic. In contrast, MNG-AZ rendered $A\beta_{1-40}$ non-toxic. Incubation of $A\beta_{1-40}$ for 3 days, during which time oligomers, protofibrils and fibrils form, produced a composition that was significantly more toxic (~60%, the middle group of FIG. 6A). Treatment of $A\beta_{1-40}$ with MNG-AZ reduced this toxicity to <10% (p<0.005). The same qualitative relationships among the three experimental groups was observed after 7-day incubation (the right group of FIG. 6A): both untreated and Med1-treated $A\beta_{1-40}$ were ~35-40% toxic, whereas MNG-AZ treated $A\beta_{1-40}$ was <10% toxic. Similar observations were made in experiments with $A\beta_{1-42}$ (FIG. 6C). $A\beta_{1-42}$ was more toxic than $A\beta_{1-40}$ at all time points.

The effects of MNG-AZ on $A\beta_{1-40}$ induced toxicity after peptide assembly progression are illustrated in FIG. 6B. At all three incubation times, untreated and Med1-treated peptide yielded similar toxicity levels. In contrast, MNG-AZ treated peptide was either non-toxic (0 day) or significantly less toxic (3 or 7 days). Qualitatively similar results were obtained in studies of $A\beta_{1-42}$ (FIG. 6D). The effects of MNG-AZ on $A\beta_{1-42}$ were more pronounced than the case of $A\beta_{1-40}$.

The above results consistently indicated that MNG-AZ effectively inhibited the oligomerization of Aβ and its toxicity in the brain. These findings are evidence that MNG-AZ can prevent or treat diseases associated with misfolding, accumulation, aggregation, or deposition of Aβ.

Example 7

In Vivo Effect of a Grape Seed Extract on Transgenic Drosophila and Mouse Models of Tauopathies The present example illustrates the in vivo benefits of a composition according to an embodiment of the present invention on Drosophila phenotypes carrying mutant tau (R406W), which model certain forms of tauopathy, and a transgenic JNPL3 mouse model of tauopathy.

Materials and Methods

Examination of Eye Phenotype of Ey>R406W Flies.

Figure 21:
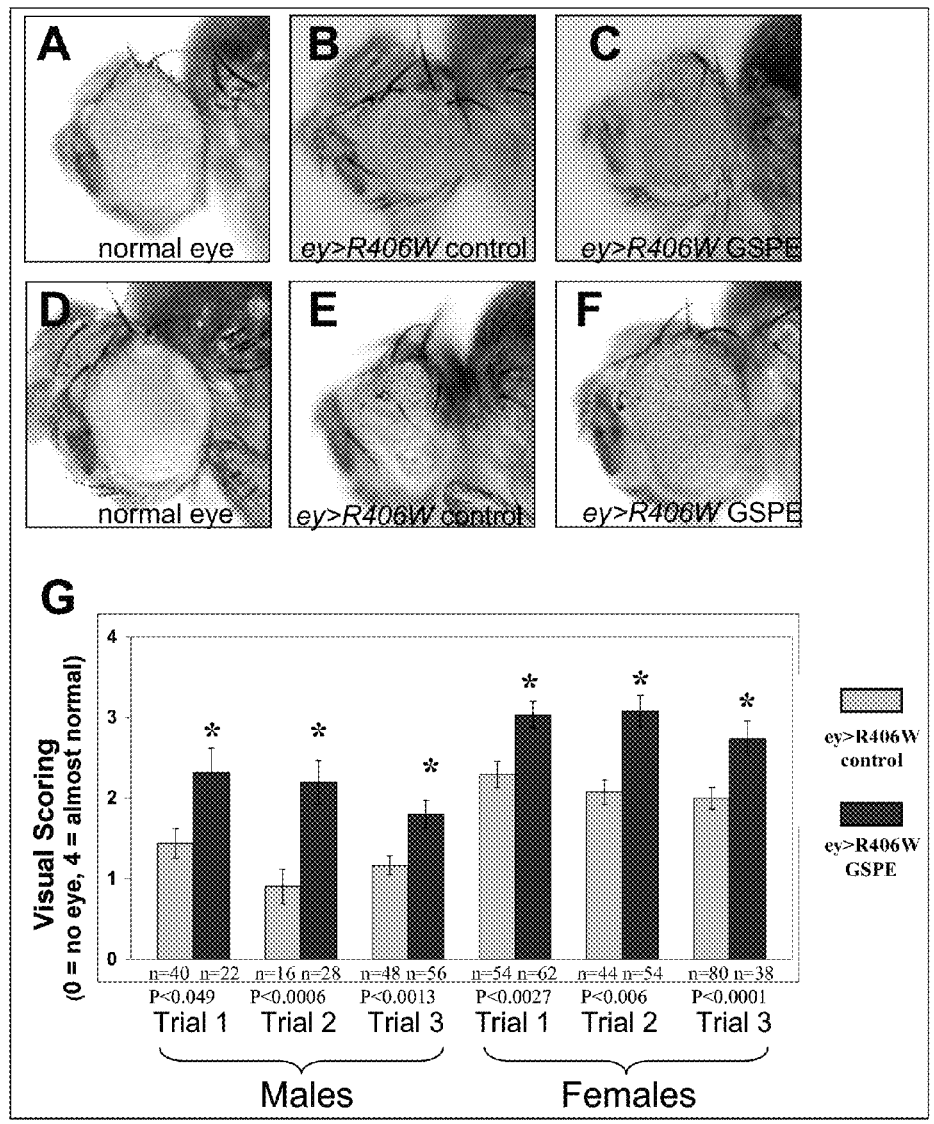
FIG. 21 illustrates the effect of MNG-AZ GSE on abnormal eye phenotypes of a mutant tau *Drosophila* model.

This study was a continuation of the study presented in Example 5. In brief, ey>R406W eggs were laid in and reared on 4-24 instant fly medium supplemented with 2.8 µg/ml MNG-AZ GSE (or GSPE, in FIG. 21) or control food supplemented with an equivalent volume of water (GSE solvent, vehicle control). Flies were treated with GSE (or vehicle) continuously into adulthood. The eyes of Drosophila were observed under microscope.

Evaluation of Motor Function Impairment and Mortality of JNPL3 Mice.

Figure 22:
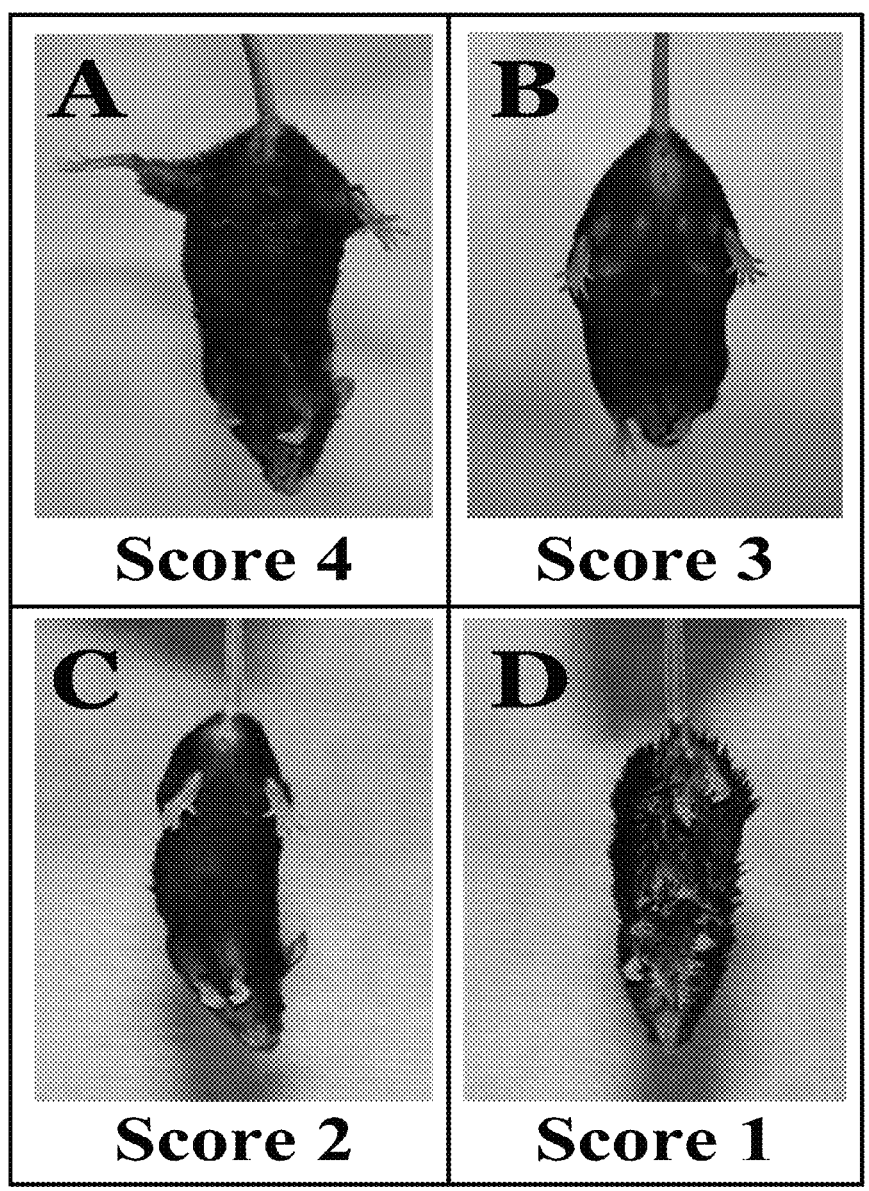
FIG. 22 illustrates an evaluation scheme using hind limb extension assay for a transgenic JNPL3 mouse model of tauopathy. The animals' natural tendency to extend their hind limbs laterally when they are hung inverted by their tails are assessed according to a four-point rating system: 4=normal function (FIG. 22A), 3=mild impairment (FIG. 22B), 2=moderate impairment (FIG. 22C), and 1=severe impairment (FIG. 22D).

The JNPL3 mouse model is engineered to express the human familial P301L mutant tau that leads to age-related neurodegeneration, which is reflected by motor dysfunction. JNPL3 mice were treated with 150 mg/kg BW/day of MNG-AZ GSE, starting at approximately seven months of age, which is prior to the initiation of mutant tau-mediated motor impairment that typically begins to develop by ~12 months of age. A hind limb extension test (illustrated in FIG. 22) was used to assess motor function impairment based on a four-point rating system.

Results and Discussions

GSE Treatment Suppressed Abnormal Eye Phenotypes in R406W Mutant Tau Flies.

Eyes from adult R406W mutant tau flies are characterized by reduced size and abnormal morphologies (FIGS. 21B and 21E) as compared to wild-type adult flies (FIGS. 21A and 21D). In contrast, the GSE-treated mutant tau flies exhibited much reduced abnormality in eye size (FIGS. 21C and 21F).

In a quantitative analysis of adult eye morphology using a four-point scoring system for eye changes in eye morphology where 0 denotes no eye and 4 denotes normal eye, GSE treatment was shown to significantly improve eye phenotypes in adult male and female R406W mutant tau flies across three independent trials (FIG. 21G) (ANOVA: P<0.0005, F=57.29; DF=1,531; *P<0.05, comparing GSE-treated vs. non-treated flies in individual trials).

GSE Treatment Attenuated Tauopathy Pre-Clinical Phenotypes in JNPL3 Mice.

Continued GSE treatment did not result in detectable adverse effects on the JNPL3 mice, including changes in body weight or water consumption (not shown). GSE treatment of JNPL3 mice reduced the severity of motor impairment that normally occurs with aging in this mouse model (FIG. 23A).

Figure 23:
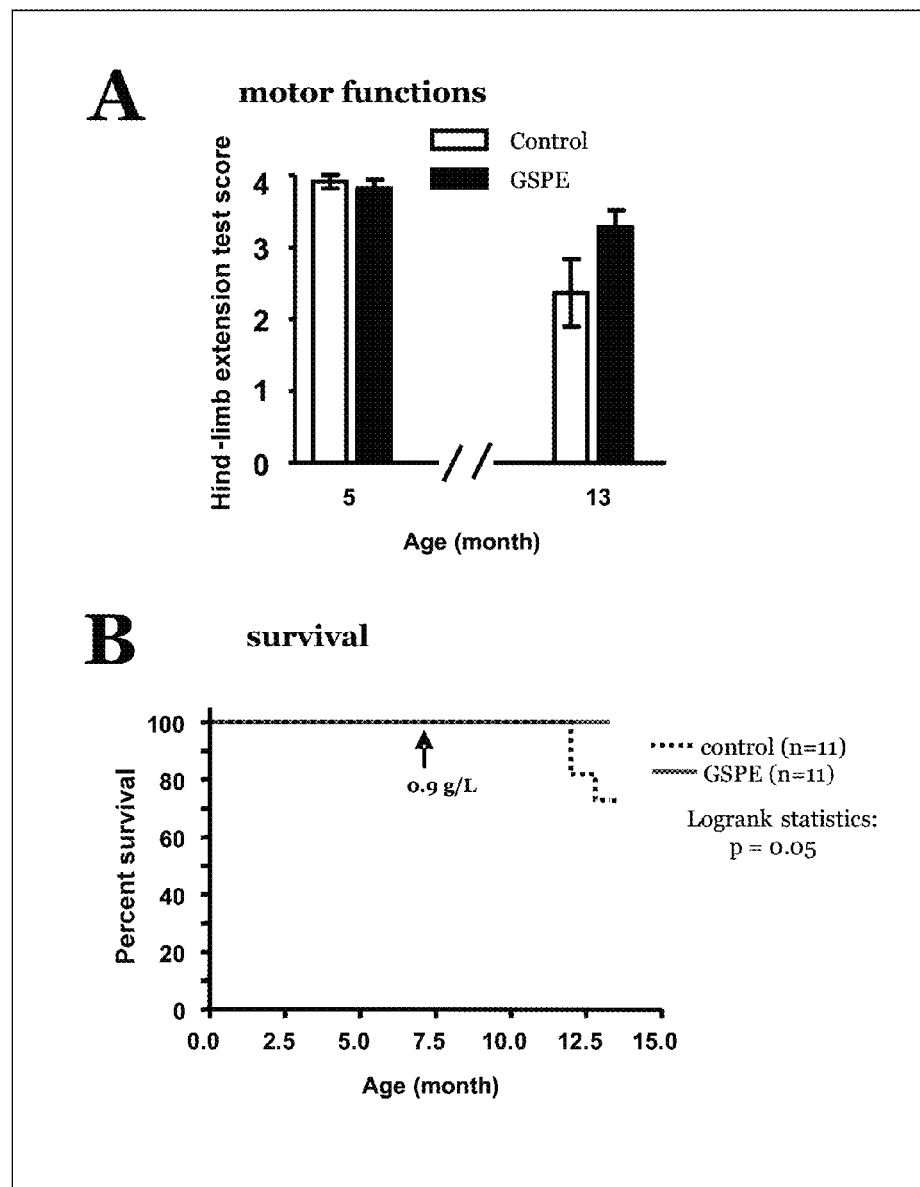
FIG. 23 illustrates the effect of a GSE treatment on a transgenic JNPL3 mouse model of tauopathy.

Coincidental to attenuating motor impairment, GSE treatment also significantly reduced mortality of JNPL3 mice relative to untreated JNPL3 control group (FIG. 23B shows that the mortality rate of JNPL3 mice was reduced by ~30% at 13 months) (Logrank statistics, p=0.05; mortality: untreated mice=27%, GSE treated mice=0%).

Collectively, the in vitro and in vivo evidence presented in Examples 4, 5 and 7 suggests that MNG-AZ GSE can beneficially modulate tau-mediated neuropathologic phenotypes by interfering with misfolding of tau into tau aggregates, which supports the potential application of the GSE to prevent and/or treat tau-related neurodegenerative disorders, including AD, Progressive Supranuclear Palsy, Corticobasal Degeneration, Argyrophilic Grain Disease, Pick's Disease, FTDP-17, etc. Moreover, the evidence that the GSE interferes with both Aβ-mediated (as illustrated in Examples 1-3 and 6) and tau-mediated neuropathologic mechanisms strongly support MNG-AZ's potential application in preventing and/or treating AD.

Example 8

In Vitro Effect of a Grape Seed Extract on Polyglutamine Htt-Mediated HD Neuropathologic Phenotypes The present example illustrates the in vitro effects of a composition according to an embodiment of the present invention on aggregation of a polyglutamine-containing htt protein species.

Materials and Methods

Figure 24:
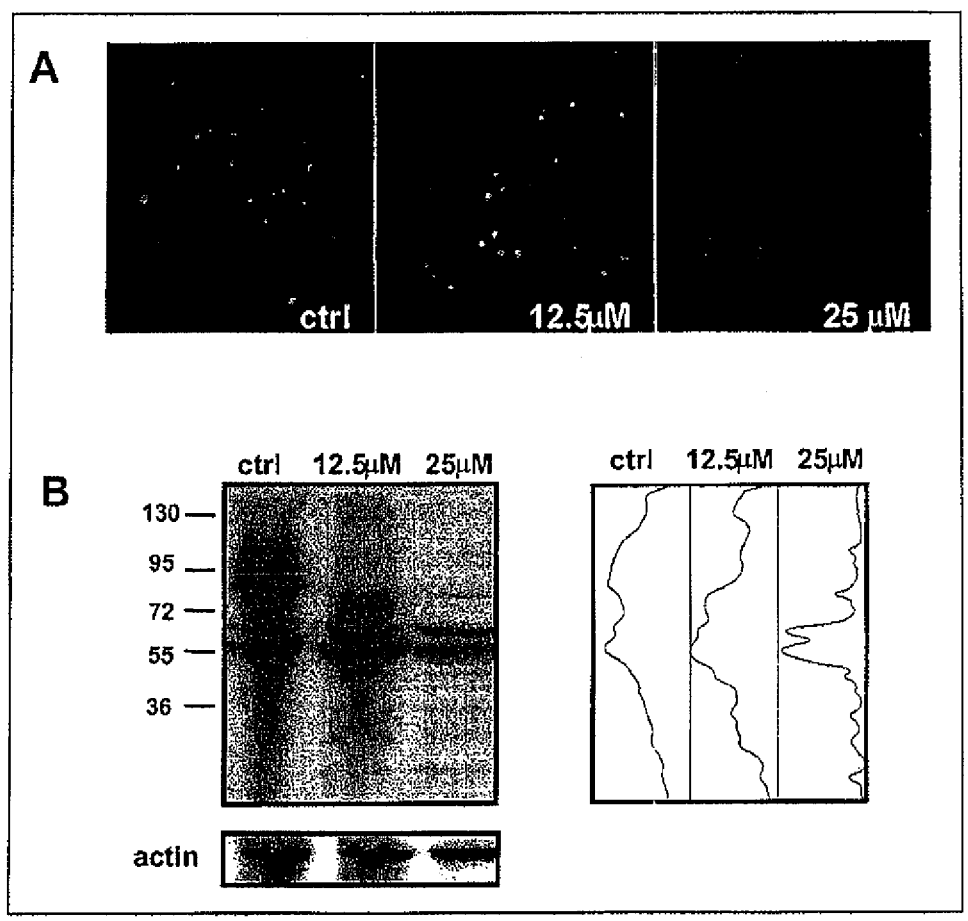
FIG. 24 illustrates the effect of MNG-AZ GSE in reducing aggregate of htt protein using fluorescence microscopy.

A htt protein species was obtained using a PC-12 cell line containing an ecdysone-inducible polyglutamine-containing Htt-fusion protein comprising the first 17 amino acid of htt protein plus 103 glutamines fused with enhanced GFP (Htt103Q-EGFP), which expresses the htt fusion protein upon induction with the ecdysone analogue, muristerone A, and form fluorescent htt aggregates (Apostol et al., *Proc Nat Acad Sci* 2003; 100:5950-5955). GFP-Htt fusion protein was induced by 0.2 µM muristerone A, and aggregation of the GFP-Htt fusion protein in the absence and presence of MNG-AZ GSE (12.5 µM and 25 µM) treatment was assessed by fluorescent microscopy and Western blot analysis. Accumulation of htt aggregates in the absence and presence of the GSE were reflected by fluorescence emission following the recruitment of GFP-Htt fusion protein into aggregates Results and Discussions GSE treatments significantly reduced the accumulation of fluorescent htt aggregates in a dose-dependent manner: higher dosage of GSE treatment resulted in more pronounced reduction of high molecular weight Htt aggregates (FIG. 24A). This result was also corroborated by an independent Western blot analysis (FIG. 24B).

The above results provide in vitro evidence that MNG-AZ may interfere with polyglutamine htt-mediated HD neuropathologic phenotypes.

Example 9

In Vivo Effect of a Grape Seed Extract on Transgenic *Drosophila* and Mouse Models of Huntington's Disease The present example illustrates the in vivo benefits of a composition according to an embodiment of the present invention on elav>Q93httexon1 *Drosophila* HD model, and R6/2 transgenic JNPL3 mouse model of HD.

Materials and Methods

Assessment of Motor Function and Mortality of HD Flies.

Elav>Q93Httexon1 *Drosophila* HD model was used in these studies. This HD model involves the elav-Gal4/UAS regulatory system to achieve selective, pan-neuronal over-expression of a truncated human mutant htt protein encoded by exon 1 of the human htt gene, which harbors a 93-polyglutamyl residues (Sang et al., *NeuroRx,* 2005; 2:438-446). This leads to adult onset neurodegeneration, including the disruption of photoreceptor cells of the eye, impairments of climbing ability, and reduced lifespan (Sang et al., 2005, supra).

In assessing motor impairment, adult elav>Q93httexon1 flies were collected within one day of eclosion (emergence of an adult fly from its pupal case) and placed 10 per vial on control food or MNG-AZ GSE-infused food (n=30 per group). On day 9 and day 16 respectively, motor activities were assessed by gently tapping flies to the bottom of the tube and monitor the percentage of flies successfully climbing up the tube to and beyond pre-determined heights (e.g., up to the 7 cm mark on day 9 or 2 cm mark on day 16) within 8 seconds. In assessing mortality rate, male Elav>Q93httexon1 flies were collected within one day of eclosion and placed 10 per vial on standard (control) food or GSE-infused food. Viable flies were counted daily.

Assessment of Motor Functions and Mortality of HD Mice.

These studies were conducted using the R6/2 mouse HD model originally generated by Dr. Bates and colleagues (Mangiarini et al. Cell, 1996; 87:493-506), which is the most commonly used transgenic mouse HD model. R6/2 mice express a htt exon 1 fragment that harbors a 148-153 polyglutamine repeats. The regulation of mutant htt is driven by the human htt promoter. The R6/2 mice exhibit a very aggressive neurological phenotype and provide clear experimental endpoints, which are ideal for preclinical feasibility study (Ramaswamy et al. *ILAR J,* 2007; 48:356-73).

Ovary transplanted female mice obtained from Jackson's Laboratories were randomly divided into two groups (100 mg/kg/day MNG-AZ GSE-treated and $H_2O$-treated control groups) and mated with wild-type male mice. The weaning pups were continuously fed on the same GSE or control treatment regimes.

Rotarod tests were used to assess the impact of GSE-treatment on changes in motor coordination in R6/2 mice during the age-related development and progression of HD phenotypes. HD transgenic mice were trained to stay on a narrow rod in an accelerating rotarod apparatus (4 rpm-40 rpm in 10 minutes) at 6 weeks of age, and rotarod performance was monitored once a week starting at 8 weeks of age. Three trials were conducted on each test given and the average of the three trials was recorded. Loss of motor function is reflected by reduced latency time before the animals fall off the apparatus. In assessing the mortality of R6/2 mice, the mice were treated either with 100 mg/kg/day MNG-AZ GSE, or $H_2O$ (control group), and survival rate was recorded every day.

Results and Discussions

Motor Function and Mortality in the *Drosophila* HD Model.

Figure 25:
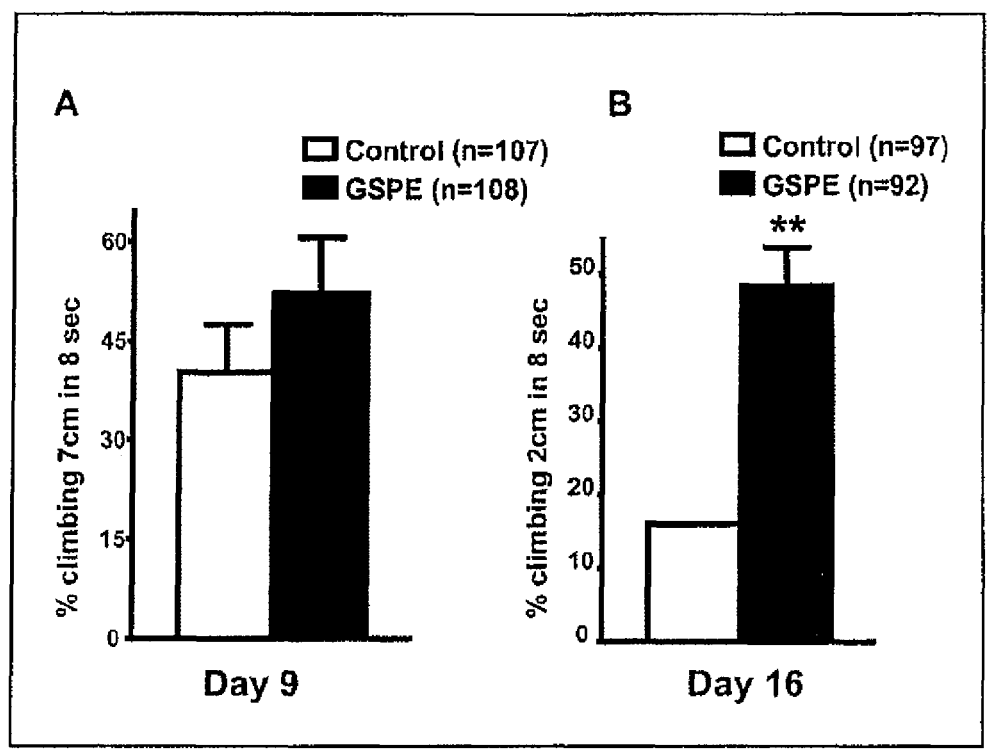
FIG. 25 illustrates the effect of a GSE treatment on motor impairments in a *Drosophila* HD model as assessed by a climbing assay.

When motor performance of elav>Q93httexon1 flies were assessed at day 9 when flies exhibited mild HD phenotypes, GSE treatment was found to improve motor performances in the climbing assay on day 9 (~40% of the control, non-treated flies and ~50% of the GSE-treated flies successfully accomplished the climbing task) (FIG. 25A). However, this observation did not reach statistical significance. When assessed at day 16 when elav>Q93httexon1 flies developed more severe motor impairment, significantly larger percentage of GSE-treated flies successfully accomplished the climbing task as compared to the control flies (~15% of the non-treated flies and ~47% of the GSE-treated flies successfully accomplished the climbing task) (FIG. 25B). These results suggest that the GSE exerts bioactivity in vivo and mitigates motor impairment in this *Drosophila* HD model.

Figure 26:
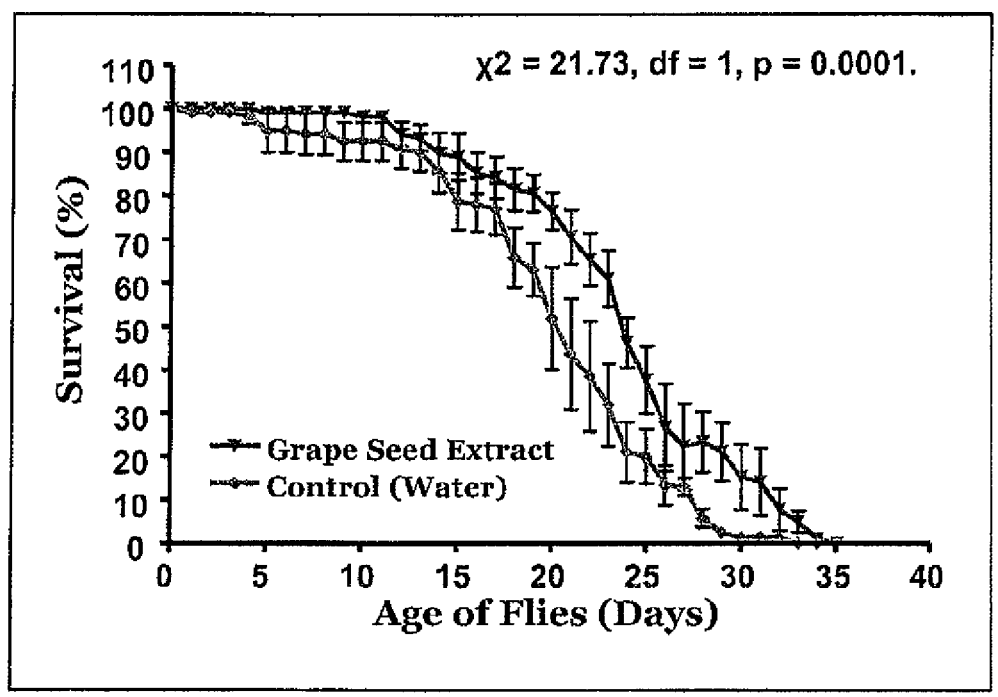
FIG. 26.

Aside from motor impairment, expression of mutant htt protein in this *Drosophila* HD model led to reduced life span. GSE treatment was continued (from that discussed in Example 5) to evaluate its impact in improving life span in this *Drosophila* model. Consistent with the previous observation that GSE treatment significantly reduced mutant Htt-mediated motor impairment (FIG. 25), GSE treatment also significantly promoted the life-span of elav>Q93httexon1 flies (Kaplan-Maier analysis of fly survival from all four trials demonstrated that GSE-treatment significantly promote lifespan in elav>Q93httexon1 flies: $\chi2=21.73$, df=1, p=0.0001) (FIG. 26).

Motor Functions and Mortality in the HD Mice.

Figure 27:
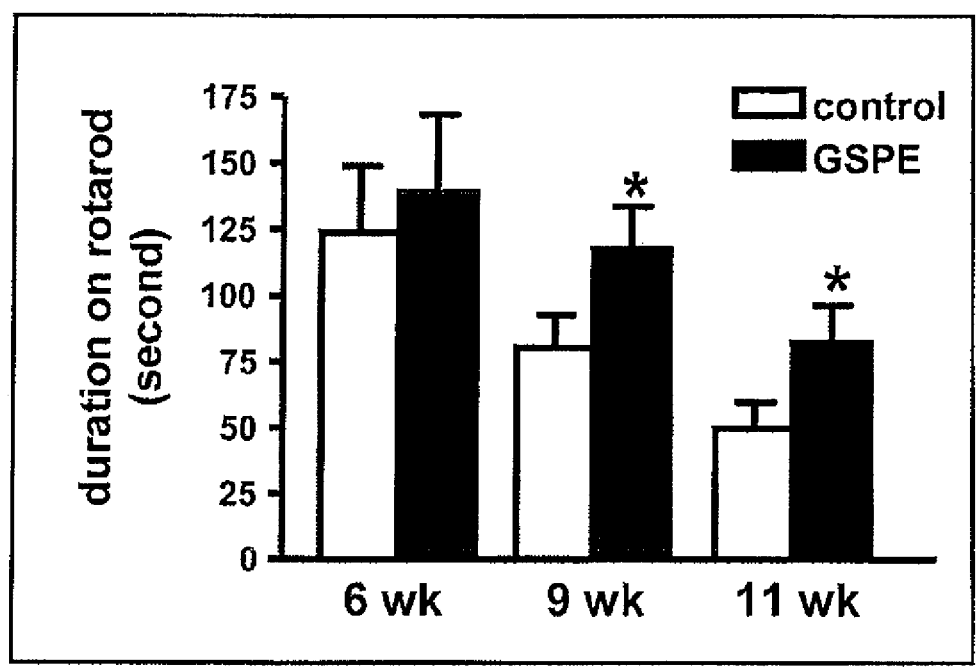
FIG. 27.

In the study of motor function of the R6/2 mice, no behavior difference was found between the control group and the GSE-treated group at 6 weeks of age, when the animals were mostly presymptomatic. Motor functions of the mice were continued to be examined at 9 weeks of age during the initiation of motor impairment, and at 11 weeks of age when HD phenotypes progressed to moderate motor impairments. GSE treatment significantly improved motor functions in R6/2 HD mice at both clinical disease initiation (at 9 weeks of age) and progression (at 11 weeks of age), as shown in FIG. 27 (bar graphs represent mean+SEM of the time (sec) animals were able to stay on the rotarod. Statistical analysis by Student's t-test, *p<0.05 comparing GSE-treated to control non-treated groups).

Figure 28:
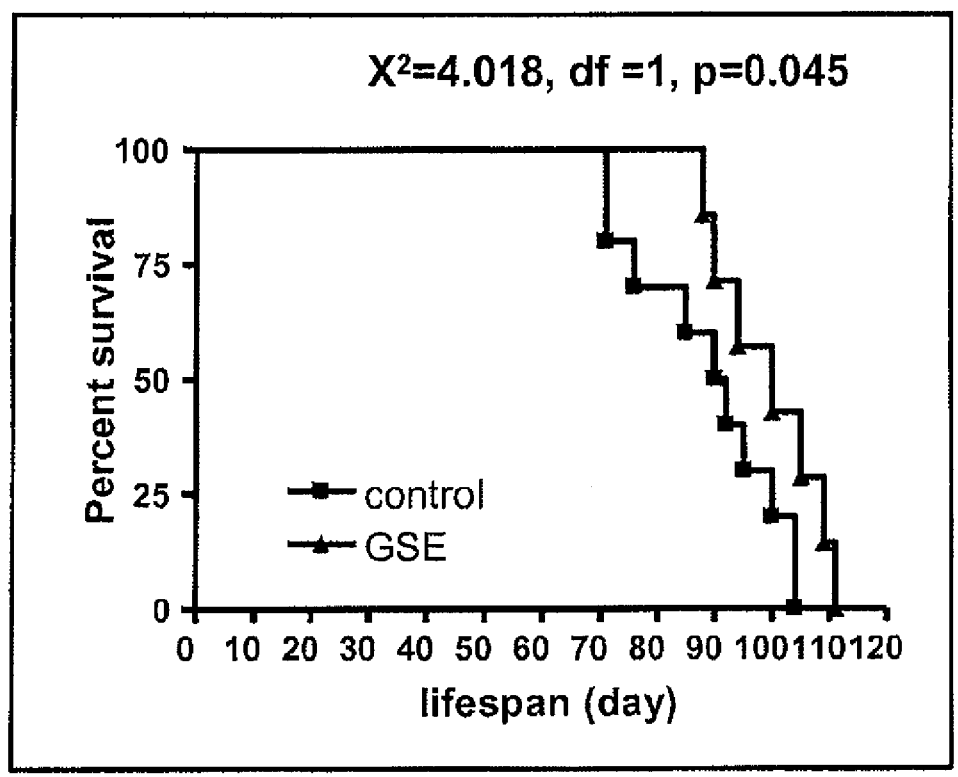
FIG. 28.

In the study of mortality of R6/2 mice, GSE treatment was found to significantly extend survival of R6/2 HD mice. The median lifespan for non-treated R6/2 mice was 90 days, while GSE treatment significantly increased the median lifespan of HD mice to 100 days (Kaplan-Maier analysis demonstrated that GSE-treatment significantly promote lifespan HD mice: X2=4.018, df=1, p=0.045) (FIG. 28).

Thus, the above in vivo studies using experimental HD models generated from independent, phylogenetically distant *Drosophila* and mouse species demonstrated the efficacy of the MNG-AZ GSE to attenuate mutant Htt-mediated pathologic phenotypes. Combining with the evidence from in vitro studies (discussed in Examples 5 and 8), these findings support the potential value of using the GSE in the prevention and/or treatment of HD.

All patents, patent applications, publications, product descriptions and protocols, cited in this specification are hereby incorporated by reference in their entirety. In case of a conflict in terminology, the present disclosure controls.

While it will be apparent that the invention herein described is well calculated to achieve the benefits and advantages set forth above, the present invention is not to be limited in scope by the specific embodiments described herein. It will be appreciated that the invention is susceptible to modification, variation and change without departing from the spirit thereof.

What is claimed is:

1. A method of treating a neurodegenerative disease of a subject, which method comprises administering to a subject in need thereof a composition comprising a grape seed extract having less than 12% by weight of galloylated proanthocyanidins based on the total weight of proanthocyanidins in the extract, wherein the composition is administered in an amount effective to reduce formation of Aβ oligomers, reduce aggregation of tau protein, reduce aggregation of htt protein, or combinations thereof.

2. The method of claim 1, wherein the neurodegenerative disease is Alzheimer's Disease.

3. The method of claim 1, wherein the neurodegenerative disease is Parkinson's Disease.

4. The method of claim 1, wherein the neurodegenerative disease is Huntington's Disease.

5. The method of claim 1, wherein the neurodegenerative disease is a tauopathy.

6. The method of claim 5, wherein the tauopathy is selected from the group consisting of Alzheimer's Disease, Progressive Supranuclear Palsy, Corticobasal Degeneration, Argyrophilic Grain Disease, Pick's Disease, and familial frontotemporal dementia.

7. The method of claim 1, wherein the composition is a pharmaceutical composition that is administered orally.

8. The method of claim 7, wherein the pharmaceutical composition is in a form selected from the group consisting of a powder, tablet, capsule, orodispersible tablet, soft capsule, aqueous medicine, syrup, elixir, and a sachet.

9. The method of claim 1, wherein the composition is a pharmaceutical composition that is administered transdermally.

10. The method of claim 1, wherein the composition is a pharmaceutical composition that is administered transnasally.

11. The method of claim 1, wherein the subject is a human subject.

12. The method of claim 1, wherein the composition is a pharmaceutical composition and further comprises an active ingredient selected from the group consisting of an antioxidant, an acetylcholine esterase inhibitor, and combinations thereof.

13. The method of claim 1, wherein the effective amount is a dosage from about 100 to about 1000 mg per day.

14. The method of claim 13, wherein the dosage is from about 200 to about 600 mg per day.

15. The method of claim 1, wherein the frequency of administration is monthly, biweekly, weekly, or daily.

16. The method of claim 15, wherein the frequency of administration is daily.

17. The method of claim 16, wherein the administration is in a single dose.

18. The method of claim 16, wherein the administration is in divided doses.

19. The method of claim 1, wherein the composition is administered orally.

20. The method of claim 19, wherein the composition is in a form selected from the group consisting of a powder, tablet, capsule, orodispersible tablet, soft capsule, aqueous medicine, syrup, elixir, and a sachet.

21. The method of claim 1, wherein the composition further comprises an active ingredient selected from the group consisting of an antioxidant, an acetylcholine esterase inhibitor, and combinations thereof.

22. The method of claim 1, wherein the grape seed extract has less than about 8% by weight of galloylated proanthocyanidins based on the total weight of proanthocyanidins in the extract.

23. The method of claim 1, wherein the grape seed extract has less than about 5% by weight of galloylated proanthocyanidins based on the total weight of proanthocyanidins in the extract.

24. The method of claim 1, wherein the grape seed extract has between 6% and 12% by weight of galloylated proanthocyanidins based on the total weight of proanthocyanidins in the extract.

25. The method of claim 1, wherein the grape seed extract has about 11% by weight of galloylated proanthocyanidins based on the total weight of proanthocyanidins in the extract.

* * * * *

UNITED STATES PATENT AND TRADEMARK OFFICE
CERTIFICATE OF CORRECTION

| | |
|---|---|
| PATENT NO. | : 8,747,924 B2 |
| APPLICATION NO. | : 12/942785 |
| DATED | : June 10, 2014 |
| INVENTOR(S) | : Giulio Maria Pasinetti, Lap Ho and Jun Wang |

Page 1 of 4

It is certified that error appears in the above-identified patent and that said Letters Patent is hereby corrected as shown below:

On the title page, under abstract "25 Claims, 30 Drawing Sheets" should read -- 25 Claims, 32 Drawing Sheets --.

IN THE DRAWINGS:

Insert Figure 1C-F after Drawing Sheet 1 of the patent with the two attached Drawing Sheets depicting Figure 1C-F.

Replace Drawing Sheet 15 of the patent depicting Figure 13A-B with the attached Drawing Sheet depicting Figure 13A-D.

Signed and Sealed this
Twenty-third Day of September, 2014

Michelle K. Lee
*Deputy Director of the United States Patent and Trademark Office*

| Grape Seed extract | % galloylated |
|---|---|
| MNG®-Az | 11 |
| Meganatural®-gold | 21 |
| GSE Brand A | 36 |
| GSE Brand B | 24 |
| GSE Brand C | 24 |

| Grape Seed extract | total | monomers | dimers | trimers | tetramers | pentamers |
|---|---|---|---|---|---|---|
| Meganatural®-gold | 47.8 | 6.5 | 20.6 | 13.7 | 5.7 | 1.2 |
| MNG®-Az | 28.3 | 5.2 | 13.5 | 6.2 | 3.5 | 0 |
| GSE Brand A | 62 | 10.5 | 32.1 | 13.7 | 3.8 | 1.8 |
| GSE Brand B | 119.2 | 22.2 | 61.1 | 26.7 | 7.6 | 1.7 |
| GSE Brand C | 99.5 | 13.6 | 47.1 | 24.9 | 9.2 | 4.9 |